United States Patent
Saka et al.

(10) Patent No.: US 11,981,956 B2
(45) Date of Patent: May 14, 2024

(54) PROXIMITY DETECTION METHODS AND COMPOSITIONS

(71) Applicant: President and Fellows of Harvard College, Cambridge, MA (US)

(72) Inventors: Sinem K. Saka, Cambridge, MA (US); Jocelyn Yoshiko Kishi, Cambridge, MA (US); Peng Yin, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 608 days.

(21) Appl. No.: 16/964,527

(22) PCT Filed: Jan. 25, 2019

(86) PCT No.: PCT/US2019/015161
§ 371 (c)(1),
(2) Date: Jul. 23, 2020

(87) PCT Pub. No.: WO2019/147945
PCT Pub. Date: Aug. 1, 2019

(65) Prior Publication Data
US 2021/0147902 A1    May 20, 2021

Related U.S. Application Data

(60) Provisional application No. 62/622,738, filed on Jan. 26, 2018, provisional application No. 62/622,731, filed on Jan. 26, 2018.

(51) Int. Cl.
*C12Q 1/682* (2018.01)
*C12Q 1/6804* (2018.01)

(52) U.S. Cl.
CPC .......... *C12Q 1/682* (2013.01); *C12Q 1/6804* (2013.01)

(58) Field of Classification Search
CPC ............................ C12Q 1/6804; C12Q 1/682; C12Q 2525/301; C12Q 2537/1376; G01N 2458/10
See application file for complete search history.

(56) References Cited

U.S. PATENT DOCUMENTS

| | | | |
|---|---|---|---|
| 5,030,566 | A | 7/1991 | Son et al. |
| 5,543,507 | A | 8/1996 | Cook et al. |
| 5,635,352 | A | 6/1997 | Urdea et al. |
| 5,866,336 | A | 2/1999 | Nazarenko et al. |
| 6,143,495 | A | 11/2000 | Lizardi et al. |

(Continued)

FOREIGN PATENT DOCUMENTS

| CN | 1432061 A | 7/2003 |
|---|---|---|
| CN | 1836050 A | 9/2006 |

(Continued)

OTHER PUBLICATIONS

[No Author Listed], New COVID-19 Variants. Centers for Disease Control and Prevention. Updated Jan. 15, 2021. 3 pages.

(Continued)

*Primary Examiner* — Samuel C Woolwine
(74) *Attorney, Agent, or Firm* — Wolf, Greenfield & Sacks, P.C.

(57) ABSTRACT

Provided herein, in some embodiments, are compositions and methods for proximity detection of molecular targets.

20 Claims, 24 Drawing Sheets

(56) References Cited

U.S. PATENT DOCUMENTS

| | | | |
|---|---|---|---|
| 7,033,758 | B2 | 4/2006 | Kenny et al. |
| 8,623,602 | B2 | 1/2014 | Kubista et al. |
| 8,772,011 | B2 | 7/2014 | De Maria et al. |
| 8,962,241 | B2 | 2/2015 | Yin et al. |
| 9,284,602 | B2 | 3/2016 | Zhang et al. |
| 9,879,313 | B2 | 1/2018 | Chee et al. |
| 10,024,796 | B2 | 7/2018 | Lin et al. |
| 10,036,059 | B2 | 7/2018 | Zhang et al. |
| 10,815,519 | B2 * | 10/2020 | Husain ............. G01N 33/54306 |
| 10,876,971 | B2 | 12/2020 | Lin et al. |
| 11,098,355 | B2 | 8/2021 | Heron et al. |
| 11,286,517 | B2 | 3/2022 | Kishi et al. |
| 11,492,661 | B2 | 11/2022 | Kishi et al. |
| 11,639,522 | B2 | 5/2023 | Schaus et al. |
| 2002/0064772 | A1 | 5/2002 | Gildea et al. |
| 2003/0148335 | A1 | 8/2003 | Shen et al. |
| 2003/0165917 | A1 | 9/2003 | Ullman et al. |
| 2003/0207292 | A1 | 11/2003 | Notomi et al. |
| 2005/0009050 | A1 | 1/2005 | Nadeau et al. |
| 2006/0063196 | A1 | 3/2006 | Akeson et al. |
| 2006/0188902 | A1 | 8/2006 | Narayanan et al. |
| 2007/0003950 | A1 | 1/2007 | Shen et al. |
| 2007/0026430 | A1 | 2/2007 | Andersen et al. |
| 2008/0021205 | A1 | 1/2008 | Blau et al. |
| 2011/0129834 | A1 | 6/2011 | Chen et al. |
| 2012/0021410 | A1 | 1/2012 | Yin et al. |
| 2012/0022243 | A1 | 1/2012 | Yin |
| 2013/0072390 | A1 | 3/2013 | Wang et al. |
| 2013/0261019 | A1 | 10/2013 | Lin et al. |
| 2014/0255921 | A1 | 9/2014 | Moysey et al. |
| 2014/0349288 | A1 | 11/2014 | Church et al. |
| 2016/0312272 | A1 | 10/2016 | Barish et al. |
| 2017/0009278 | A1 * | 1/2017 | Söderberg ............. C12Q 1/6841 |
| 2017/0327888 | A1 | 11/2017 | Ong et al. |
| 2017/0349939 | A1 | 12/2017 | Metzker et al. |
| 2018/0010174 | A1 | 1/2018 | Schaus et al. |
| 2018/0073068 | A1 | 3/2018 | Peter et al. |
| 2018/0148775 | A1 | 5/2018 | Wang et al. |
| 2018/0164308 | A1 * | 6/2018 | Walter ................. C12Q 1/6874 |
| 2018/0363045 | A1 | 12/2018 | Zhang et al. |
| 2019/0003973 | A1 | 1/2019 | Lin et al. |
| 2019/0106733 | A1 | 4/2019 | Kishi et al. |
| 2019/0285644 | A1 | 9/2019 | Regev et al. |
| 2020/0102556 | A1 | 4/2020 | Da Veiga Beltrame et al. |
| 2020/0109426 | A1 | 4/2020 | Xuan et al. |
| 2020/0362398 | A1 | 11/2020 | Kishi et al. |
| 2021/0277452 | A1 | 9/2021 | Kim et al. |
| 2021/0388430 | A1 | 12/2021 | Zhang et al. |
| 2022/0348990 | A1 | 11/2022 | Kishi et al. |
| 2023/0159996 | A1 | 5/2023 | Kishi et al. |

FOREIGN PATENT DOCUMENTS

| | | |
|---|---|---|
| CN | 101048505 A | 10/2007 |
| CN | 101541975 A | 9/2009 |
| CN | 101935697 A | 1/2011 |
| CN | 102317471 A | 1/2012 |
| CN | 102782158 A | 11/2012 |
| CN | 103014168 A | 4/2013 |
| CN | 104164488 A | 11/2014 |
| CN | 105392898 A | 3/2016 |
| CN | 106170564 A | 11/2016 |
| JP | 2008-017853 A | 1/2008 |
| JP | 2013-540451 A | 11/2013 |
| JP | 2014-504153 A | 2/2014 |
| JP | 2015-523864 A | 8/2015 |
| JP | 2002-503948 A | 5/2020 |
| WO | WO 2007/117256 A1 | 10/2007 |
| WO | WO 2010/146349 A1 | 12/2010 |
| WO | WO 2012/078312 A1 | 12/2010 |
| WO | WO 2011/156434 A2 | 12/2011 |
| WO | WO 2012/057689 A1 | 5/2012 |
| WO | WO 2012/058488 A1 | 5/2012 |
| WO | WO 2012/071428 A2 | 5/2012 |
| WO | WO 2013/012434 A1 | 1/2013 |
| WO | WO 2013/188912 A1 | 12/2013 |
| WO | WO 2014/130388 A1 | 8/2014 |
| WO | WO 2014/144371 A1 | 9/2014 |
| WO | WO 2015/095633 A1 | 6/2015 |
| WO | WO 2015/114469 A2 | 8/2015 |
| WO | WO 2015/118029 A1 | 8/2015 |
| WO | WO 2015/178978 A2 | 11/2015 |
| WO | WO 2016/123419 A1 | 8/2016 |
| WO | WO 2017/143006 A1 | 8/2017 |
| WO | WO 2017/205719 A1 | 11/2017 |
| WO | WO 2018/132392 A2 | 7/2018 |

OTHER PUBLICATIONS

Choi et al., Programmable in situ amplification for multiplexed imaging of mRNA expression. Nat Biotechnol. Nov. 2010;28(11):1208-12. Epub Oct. 31, 2010.

Fujimo et al., Quick, Selective and Reversible Photocrosslinking Reaction between 5-Methylcytosine and 3-Cyanovinylcarbazole in DNA Double Strand. Int J Mol Sci. Mar. 12, 2013;14(3):5765-74. doi: 10.3390/ijms14035765.

Ge et al., A highly sensitive target-primed rolling circle amplification (TPRCA) method for fluorescent in situ hybridization detection of microRNA in tumor cells. Anal Chem. Feb. 4, 2014;86(3):1808-15. Epub Jan. 21, 2014.

Jiang et al., Real-time detection of isothermal amplification reactions with thermostable catalytic hairpin assembly. J Am Chem Soc. May 22, 2013;135(20):7430-3 and Supporting Information. doi: 10.1021/ja4023978. Epub May 9, 2013.

Nilsson et al., Real-time monitoring of rolling-circle amplification using a modified molecular beacon design. Nucleic Acids Res. Jul. 15, 2002;30(14):e66.

Nilsson, M. Lock and roll: single-molecule genotyping in situ using padlock probes and rolling-circle amplification. Histochem Cell Biol. Aug. 2006;126(2):159-64. Epub Jun. 29, 2006.

Sah et al., Complete Genome Sequence of a 2019 Novel Coronavirus (SARS-COV-2) Strain Isolated in Nepal. Microbiol Resour Announc. Mar. 12, 2020;9(11):e00169-20. doi: 10.1128/MRA.00169-20.

Tisza et al., Discovery of several thousand highly diverse circular DNA viruses. Elife. Feb. 4, 2020;9:e51971. doi: 10.7554/eLife.51971.

Urbaneck et al., Small RNA Detection by in Situ Hybridization Methods. Int J Mol Sci. Jun. 10, 2015;16(6):13259-86.

Zeberg et al., The major genetic risk factor for severe COVID-19 is inherited from Neanderthals. Nature. Nov. 2020;587(7835):610-612. doi: 10.1038/s41586-020-2818-3. Epub Sep. 30, 2020.

Zhang et al., Fluorescence detection of telomerase activity based on signal amplification of hybridization chain reaction combining with magnetic separation. Acta Chimica Sinica. Jun. 15, 2016;74(6):513-17. doi: 10.6023/A16030136.

Zhao et al., Rolling circle amplification: applications in nanotechnology and biodetection with functional nucleic acids. Angew Chem Int Ed Engl. 2008;47(34):6330-7.

Invitation to Pay Additional Fees mailed Apr. 2, 2019 for Application No. PCT/US2019/015161.

International Search Report and Written Opinion for Application No. PCT/US2019/015161 dated May 24, 2019.

International Preliminary Report on Patentability dated Aug. 6, 2020, for Application No. PCT/US2019/015161.

Baccouche et al., Dynamic DNA-toolbox reaction circuits: a walk-through. Methods. May 15, 2014;67(2):234-49. doi: 10.1016/j.ymeth.2014.01.015. Epub Feb. 2, 2014.

Beliveau et al., Single-molecule super-resolution imaging of chromosomes and in situ haplotype visualization using Oligopaint FISH probes. Nat Commun. May 2015;6:7147(1-13).

Beliveau et al., Versatile design and synthesis platform for visualizing genomes with Oligopaint FISH probes. Proc Natl Acad Sci U S A. Dec. 26, 2012;109(52):21301-6. doi:10.1073/pnas.1213818110. Epub Dec. 11, 2012.

Chen et al., Conditionally fluorescent molecular probes for detecting single base changes in double-stranded DNA. Nat Chem. Sep. 2013;5(9):782-9. Author Manuscript, 16 pages.

(56) References Cited

OTHER PUBLICATIONS

Chhabra et al., DNA self-assembly for nanomedicine. Adv Drug Deliv Rev. Apr. 30, 2010;62(6):617-25. doi:10.1016/j.addr.2010.03.005. Epub Mar. 15, 2010.
Collins et al., A branched DNA signal amplification assay for quantification of nucleic acid targets below 100 molecules/ml. Nucl Acids Res. Aug. 1997;25(15):2979-2984.
Douglas et al., Self-assembly of DNA into nanoscale three-dimensional shapes. Nature. May 21, 2009;459(7245):414-8. doi: 10.1038/nature08016.
Fiandaca et al., Self-reporting PNA/DNA primers for PCR analysis. Genome Res. Apr. 2001;11(4):609-13. doi: 10.1101/gr.170401.
Forster et al., A human gut bacterial genome and culture collection for improved metagenomic analyses. Nat Biotechnol. 2019;37(2):186-192. doi:10.1038/s41587-018-0009-7.
Green et al., Toehold switches: de-novo-designed regulators of gene expression. Cell. Nov. 6, 2014;159(4):925-39. doi: 10.1016/j.cell.2014.10.002. Epub Oct. 23, 2014.
Hollenstein. DNA Synthesis by primer exchange reaction cascades. Chembiochem. Mar. 2, 2018;19(5):422-4. Epub Jan. 24, 2018.
Jungmann et al., Multiplexed 3D cellular super-resolution imaging with DNA-PAINT and Exchange-PAINT. Nat Methods. Mar. 2014;11(3):313-8. doi: 10.1038/nmeth.2835. Epub Feb. 2, 2014.
Jungmann et al., Nanoscale imaging in DNA nanotechnology. Wiley Interdiscip Rev Nanomed Nanobiotechnol. Jan.-Feb. 2012;4(1):66-81. doi:10.1002/wnan.173. Epub Nov. 23, 2011.
Jungmann et al., Single-molecule kinetics and super-resolution microscopy by fluorescence imaging of transient binding on DNA origami. Nano Lett. Nov. 10, 2010;10(11):4756-61.
Kishi et al., Programmable autonomous synthesis of single-stranded DNA. Nat Chem. Feb. 2018;10(2):155-64. Epub Nov. 6, 2017. Author Manuscript, 22 pages.
Li et al., Multiplexed detection of pathogen DNA with DNA-based fluorescence nanobarcodes. Nat Biotechnol. Jul. 2005;23(7):885-9. Epub Jun. 12, 2005.
Lin et al., Functional DNA nanotube arrays: bottom-up meets top-down. Angewandte Chemie. 2007;119(32):6201-4.
Lin et al., Self-assembled combinatorial encoding nanoarrays for multiplexed biosensing. Nano Lett. Feb. 2007;7(2):507-12.
Montagne et al., Programming an in vitro DNA oscillator using a molecular networking strategy. Mol Syst Biol. Feb. 1, 2011;7:466. doi: 10.1038/msb.2010.120. Erratum in: Mol Syst Biol. Mar. 8, 2011;7:476. Mol Syst Biol. 2011;7. doi: 10.1038/msb.2011.12.
Nazarenko et al., Multiplex quantitative PCR using self-quenched primers labeled with a single fluorophore. Nucleic Acids Res. May 1, 2002;30(9):e37(1-7). doi: 10.1093/nar/30.9.e37.
Player et al., Single-copy gene detection using branched DNA (bDNA) in situ hybridization. J Histochem & Cytochem. May 2001;49(5):603-11.
Rothemund, Folding DNA to create nanoscale shapes and patterns. Nature. Mar. 16, 2006;440(7082):297-302.
Simonsson et al., A substrate for telomerase. Trends Biochem Sci. Dec. 2003;28(12):632-8. doi: 10.1016/j.tibs.2003.10.005.
Wang et al, RNAscope: A novel in situ RNA analysis platform for formalin-fixed, paraffin-embedded tissues. J Mol Diagn. Jan. 2012;14(1):22-9.
Wang et al., Proximity hybridization-regulated immunoassay for cell surface protein and protein-overexpressing cancer cells via electrochemiluminescence. Anal Chem. Mar. 6, 2018;90(5):3013-8. Epub Feb. 23, 2018.
Weibrecht et al., In situ detetion of individual mRNA molecules and protein complexes or post-translational modifications using padlock probes combined with the in situ proximity ligation assay. Nat Protoc. Feb. 2013;8(2):355-72.
Weibrecht et al., Proximity ligation assays: a recetn addition to the proteomics toolbox. Expert Rev of Proteomics. Jun. 2010;7(3):401-9.
Wharam et al., Specific detection of DNA and RNA targets using a novel isothermal nucleic acid amplification assay based on the formation of a three-way junction structure. Nucleic Acids Res. Jun. 1, 2001;29(11):E54-4.
Woehrstein et al., Sub-100 nm metafluorophores with digitally tunable optical properties self-assembled from DNA. Sci Adv. Jun. 21, 2017;3(6):e1602128.
Wu et al., A nonenzymatic hairpin DNA Cascade reaction provides high signal gain of mRNA imagin inside live cells. J Am Chem Soc. Apr. 2015; 137(15):4900-3.
Yin et al., Programming biomolecular self-assembly pathways. Nature. Jan. 17, 2008;451(7176):318-22. doi:10.1038/nature06451.
Yin et al., Programming DNA tube circumferences. Science. Aug. 8, 2008;321(5890):824-6. doi:10.1126/science.1157312.
Zhang et al., Control of DNA strand displacement kinetics using toehold exchange. J Am Chem Soc. Dec. 2, 2009;131(47):17303-14. doi: 10.1021/ja906987s.
Zhang et al., Dynamic DNA nanotechnology using strand-displacement reactions. Nat Chem. 2011;3(2):103-13.
Zhang et al., Optimizing the specificity of nucleic acid hybridization. Nat Chem. Epub Jan. 22, 2012, 7 pages.
Zhu et al., Toehold-mediated strand displacement reaction triggered isothermal DNA amplification for highly sensitive and selective fluorescent detection of single-base mutation. Biosens Bioelectron. Sep. 15, 2014;59:276-81. doi: 10.1016/j.bios.2014.03.051. Epub Apr. 1, 2014.
Yurke et al., A DNA-fuelled molecular machine made of DNA. Nature. Aug. 10, 2000;406(6796):605-8.

* cited by examiner

PROXIMITY DETECTION METHODS AND COMPOSITIONS

RELATED APPLICATIONS

This application is a national stage filing under 35 U.S.C. § 371 of international application number PCT/US2019/015161, filed Jan. 25, 2019, which claims the benefit under 35 U.S.C. § 119(e) of U.S. provisional application No. 62/622,731, filed Jan. 26, 2018, and U.S. provisional application No. 62/622,738, filed Jan. 26, 2018, each of which is incorporated by reference herein in its entirety.

FEDERALLY SPONSORED RESEARCH

This invention was made with government support under N00014-16-1-2410 awarded by Department of Defense, under EB018659 and HL145600 awarded by National Institutes of Health, and under 1317291 awarded by National Science Foundation. The government has certain rights in the invention.

BACKGROUND

Low signal and high background are important limitations that hamper the sensitivity and accuracy of molecular detection systems. Presented herein is a technology referred to as a "proximity primer exchange reaction (ProPER) that can be used to achieve high sensitivity and accuracy in target detection. By relying on the successful targeting of multiple strands to a single target of interest, the background of detection may be significantly decreased. The long concatemer produced by ProPER can be used as a scaffold for fluorescent molecules, enabling the use of ProPER as a form of signal amplification. This allows the aggregation of potentially dozens (or more) of detectable entities (e.g., fluorophores) to single target biomolecules, for example, producing signal which can then be visualized directly on a microscope or fluorescence scanner.

Further presented herein is a technology referred to as a "co-zipper primer exchange reaction" (Co-Zipper) that relies on the discrimination between cooperative binding of two domains versus a single domain. This enables fluorophore-labeled imager strands that bind two coincident concatemers (two nucleic acid strands) to aggregate many fluorophores to a target molecule or area with high specificity. Low background is achieved by relying on the proximity of the concatemers—the probability that two discrete concatemers bind to an off-target is extremely low. The combination of this high specificity with the linear amplification achieved through the repeated binding of imagers to concatemers enables the application of Co-Zipper for highly specific and highly sensitive biomarker detection (e.g., diagnostics) and imaging, for example.

SUMMARY

Provided herein are proximity-based methods and compositions that enable highly specific (e.g., high resolution, low background) detection of molecular targets and molecular target interactions. The methods of the present disclosure rely on coincident detection of nucleic acid molecules, in some instances, concatemeric molecules, within close proximity of one another (e.g., within 100 nanometers (nm), within 75 nm, within 50 nm, within 25 nm, within 10 nm, or within 5 nm of one another). In some embodiments, the methods provided herein build on a catalytic reaction referred to as a primer exchange reaction (PER). Primer exchange reactions rely on a catalytic hairpin that is used to append a primer sequence to create a concatemer by tandem repeating of a desired sequence domain. See, e.g., International Publication No. WO 2017/143006, published Aug. 24, 2017, incorporated herein by reference in its entirety. It should be understood that any of the strands comprising a tandem repeat sequence (e.g., a concatemer strand and/or concatemer-forming strand) may be produced using a primer exchange reaction. Further, in some embodiments, it may be advantage to produce any of the strands comprising a tandem repeat sequence using a rolling circle amplification reaction, or any other nucleic acid synthesis method in situ or in vitro.

In some aspects, the present disclosure provides a method (and associated compositions) referred to herein as a "proximity primer exchange reaction" or a "ProPER," which advances the PER concatemerization reaction by relying on spatial proximity of a fixed primer strand and a fixed hairpin strand, referred to herein respectively as the concatemer-forming strand and the catalytic strand. The ProPER system is designed such that a detectable signal depends on formation of a localized concatemer, which is produced only when the concatemer-forming strand and the catalytic strand are co-localized, indicative of co-localization of the substrates to which the strands are linked. FIG. 4, for example, depicts a concatemer-forming strand (left) in close proximity to a catalytic strand (right), resulting in a tandem repeat of domain 'a' appended to the concatemer-forming strand. Following hybridization and visualization of a labeled 'imager' strand comprising a repeat of the complement domain 'a*', the presence of this concatemer-forming strand can be detected.

In other aspects, the present disclosure provides a method (and associated compositions) referred to herein as a "co-zipper reaction" or a "Co-Zipper," which is designed such that a detectable signal depends on co-localization of two different concatemer strands, indicative of co-localization of the substrates to which the strands are linked. FIG. 11A, for example, depicts a first concatemer strand comprising tandem repeats of domain 'a' (right) in close proximity to a second concatemer strand comprising tandem repeats of domain 'b' (left). Following hybridization and visualization of a labeled 'imager' strand comprising the complement domain 'a*' and the complement domain 'b*', the presence of both concatemer strands can be detected.

Some aspects of the present disclosure provide a composition comprising: a first target-binding molecule that binds specifically to a first target molecule; a catalytic strand comprising a hairpin with a stem and a loop, wherein the catalytic strand can bind to the first target-binding molecule; a concatemer-forming strand comprising a tandem repeat of a primer domain, wherein the primer can bind to the stem, thereby linearizing the hairpin, optionally wherein the concatemer-forming strand can bind to the first target-binding molecule; and a labeled imager strand that can bind to the primer domain and/or the tandem repeat of the concatemer-forming strand. In some embodiments, the concatemer-forming strand can bind to a second target-binding molecule.

Some aspects of the present disclosure provide a composition comprising: a first strand comprising domain X*, a first domain a*, a second domain a*, and domain a; a second strand comprising domain Y* and domain a; a labeled imager strand comprising a first domain a* and a second domain a*; and optionally polymerase and/or dNTPs, wherein domain X*, domain Y*, and domain a* each comprise a nucleotide sequence complementary to a nucleotide sequence of domain X, domain Y, and domain a, respectively, and wherein domain X is located on a target strand and domain Y is located on a target strand.

Some aspects of the present disclosure provide a composition comprising: a first target-binding molecule that binds specifically to a first target molecule; a first concatemer strand comprising a first set of tandem repeat sequences, wherein the first concatemer strand can bind to the first target-binding molecule; and a second concatemer strand comprising a second set of tandem repeat sequences, optionally wherein the second concatemer strand can bind to the first target-binding molecule; and a labeled imager strand that can bind simultaneously to tandem repeat sequences of the first concatemer strand and to tandem repeat sequences of the second concatemer strand.

Some aspects of the present disclosure provide a composition comprising: a first concatemer strand comprising domain X* and tandem repeats of domain a; a second concatemer strand comprising domain Y* and tandem repeats of domain b; and a labeled imager strand comprising domain a* and domain b*, wherein domain X*, domain Y*, domain a*, and domain b* each comprise a nucleotide sequence complementary to a nucleotide sequence of domain X, domain Y, domain a, and domain b, respectively, and wherein domain X is located on a target strand and domain Y is located on a target strand.

Other aspects provide a method of screening for a target molecule, the method comprising contacting a composition suspected of comprising a target molecule with any of the compositions provided herein, and detecting presence or absence of the labeled imager strand, wherein presence of the labeled imager strand indicates presence of the target molecule.

Yet other aspects provide a method of detecting a target molecule, the method comprising contacting the target molecule with any of the compositions provided herein and detecting the labeled imager strand, thereby detecting the target molecule.

Still other aspects provide a method of screening for an interaction between two target molecules, the method comprising contacting a composition suspected of comprising target molecules with any of the compositions provided herein, and detecting presence or absence of the labeled imager strand, wherein presence of the labeled imager strand indicates presence of an interaction between the target molecules.

Further aspects provide a method of detecting an interaction between two target molecules, the method comprising contacting a first target molecule and a second target molecule with any of the compositions provided herein and detecting the labeled imager strand, thereby detecting an interaction between the first target molecule and the second target molecule.

BRIEF DESCRIPTION OF THE DRAWINGS

FIG. 1A is a schematic in which a target strand (also referred to as a splint strand), with a 10-nucleotide linker region between domains 'X' and 'Y', serves as a substrate to co-localize a concatemer-forming strand containing primer 'a' with a catalytic strand. FIG. 1B is a TBE-Urea PAGE denaturing gel scanned under a Cy5 channel to visualize concatemerization using ProPER.

FIG. 2A is a schematic in which a target molecule, with a variable length (0 to 18 nucleotides) linker region between domains 'X' and 'Y', serves as a substrate to co-localize a concatemer-forming strand containing primer 'a' with a catalytic strand. FIG. 2B is a TBE-Urea PAGE denaturing gel scanned under a Cy5 channel to visualize concatemerization using ProPER. The distance between domain X and domain Y varies from 0, 5, 10, 15, and 18 nucleotides.

FIG. 3A shows an example of a ProPER used to detect a nucleic acid target (DNA/RNA), where the concatemer-forming strand and catalytic strand are designed only to co-localize in the presence of the target strand. FIG. 3B shows an example of ProPER used to target a linker strand (also referred to as a bridge strand) conjugated to an antibody that binds to a protein of interest. FIG. 3C shows an example of ProPER used to detect a single target protein. A concatemer-forming strand is linked to one antibody that binds the target protein and a catalytic strand is linked to another antibody that binds a different region (e.g., epitope) of the same target protein. FIG. 3D shows an example of ProPER used to detect an interaction between two different target proteins, for example, within the same biomolecular complex. A concatemer-forming strand is linked to one antibody that binds one target protein and a catalytic strand is linked to another antibody that binds another target protein.

FIG. 6A is a schematic illustrating the target binding specifically enabled by the use of additional hairpins being proximal to the concatemer-forming strand. For example, two hairpins localized to the 'a' primer domain may produce a concatemer comprising repeats of the sequence 'a'-'b'. FIG. 6B is a schematic showing the use of three hairpins to produce a concatemer with repeats of the sequence 'a'-'b'-'c'. The number of hairpins can be further increased for additional information and specificity.

FIG. 7A is a schematic demonstrating the use of a repetitive in vitro PER to generate long concatemers with one concatemer-forming strand followed by a stepwise PER hairpin to append a new concatemer-forming strand sequence onto the concatemer. FIG. 7B is a schematic that shows a FISH reaction combining probe sequences containing 42 mer 'bridge' overhangs with complementary in vitro prepared PER concatemers and catalytic hairpin strands. The probes bound to targeted regions in a tiled manner along the target nucleic acid, with some bound to catalytic hairpin strands and others bound to concatemers. Proximity-dependent PER was then performed to extend the concatemer-forming strands, and fluorophore imagers were hybridized to both concatemer sequences for imaging.

FIG. 8A shows that one 200 kb spot (Spot X) of eighteen total was targeted using an in vitro PER followed by a proximity dependent in situ PER strategy as described in FIGS. 7A-7B. Underlying Cy3-labeled probes were hybridized to Spot X along with the 17 remaining 200 kb spots to illuminate the entire chromosome. All DNA was imaged using DAPI. FIGS. 8B-8C are representative fields of view that show expected co-localization of 488 and 647 channels. They further show positioning of this co-localized region within the larger Cy3-labeled chromosome.

FIG. 9A is a schematic showing in vitro synthesized probe concatemers tiled with alternate sequences that serve as scaffolds for PER primer and hairpin binding strands to localize many primers and hairpins nearby one another. Proximity-dependent PER was then used to create a new proximity-dependent concatemer sequence, which can be hybridized to fluorescently-labeled imager strands. FIG. 9B shows experimental validation of the branched proximity-dependent PER strategy using probes targeting the Cbx5 mRNA in fixed EY.T4 cells. PER signal was visualized in the 647 channel and the DAPI stain enables visualization of cell nuclei. Scale bar: 10 microns.

FIG. 10A shows a visualization of Lamin A by primary and secondary antibodies. Top row shows the Cy5 signal from the fluorescent primer. Middle row shows the ATTO565 signal from the imagers that bind to the proximity-extended concatemer. Bottom row shows the overlay of both images (Cy5, ATTO565) and DAPI. Scale bar: 20 μm. FIG. 10B shows a visualization of TOM20 by primary and secondary antibodies. The rows are organized as described for FIG. 10A.

FIG. 11A shows an example of a Co-Zipper used to detect a nucleic acid target (DNA/RNA), where the concatemer-forming strand and catalytic strand are designed only to co-localize in the presence of the target strand. FIG. 11B shows an example of a Co-Zipper used to target a linker strand (also referred to as a bridge strand) conjugated to an antibody that binds to a protein of interest. FIG. 11C shows an example of a Co-Zipper used to detect a single target protein. A first concatemer strand is linked to one antibody that binds the target protein and a second concatemer strand is linked to another antibody that binds a different region (e.g., epitope) of the same target protein. FIG. 11D shows an example of a Co-Zipper used to detect an interaction between two different target proteins, for example, within the same biomolecular complex. A first concatemer strand is linked to one antibody that binds one target protein and a second concatemer strand is linked to another antibody that binds another target protein.

FIG. 14A is a schematic of a HCR. Addition of an initiator strand of DNA (1+x) to a metastable mixture of two hairpin species triggers a chain reaction of hybridization events wherein hairpins form a long double-stranded concatemer. Normally, conjugation of fluorophores onto hairpins provides linear amplification. For the Co-Zipper adaptation, an extra toehold domain (of sequence 'a') is appended to one of the hairpins, instead of the fluorophores. FIG. 14B is a schematic showing the co-detection of double-stranded assemblies formed by HCR, as enabled by proximity imager ('a*'+'b*'). Single stranded toehold domains ('a' and 'b') that extend out of the double-stranded HCR product can maintain stable binding to imager strands only when both domains are in close proximity to one another.

DETAILED DESCRIPTION

Figure 1A:
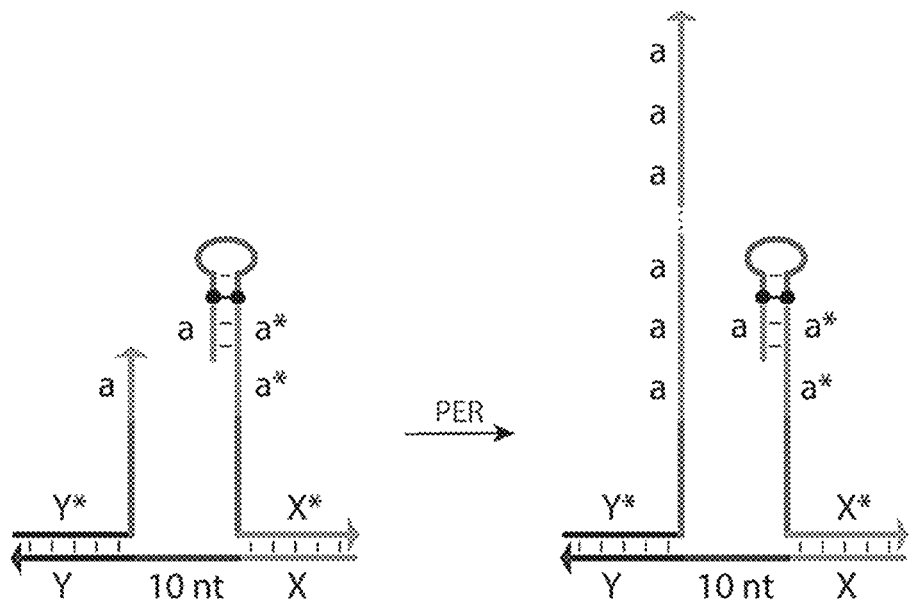
FIGS. 1A-1B provide experimental validation of a Proximity Primer Exchange Reaction (ProPER).

A "strand," as used herein, is a single-stranded (unpaired) nucleic acid (e.g., DNA and/or RNA). The length of any of the strands provided herein (e.g., a catalytic strand, a concatemer-forming strand, a first concatemer strand, a second concatemer strand, a linker strand, a primer strand, and/or an imager strand) may vary. In some embodiments, the length of a strand is 5-10,000 nucleotides (5 nm-10 μm). For example, a strand may have a length of 5-10000, 5-5000, 5-1000, 5-500, 5-450, 5-400, 5-350, 5-300, 5-250, 5-200, 5-150, 5-100, 5-50, 10-10000, 10-5000, 10-1000, 10-500, 10-450, 10-400, 10-350, 10-300, 10-250, 10-200, 10-150, 10-100, 10-50, 20-10000, 20-5000, 20-1000, 20-500, 20-450, 20-400, 20-350, 20-300, 20-250, 20-200, 20-150, 20-100, 20-50, 30-10000, 30-5000, 30-1000, 30-500, 30-450, 30-400, 30-350, 30-300, 30-250, 30-200, 30-150, 30-100, 30-50, 40-10000, 40-5000, 40-1000, 40-500, 40-450, 40-400, 40-350, 40-300, 40-250, 40-200, 40-150, 40-100, 40-50, 50-10000, 50-5000, 50-1000, 50-500, 50-450, 50-400, 50-350, 50-300, 50-250, 50-200, 50-150, 50-100, 50-50, 60-10000, 60-5000, 60-1000, 60-500, 60-450, 60-400, 60-350, 60-300, 60-250, 60-200, 60-150, 60-100, 60-50, 70-10000, 70-5000, 70-1000, 70-500, 70-450, 70-400, 70-350, 70-300, 70-250, 70-200, 70-150, 70-100, 70-50, 80-10000, 80-5000, 80-1000, 80-500, 80-450, 80-400, 80-350, 80-300, 80-250, 80-200, 80-150, 80-100, 80-50, 90-10000, 90-5000, 90-1000, 90-500, 90-450, 90-400, 90-350, 90-300, 90-250, 90-200, 90-150, 90-100, 100-10000, 100-5000, 100-1000, 100-500, 100-450, 100-400, 100-350, 100-300, 100-250, 100-200, or 100-150 nucleotides. In some embodiments, a strand has a length of 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, or 500 nucleotides.

Any of the strands provided herein may be modified with a molecule that enables direct detection of the strand (e.g., by fluorescent microscopy or other imaging method). Non-limiting examples of such "modifier molecules" include fluorophores, quantum dots, polymer dots, metal ions, biotin, horseradish peroxidase, magnetic particles, and tyramide.

A "domain" is simply a defined stretch of contiguous nucleotides within a longer nucleic acid. Thus, a strand may have multiple domains. The length of any of the domains provided herein may vary. In some embodiments, the length of a domain (e.g., stem domain, loop domain, primer domain, domain 'a', domain 'a*', domain 'X', domain 'X*', domain 'Y', and/or domain 'Y*') is 3-100 nucleotides. For example, a domain may have a length of 3-90, 3-80, 3-70, 3-60, 3-50, 3-40, 3-30, 3-20, 3-10, 4-90, 4-80, 4-70, 4-60, 4-50, 4-40, 4-30, 4-20, 4-10, 5-90, 5-80, 5-70, 5-60, 5-50, 5-40, 5-30, 5-20, 5-10, 10-90, 10-80, 10-70, 10-60, 10-50, 10-40, 10-30, 10-20, 15-90, 15-80, 15-70, 15-60, 15-50, 15-40, 15-30, 15-20, 20-90, 20-80, 20-70, 20-60, 20-50, 20-40, 20-30, 25-90, 25-80, 25-70, 25-60, 25-50, 25-40, or 25-30 nucleotides. In some embodiments, a domain has a length of 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides.

It should be understand that domains, as provided herein, may bind to (hybridize to) each other through complementary nucleotide base pairing. Thus, domain 'a' of any one of the embodiments provided herein may comprise a nucleotide sequence that is complementary to, and thus capable of binding to, a nucleotide sequence of domain 'a*'. Similarly, domain 'b' of any one of the embodiments provided herein may comprise a nucleotide sequence that is complementary to, and thus capable of binding to, a nucleotide sequence of domain 'b*'; domain 'w' of any one of the embodiments provided herein may comprise a nucleotide sequence that is complementary to, and thus capable of binding to, a nucleotide sequence of domain 'w*'; domain 'z' of any one of the embodiments provided herein may comprise a nucleotide sequence that is complementary to, and thus capable of binding to, a nucleotide sequence of domain 'z*'; domain '1' of any one of the embodiments provided herein may comprise a nucleotide sequence that is complementary to, and thus capable of binding to, a nucleotide sequence of domain '1*'; domain '2' of any one of the embodiments provided herein may comprise a nucleotide sequence that is complementary to, and thus capable of binding to, a nucleotide sequence of domain '2*'; domain '3' of any one of the embodiments provided herein may comprise a nucleotide sequence that is complementary to, and thus capable of binding to, a nucleotide sequence of domain '3*'; domain '4' of any one of the embodiments provided herein may comprise a nucleotide sequence that is complementary to, and thus capable of binding to, a nucleotide sequence of domain '4*'; domain 'X' of any one of the embodiments provided herein may comprise a nucleotide sequence that is complementary to, and thus capable of binding to, a nucleotide sequence of domain 'X*'; and domain 'Y' of any one of the embodiments provided herein may comprise a nucleotide sequence that is complementary to, and thus capable of binding to, a nucleotide sequence of domain 'Y*'.

Proximity Primer Exchange Reaction (ProPER)

The Proximity Primer Exchange Reaction (ProPER) utilizes a concatemerization reaction that relies on the spatial proximity of a concatemer-forming strand and a catalytic strand, which when co-localized, interact to produce a long, localized concatemer. Production of the concatemer is indicative of the presence of an immobilized target or the presence of an interaction between two or more immobilized targets. Operation of the proximity-based detection, in some embodiments, relies on reaction conditions, such as salt and temperature. Other conditions, such as the distance between the regions to which the concatemer-forming strand and the catalytic strand bind (e.g., domains 'Y*' and 'X*' in FIGS. 1A-1B) can also affect concatemerization efficiency.

Some aspects of the present disclosure provide a composition comprising a first target-binding molecule that binds specifically to a first target molecule, a catalytic strand comprising a hairpin with a stem and a loop, wherein the catalytic strand can bind to the first target-binding molecule, a concatemer-forming strand comprising a tandem repeat of a primer domain, wherein the primer can bind to the stem, thereby linearizing the hairpin, optionally wherein the concatemer-forming strand can bind to the first target-binding molecule, and a labeled imager strand that can bind to the primer domain and/or the tandem repeat of the concatemer-forming strand.

Other aspects of the present disclosure provide a composition comprising: a first strand comprising domain X*, a first domain a*, a second domain a*, and domain a; a second strand comprising domain Y* and domain a; a labeled imager strand comprising a first domain a* and a second domain a*, wherein domain X*, domain Y*, and domain a* each comprise a nucleotide sequence complementary to a nucleotide sequence of domain X, domain Y, and domain a, respectively, and wherein domain X is located on a target strand and domain Y is located on a target strand.

Still other aspects of the present disclosure provide a composition, comprising: (a) labeled probe strands, wherein each probe strand comprises domain 'a' and domain 'b', (b) concatemer strands, wherein each concatemer comprises domain 'b*', a set of tandem repeat sequences, and a primer domain, (c) catalytic strands, wherein each catalytic strand comprises domain 'b*', a stem, and a loop, and wherein the primer domain comprises a sequence complementary to sequence of the stem, (d) a first labeled imager strand comprising a sequence complementary to a tandem repeat sequence of the concatemer strand, (e) a second labeled imager strand comprising a sequence complementary to the primer domain of the concatemer strand, optionally (f) polymerase, optionally a strand displacing polymerase, and/or dNTPs, and optionally (g) a target strand comprising domain 'a*', wherein domain 'a' and domain 'b' each comprise a sequence complementary to a sequence of domain 'a*' and domain 'b*', respectively.

Catalytic Strands

In some embodiments, a catalytic strand comprises a hairpin with a stem (stem domain) and a loop (loop domain). That is, a catalytic strand is a single-stranded nucleic acid that forms a hairpin shape through intramolecular binding at the stem. FIG. 1A provides an example of a catalytic strand comprising, in the 5' to 3' direction, domain 'a', a loop, a first domain 'a*', a second domain 'a*', and domain 'X*'. The nucleotide sequence within domain 'a' is complementary to the nucleotide sequence within domain 'a*', thus domain 'a' is capable of binding (hybridizing) to domain 'a*' to form a stem with an intervening loop.

The length of a catalytic strand and the domains within a catalytic strand may vary. In some embodiments, the length of catalytic strand is 20-500 nucleotides. For example, a catalytic strand may have a length of 20-450, 20-400, 20-350, 20-300, 20-250, 20-200, 20-150, 20-100, 20-50, 30-500, 30-450, 30-400, 30-350, 30-300, 30-250, 30-200, 30-150, 30-100, 30-50, 40-500, 40-450, 40-400, 40-350, 40-300, 40-250, 40-200, 40-150, 40-100, 40-50, 50-500, 50-450, 50-400, 50-350, 50-300, 50-250, 50-200, 50-150, 50-100, 50-50, 60-500, 60-450, 60-400, 60-350, 60-300, 60-250, 60-200, 60-150, 60-100, 60-50, 70-500, 70-450, 70-400, 70-350, 70-300, 70-250, 70-200, 70-150, 70-100, 70-50, 80-500, 80-450, 80-400, 80-350, 80-300, 80-250, 80-200, 80-150, 80-100, 80-50, 90-500, 90-450, 90-400, 90-350, 90-300, 90-250, 90-200, 90-150, 90-100, 100-500, 100-450, 100-400, 100-350, 100-300, 100-250, 100-200, or 100-150 nucleotides. In some embodiments, a catalytic strand has a length of 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, or 500 nucleotides.

The length of a stem may vary. In some embodiments, the length of a stem is 3-100 nucleotides. For example, a stem may have a length of 3-90, 3-80, 3-70, 3-60, 3-50, 3-40, 3-30, 3-20, 3-10, 4-90, 4-80, 4-70, 4-60, 4-50, 4-40, 4-30, 4-20, 4-10, 5-90, 5-80, 5-70, 5-60, 5-50, 5-40, 5-30, 5-20, 5-10, 10-90, 10-80, 10-70, 10-60, 10-50, 10-40, 10-30, 10-20, 15-90, 15-80, 15-70, 15-60, 15-50, 15-40, 15-30, 15-20, 20-90, 20-80, 20-70, 20-60, 20-50, 20-40, 20-30, 25-90, 25-80, 25-70, 25-60, 25-50, 25-40, or 25-30 nucleotides. In some embodiments, a stem has a length of 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides.

The length of a loop may vary. In some embodiments, the length of a loop is 3-100 nucleotides. For example, a loop may have a length of 3-90, 3-80, 3-70, 3-60, 3-50, 3-40, 3-30, 3-20, 3-10, 4-90, 4-80, 4-70, 4-60, 4-50, 4-40, 4-30, 4-20, 4-10, 5-90, 5-80, 5-70, 5-60, 5-50, 5-40, 5-30, 5-20, 5-10, 10-90, 10-80, 10-70, 10-60, 10-50, 10-40, 10-30, 10-20, 15-90, 15-80, 15-70, 15-60, 15-50, 15-40, 15-30, 15-20, 20-90, 20-80, 20-70, 20-60, 20-50, 20-40, 20-30, 25-90, 25-80, 25-70, 25-60, 25-50, 25-40, or 25-30 nucleotides. In some embodiments, a loop has a length of 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides.

In some embodiments, a catalytic strand comprises a molecule or modification that terminates polymerization. Extension of a primer domain of a concatemer-forming strand (bound to a catalytic strand) by a strand displacing polymerase is terminated by the presence of a molecule or modification in the catalytic strand that terminates polymerization. A molecule or modification that terminates polymerization ("stopper") is typically located in a stem domain of a catalytic molecule such that polymerization terminates extension of the primer through the stem domain. For catalytic strands arranged in the form of a hairpin, a molecule or modification that terminates polymerization may be located between the stem domain and the loop. In some embodiments, the molecule that terminate polymerization is a synthetic non-DNA linker, for example, a triethylene glycol spacer, such as the Int Spacer 9 (iSp9) or Spacer 18 (Integrated DNA Technologies (IDT)). It should be understood that any non-native linker that terminates polymerization by a polymerase may be used as provided herein. Other non-limiting examples of such molecules and modifications include a three-carbon linkage (/iSpC3/) (IDT), ACRYDITE™ (IDT), adenylation, azide, digoxigenin (NHS ester), cholesteryl-TEG (IDT), I-LINKER™ (IDT), and 3-cyanovinylcarbazole (CNVK) and variants thereof. Typically, but not always, short linkers (e.g., iSp9) lead to faster reaction times.

In some embodiments, the molecule that terminates polymerization is a single or paired non-natural nucleotide sequence, such as iso-dG and iso-dC (IDT), which are chemical variants of cytosine and guanine, respectively. Iso-dC will base pair (hydrogen bond) with Iso-dG but not with dG. Similarly, Iso-dG will base pair with Iso-dC but not with dC. By incorporating these nucleotides in a pair on opposite sides of the hairpin, at the stopper position, the polymerase will be halted, as it does not have a complementary nucleotide in solution to add at that position.

In some embodiments, the efficiency of performance of a "stopper" modification is improved by lowering dNTP concentrations (e.g., from 200 µM) in a reaction to 100 µM, 10 µM, 1 µM, or less.

Inclusion of a molecule or modification that terminates polymerization often creates a "bulge" in a stem domain of catalytic strand, because the molecule or modification is not paired (bound to another molecule). Thus, in some embodiments, catalytic molecules are designed to include, opposite the molecule or modification, a single nucleotide (e.g., thymine), at least two of same nucleotide (e.g., a thymine dimer (TT) or trimer (TTT)), or an non-natural modification.

Concatemer-Forming Strands

In some embodiments, a concatemer-forming strand comprises a tandem repeat of a primer domain. A "tandem repeat" of a sequence is an adjacent duplication of a particular sequence. For example, the sequence ATCGATCG is a tandem repeat of ATCG. The number of tandem repeat sequences (e.g., the number of primer domains) in a concatemer-forming strand may vary. In some embodiments, a concatemer-forming strand comprises 2-100 tandem repeat sequences. For example, a concatemer-forming strand may comprise 2-90, 2-80, 2-70, 2-60, 2-50, 2-40, 2-30, 2-20, 2-10, 3-100, 3-90, 3-80, 3-70, 3-60, 3-50, 3-40, 3-30, 3-20, 3-10, 4-90, 4-80, 4-70, 4-60, 4-50, 4-40, 4-30, 4-20, 4-10, 5-90, 5-80, 5-70, 5-60, 5-50, 5-40, 5-30, 5-20, 5-10, 10-90, 10-80, 10-70, 10-60, 10-50, 10-40, 10-30, 10-20, 15-90, 15-80, 15-70, 15-60, 15-50, 15-40, 15-30, 15-20, 20-90, 20-80, 20-70, 20-60, 20-50, 20-40, 20-30, 25-90, 25-80, 25-70, 25-60, 25-50, 25-40, or 25-30 tandem repeat sequences (e.g., primer domains). In some embodiments, a concatemer-forming strand comprises 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 tandem repeat sequences (e.g., primer domains). In some embodiments, tandem repeats have a length of 20 nucleotides or shorter, or a length of 5 to 15 nucleotides. In some embodiments, a concatemer-forming strand comprises two or more tandem repeats of a primer domain.

The length of a concatemer-forming strand and the primer domain within a concatemer-forming strand may vary. In some embodiments, the length of a concatemer-forming strand is 1 nm-10 µm. In some embodiments, the length of a concatemer-forming strand is 20-500 nucleotides. For example, a concatemer-forming strand may have a length of 20-450, 20-400, 20-350, 20-300, 20-250, 20-200, 20-150, 20-100, 20-50, 30-500, 30-450, 30-400, 30-350, 30-300, 30-250, 30-200, 30-150, 30-100, 30-50, 40-500, 40-450, 40-400, 40-350, 40-300, 40-250, 40-200, 40-150, 40-100, 40-50, 50-500, 50-450, 50-400, 50-350, 50-300, 50-250, 50-200, 50-150, 50-100, 50-50, 60-500, 60-450, 60-400, 60-350, 60-300, 60-250, 60-200, 60-150, 60-100, 60-50, 70-500, 70-450, 70-400, 70-350, 70-300, 70-250, 70-200, 70-150, 70-100, 70-50, 80-500, 80-450, 80-400, 80-350, 80-300, 80-250, 80-200, 80-150, 80-100, 80-50, 90-500, 90-450, 90-400, 90-350, 90-300, 90-250, 90-200, 90-150, 90-100, 100-500, 100-450, 100-400, 100-350, 100-300, 100-250, 100-200, or 100-150 nucleotides. In some embodiments, a concatemer-forming strand has a length of 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, or 500 nucleotides.

In some embodiments, the length of a primer domain is 3-100 nucleotides. For example, a primer domain may have a length of 3-90, 3-80, 3-70, 3-60, 3-50, 3-40, 3-30, 3-20, 3-10, 4-90, 4-80, 4-70, 4-60, 4-50, 4-40, 4-30, 4-20, 4-10, 5-90, 5-80, 5-70, 5-60, 5-50, 5-40, 5-30, 5-20, 5-10, 10-90, 10-80, 10-70, 10-60, 10-50, 10-40, 10-30, 10-20, 15-90, 15-80, 15-70, 15-60, 15-50, 15-40, 15-30, 15-20, 20-90, 20-80, 20-70, 20-60, 20-50, 20-40, 20-30, 25-90, 25-80, 25-70, 25-60, 25-50, 25-40, or 25-30 nucleotides. In some embodiments, a primer domain has a length of 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides.

In some embodiments, the primer domain of a concatemer-forming strand can bind to the stem of a catalytic strand, thereby linearizing the hairpin. With reference to FIG. 1A, for example, primer domain 'a' of the concatemer-forming strand (left) can bind to domain 'a*' of the stem of the catalytic strand, and in the presence of strand-displacing polymerase and dNTPs, the catalytic strand "opens" (the stem region dissociates) and serves as a template for appending a tandem repeat of domain 'a' onto the concatemer-forming strand. The stem of the catalytic strand then reforms. This cycle repeats to form a concatemer of tandem repeats of domain 'a'.

Probe Strands

In some embodiments, a probe strand comprises a detectable label, such as a fluorophore, a domain that binds to a target strand, and a domain that binds to a concatemer strand. In some embodiments, a probe strand comprises domain 'a' and domain 'b' such that the probe strand binds to a target strand comprising domain 'a*' and binds to a concatemer strand comprising domain 'b'. The length of a probe strand may vary. In some embodiments, the length of an probe strand is 3-50 nucleotides. For example, a probe strand may have a length of 3-40, 3-30, 3-20, 3-10, 4-50, 4-40, 4-30, 4-20, 4-10, 5-50, 5-40, 5-30, 5-20, 5-10, 10-50, 10-40, 10-30, 10-20, 15-50, 15-40, 15-30, 15-20, 20-50, 20-40, 20-30, 25-50, 25-40, or 25-30 nucleotides. In some embodiments, the length of a probe strand is 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides.

ProPER Imager Strands

Figure 4:
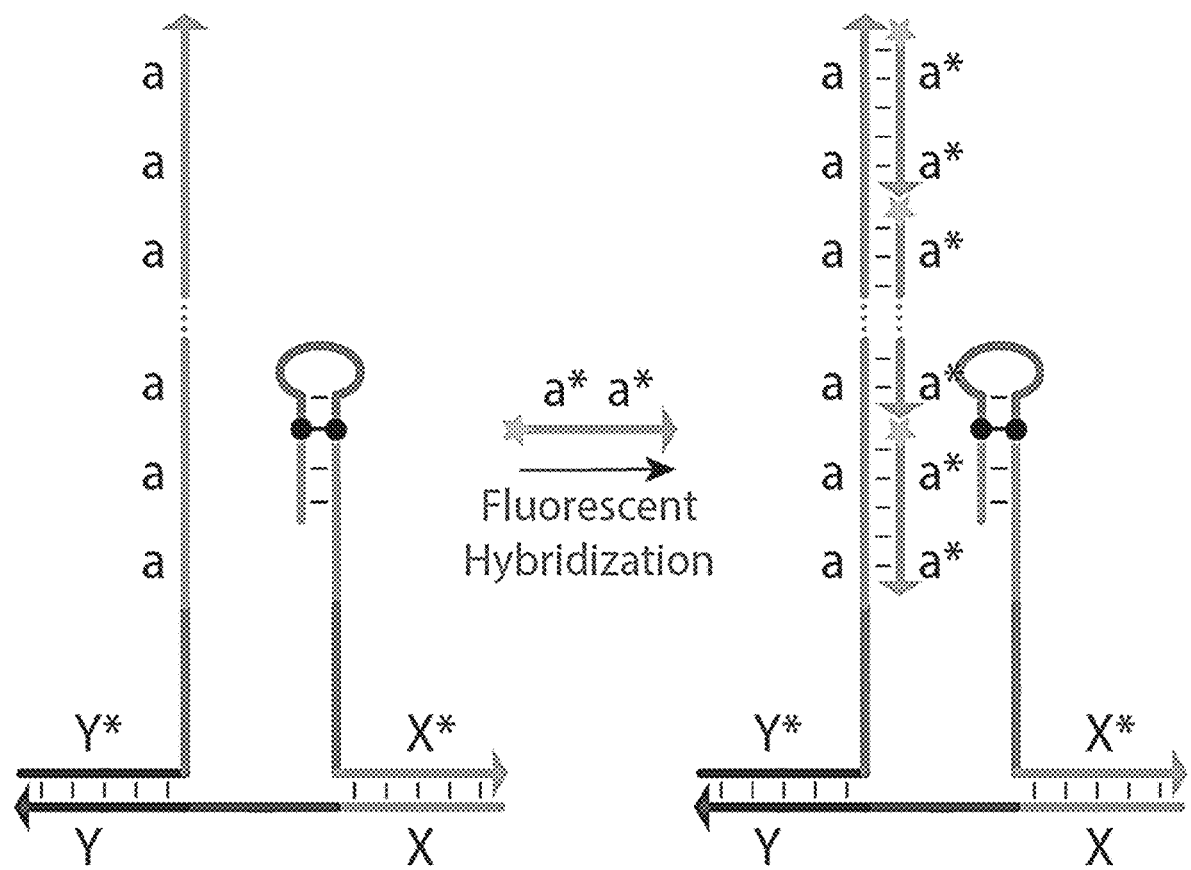
FIG. 4 is a schematic showing that a concatemer produced by ProPER can be subsequently hybridized to complementary fluorescent imager strands, such as with the two-domain a* a* strand depicted. The strength of the fluorescence signal reflects the length of the concatemer produced, and fluorescence may be visualized, for example, in bulk (e.g., targets and concatemers may be fixed to a surface and the total level of fluorescence is measured) or using microscopy to reveal the spatial positioning of the concatemers.

Imager strands, in some embodiments, are short strands that can bind to tandem repeats of a concatemer-forming strand (see, e.g., FIG. 4). In some embodiments, an imager strand comprises a detectable label, such as a fluorophore. The length of an imager strand may vary. In some embodiments, the length of an imager strand is 5-200 nucleotides. In some embodiments, the length of an imager strand is 3-50 nucleotides. For example, an imager strand may have a length of 3-40, 3-30, 3-20, 3-10, 4-50, 4-40, 4-30, 4-20, 4-10, 5-50, 5-40, 5-30, 5-20, 5-10, 10-50, 10-40, 10-30, 10-20, 15-50, 15-40, 15-30, 15-20, 20-50, 20-40, 20-30, 25-50, 25-40, or 25-30 nucleotides. In some embodiments, the length of an imager strand is 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides. In some embodiments, an imager strand comprises a first domain 'a*' and a second domain 'a*' such that the imager strand binds to a concatemer-forming strand comprising a tandem repeat of domain 'a'.

Examples of fluorophores that may be used herein, for example, as labels for a probe strand/and or an imager strand include, without limitation, hydroxycoumarin, methoxycoumarin, Alexa fluor, aminocoumarin, Cy2, FAM, Alexa fluor 405, Alexa fluor 488, Fluorescein FITC, Alexa fluor 430, Alexa fluor 532, HEX, Cy3, TRITC, Alexa fluor 546, Alexa fluor 555, R-phycoerythrin (PE), Rhodamine Red-X, Tamara, Cy3.5 581, Rox, Alexa fluor 568, Red 613, Texas Red, Alexa fluor 594, Alexa fluor 633, Allophycocyanin, Alexa fluor 647, Cy5, Alexa fluor 660, Cy5.5, TruRed, Alexa fluor 680, Cy7 and Cy7.5. Other fluorescent molecules may be used.

In some embodiments, an imager strand (or any other strand described herein) may be labeled (e.g., linked to) a moiety selected from the group consisting of: fluorophores, quantum dots, polymer dots, metal ions, biotin, horseradish peroxidase, tyramide. Other detectable modifier groups are also encompassed herein.

Imager strand may be detected, for example, directly on a concatemer or concatemer-forming strand or may be released via dehybridization (e.g., by modification of the buffer ionic composition or addition of chemicals such as formamide or DMSO, or by application of heat) to be detected by various readout methods appropriate for specific modifications. Detection methods include, without limitation, microscopy, fluorescence scanning, flow cytometry, mass cytometry, mass spectrometry mass-based detection, magnetic methods, aggregate solution based methods (e.g. intercalating dyes like SYBR green), chemical pull-downs, enzymatic assays, and/or sequencing.

Compositions

ProPER compositions of the present disclosure are described by the following numbered paragraphs:

1. A composition comprising:
    a first target-binding molecule that binds specifically to a first target molecule;
    a catalytic strand comprising a hairpin with a stem and a loop, wherein the catalytic strand can bind to the first target-binding molecule;
    a concatemer-forming strand comprising a tandem repeat of a primer domain, wherein the primer can bind to the stem, thereby linearizing the hairpin, optionally wherein the concatemer-forming strand can bind to the first target-binding molecule; and
    a labeled imager strand that can bind to the primer domain and/or the tandem repeat of the concatemer-forming strand. See, e.g., FIG. 3B.
2. The composition of paragraph 1 further comprising a polymerase, optionally a strand-displacing polymerase, and/or dNTPs.
3. The composition of paragraph 1 or 2 further comprising an excess (e.g., 2-fold, 3-fold, 5-fold, 10-fold, 25-fold, 50-fold, or 100-fold excess) of catalytic strands to which the primer of the concatemer-forming strand can bind.
4. The composition of any one of paragraphs 1-3, wherein the first target-binding molecule is a polypeptide, optionally wherein the polypeptide is an antibody.

5. The composition of any one of paragraphs 1-4, wherein the concatemer-forming strand comprises two or more tandem repeats of the primer domain.
6. The composition of any one of paragraphs 1-5, wherein the tandem repeats have a length of 5 nm to 1000 nm.
7. The composition of any one of paragraphs 1-6, wherein the concatemer-forming strand can bind to the first target-binding molecule.
8. The composition of any one of paragraphs 1-7, wherein the catalytic strand and concatemer-forming strand bind to the first target-binding molecule through an intermediate linker.
9. The composition of any one of paragraphs 1-8, wherein the first target-binding molecule is linked to a first linker strand comprising a first domain to which the catalytic strand can bind.
10. The composition of paragraph 9, wherein the first linker strand further comprises a second domain to which the concatemer-forming strand can bind. See, e.g., FIG. 3B.
11. The composition of paragraph 10, wherein the first domain is separated from the second domain by 1 nm to 10 µm.
12. The composition of paragraph 10, wherein the first domain and/or the second domain has a length of 1 nm to 10 µm.
13. The composition of any one of paragraphs 9-12, wherein the first linker strand has a length of 1 nm to 10 µm.
14. The composition of any one of paragraphs 1-13 further comprising the first target molecule, optionally wherein the target molecule is a DNA, a RNA, or a protein, and optionally wherein the target molecule is present in a fixed tissue.
15. The composition of any one of paragraphs 1-6, wherein the concatemer-forming strand can bind to a second target-binding molecule. See, e.g., FIG. 3C.
16. The composition of paragraph 15, wherein the second target-binding molecule is linked to a second linker strand comprising a second domain to which the concatemer-forming strand can bind. See, e.g., FIG. 3C.
17. The composition of any one of paragraphs 9-16, wherein first linker strand strand has a length of 1 nm to 10 µm.
18. The composition of paragraph 16 or 17, wherein the second linker strand has a length of 1 nm to 10 µm.
19. The composition of paragraph 17 or 18 further comprising the second target-binding molecule.
20. The composition of paragraph 19, wherein the second target-binding molecule binds specifically to the first target molecule, optionally wherein the first and second target-binding molecules bind to different regions of the first target molecule. See, e.g., FIG. 3C.
21. The composition of any one of paragraphs 16-20, wherein the second target-binding molecule is a polypeptide, optionally wherein the polypeptide is an antibody.
22. The composition of any one of paragraphs 16-21, wherein the labeled imager strand comprises a detectable label selected from fluorophores, quantum dots, polymer dots, metal ions, biotin, horseradish peroxidase, magnetic particles, and tyramide.
23. The composition of any one of paragraphs 15-21, wherein the second target-binding molecule binds specifically to a second target molecule, optionally wherein the second target molecule is a DNA, a RNA, or a protein, and optionally wherein the second target molecule is present in a fixed tissue. See, e.g., FIG. 3D.
24. The composition of paragraph 23 further comprising the second target molecule.
25. A composition comprising: a target-binding molecule linked to (i) a catalytic strand comprising a hairpin with a stem and a loop and (ii) a concatemer-forming strand comprising a tandem repeat of a primer domain, wherein the primer domain can bind to the stem, thereby linearizing the hairpin; and a labeled imager strand that can bind to the primer domain and/or the tandem repeat of the concatemer-forming strand; and optionally a target bound by the target-binding molecule. See, e.g., FIG. 3B.
26. A composition comprising: a catalytic strand comprising a hairpin with a stem and a loop; a concatemer-forming strand comprising a tandem repeat of a primer domain, wherein the primer domain can bind to the stem, thereby linearizing the hairpin; and a labeled imager strand that can bind to the primer domain and/or the tandem repeat of the concatemer-forming strand, and optionally a target strand to which the catalytic strand and concatemer-forming strand can bind. See, e.g., FIG. 3A.
27. A composition comprising: a first strand comprising domain X*, a first domain a*, a second domain a*, and domain a; a second strand comprising domain Y* and domain a; a labeled imager strand comprising a first domain a* and a second domain a*; and optionally polymerase and/or dNTPs, wherein domain X*, domain Y*, and domain a* each comprise a nucleotide sequence complementary to a nucleotide sequence of domain X, domain Y, and domain a, respectively, and wherein domain X is located on a target strand and domain Y is located on a target strand. See, e.g., FIG. 3A.
28. The composition of paragraph 27 comprising the polymerase and/or dNTPs.
29. The composition of paragraph 27 or 28, wherein domain X and domain Y are located on the same target strand, and optionally wherein domain X and domain Y are separated from each other by a distance of 10 µm or less, or 100 nm or less. See, e.g., FIG. 3A.
30. The composition of paragraph 29, wherein the target strand is linked to a target-binding molecule, optionally wherein the target-binding molecule is a polypeptide, and optionally wherein the polypeptide is an antibody.
31. The composition of paragraph 27, wherein domain X is located on a first target strand and domain Y is located on a second target strand.
32. The composition of paragraph 31, wherein the first target strand is linked to a first target-binding molecule and the second target strand is linked to a second target-binding molecule, optionally wherein the first target-binding molecule is a first polypeptide and/or the second target-binding molecule is a second polypeptide, and optionally wherein the first polypeptide is a first antibody and/or the second polypeptide is a second antibody. See, e.g., FIG. 3C.
33. The composition of paragraph 32, wherein the first polypeptide and the second polypeptide bind specifically to the same target molecules, or wherein the first polypeptide and the second polypeptide bind specifically to different target molecules. See, e.g., FIGS. 3C and 3D.
34. A composition comprising: a first catalytic strand comprising a hairpin with a stem and a loop, optionally wherein the first catalytic strand can bind to a first target-binding molecule; a second catalytic strand comprising a hairpin with a stem and a loop, optionally wherein the second catalytic strand can bind to a second target-binding molecule; optionally a third catalytic strand comprising a hairpin with a stem and a loop, optionally wherein the third catalytic strand can bind to a third target-binding molecule; a concatemer-forming strand comprising a tandem repeat of a primer domain, wherein the primer can bind to the stem of the first catalytic strand, the second catalytic strand, and optionally the third catalytic strand, thereby linearizing the hairpins, optionally wherein the concatemer-forming strand can bind to the first target-binding molecule or to a second target-binding molecule; and a first, a second, and optionally a third labeled imager strand, each of which can bind to the tandem repeat of the concatemer-forming strand. See, e.g., FIG. 6B.

Methods

Some aspects provide a method of screening for a target molecule, the method comprising contacting a composition suspected of comprising a target molecule with a ProPER composition of the present disclosure, and detecting presence or absence of the labeled imager strand, wherein presence of the labeled imager strand indicates presence of the target molecule.

Other aspects provide a method of detecting a target molecule, the method comprising contacting the target molecule with a ProPER composition of the present disclosure and detecting the labeled imager strand, thereby detecting the target molecule.

Still other aspects provide a method of screening for an interaction between two target molecules, the method comprising contacting a composition suspected of comprising target molecules with a ProPER composition of the present disclosure, and detecting presence or absence of the labeled imager strand, wherein presence of the labeled imager strand indicates presence of an interaction between the target molecules.

Further aspects provide a method of detecting an interaction between two target molecules, the method comprising contacting a first target molecule and a second target molecule with a ProPER composition of the present disclosure and detecting the labeled imager strand, thereby detecting an interaction between the first target molecule and the second target molecule.

Another aspect provides a method comprising contacting a target strand with a catalytic strand comprising a hairpin with a stem and a loop, a concatemer-forming strand comprising a tandem repeat of a primer domain, wherein the primer domain can bind to the stem, thereby linearizing the hairpin, a labeled imager strand that can bind to the primer domain and/or the tandem repeat of the concatemer-forming strand, and polymerase and/or dNTPs, wherein the target strand comprises a first domain to which the catalytic strand can bind and a second domain to which the concatemer-forming strand can bind, and optionally wherein the first domain is separated from the second domain by 1 nm to 10 μm.

Other aspects provide a molecular detection method, comprising: (a) contacting a surface to which a target strand is linked with (i) a catalytic strand comprising a hairpin with a stem and a loop and (ii) a concatemer-forming strand comprising a tandem repeat of a primer domain, wherein the primer can bind to the stem, thereby linearizing the hairpin, optionally wherein the composition comprises an excess of the catalytic strand, and wherein the catalytic strand and the concatemer-forming strand bind to the target strand; (b) optionally washing the surface; (c) producing in the presence of polymerase and/or dNTPs additional tandem repeats of the primer domain on the concatemer-forming strand bound to the target strand; (d) contacting the concatemer-forming strand of (c) with a labeled imager strand that can bind to the tandem repeat of the concatemer-forming strand; (e) optionally washing the surface of (d); and (f) detecting the labeled imager strand. See, e.g., FIG. 5.

Given its high specificity, as well as the sensitivity arising from its linear amplification, there are many promising applications of ProPER. FIGS. 3A-3D show how the method can be used to specifically detect DNA, RNA, and protein targets, as well as how the method could be used to study interactions that happen on scales below the diffraction limit such as protein-protein binding in a biomolecular complex. Both of these applications have great potential in the development of disease diagnostic methods as well as more fundamental biological research.

Figure 5:
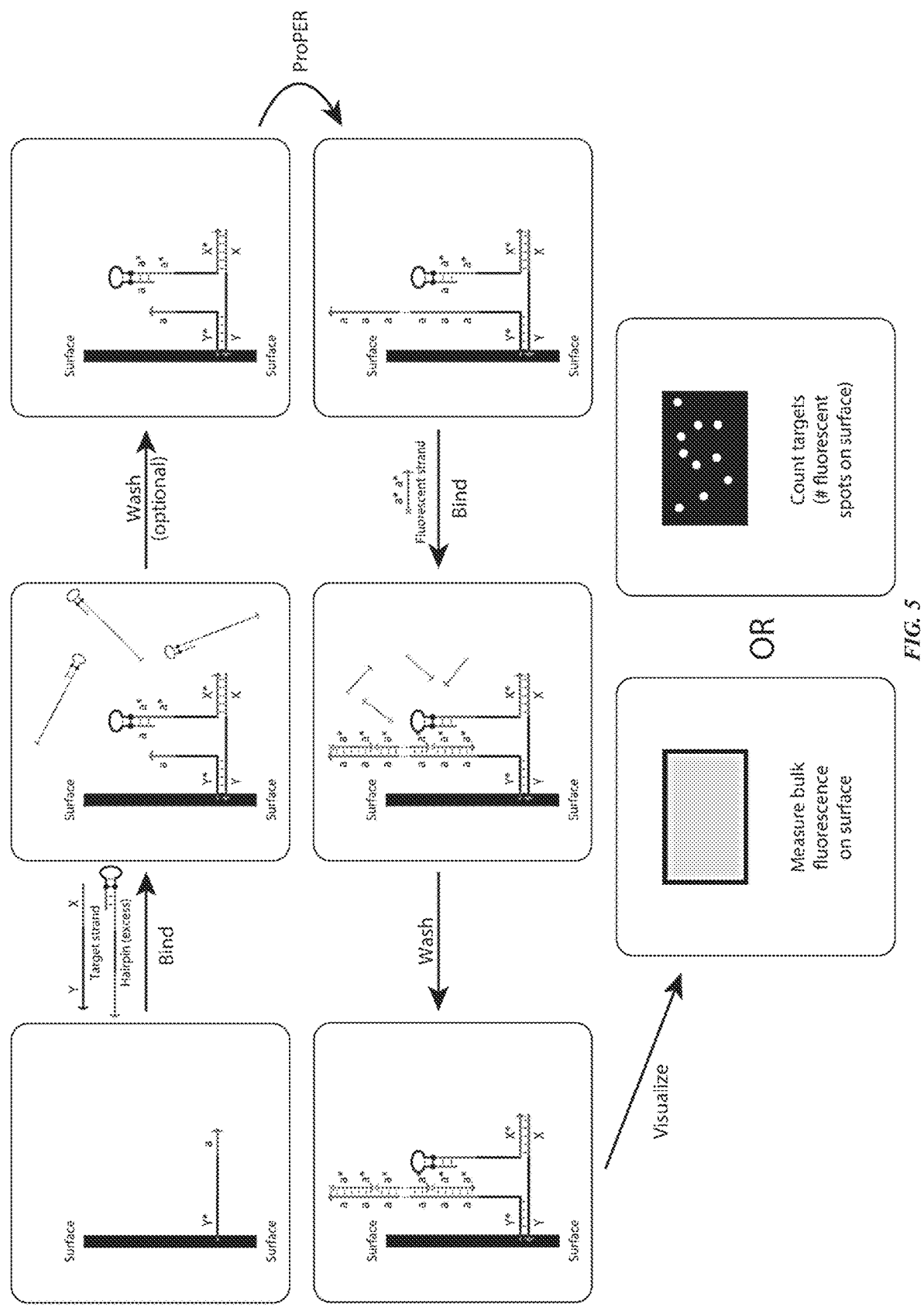
FIG. 5 is a schematic showing methods of biomarker detection using ProPER.

Highly specific and sensitive biomarker detection. In some embodiments, ProPER can be used for diagnostic applications, due to its rapid, specific, and sensitive biomarker detection. An example workflow is shown in FIG. 5. One of the components (the primer in this case) is attached to a surface (which may be paper, glass, plastic, or another substrate). Then, the remaining components (the target strand and hairpin strand strand) are bound to this substrate-bound component. For example, blood serum or other fluids containing nucleic acid analytes of interest may be pre-mixed with the hairpin, or these oligos may be introduced sequentially through bind and wash steps on the substrate. Once the primer-target-hairpin complex has been formed, the additional hairpin strands may be washed away through aspiration and re-suspension. Next, the ProPER is run to produce concatemers, one for each target molecule of interest that has bound. Fluorescent strands are introduced to bind to the concatemer and then excess unbound ones are washed away. Finally, fluorescence output is read with one of two strategies: bulk fluorescence or spot counting. For bulk fluorescence, the total fluorescence level can be read on the surface with an LED- or laser-based scanner, such as a plate reader. Alternatively, the number of individual fluorescent spots can be counted, such as with a microscope or automated counter, and the density of spots can be mapped quantitatively to a concentration estimate of the original analyte.

Interaction partner detection. In some embodiments, ProPER can be used for detection of interaction partners in solution or in situ. In this example, the primer and hairpin are attached onto different molecules of interest and the output is only generated when they are in close proximity. Because ProPER would require proximity of the components for every round of extension, higher Kd's are expected to translate into longer concatemers (which give rise to higher signal). The kinetic signal amplification offered by ProPER would feature higher sensitivity or lower background, as well as a direct output of the biomolecular interaction.

Low-background in situ imaging. In some embodiments, ProPER is used as a method for in situ imaging. Primers and hairpins can be co-localized using one of the strategies depicted in FIGS. 3A-3D to target DNA/RNA/proteins and grow concatemers in situ in a fixed tissue sample, for example. By imaging the fluorescence after hybridizing complementary fluorescent strands to these localized concatemers (see FIG. 4), the relative position of these targeted biomolecules within the sample of interest can be known.

Furthermore, because of the dependence on proximity of the primer and hairpin, the background is expected to be significantly lowered compared to normal in situ probe targeting and amplification, which typically relies only on one probe strand being localized to a target instead of two.

Exemplary ProPER Features

Specific detection: Concatemerization, in some embodiments, relies on the successful binding of two components to a target strand/protein/complex, so the specificity of the interaction is increased compared to methods that only have one detection event specific to the target. This "double-checking" has a non-linear effect on reducing background, as the probabilities of both the primer and hairpin binding the wrong target, but in proximity to each other, is now very low. If just a single component (primer/hairpin) binds to the wrong substrate, no signal will be produced. This specificity can further be increased, in some embodiments, by changing the way in which primers/hairpins bind to their targets, and/or by relying on additional proximity interactions (detection events).

Multiple proximity checks: Not only is the specificity of primer/hairpin binding to a target checked multiple times, but the proximity itself is also checked several times through the process of concatemerization. Each PER step relies on the proximity of the primer to the hairpin, so the length of the concatemer reflects the number of successful checks of proximity (proximity events). Thus, the concatemerization is a type of 'proximity proofreading'. With ProPER both the detection and proximity reactions are highly specific, resulting in a very low error rate.

Amplification: Because the output of the reaction is a long strand, it serves as a form of linear amplification. The concatemer can serve, for example, as a scaffold substrate for fluorescent strands (e.g., FIG. 4), which can be used to aggregate many fluorophores to a single concatemer. This provides a highly sensitive, simple, and cost-effective readout method for both surface- and fixed sample-based applications.

Other Embodiments

In some embodiments, target, primer, hairpin, and other (e.g. antibody) components may be annealed together (e.g. by cooling from 80° C. to 20° C. over 1 hour), or they may be combined together isothermally (e.g. at room temperature, 37° C., 46° C., etc.). They may be also bound under conditions that improve their specificity to the target strand, such as using standard ISH (In Situ Hybridization) buffers like SSCT and PBS, often with the addition of formamide.

In some embodiments, the binding of components may be done diffusively (in solution), or with one or more of the components attached to a substrate. For example, a tissue sample (target) may be fixed, and primer and hairpin strands subsequently bound to it. Alternatively, one of the primer or hairpin strands might be bound to the surface (see FIG. 5 for an example), with the other strands subsequently hybridized to the surface-bound strand.

In some embodiments, binding of the targeting regions X/X* and Y/Y* may be may be transient (such that the average dwell time is on the order of minutes or less), or they may be bound more strongly (e.g. bound time of minutes to hours or more). In addition to changing binding buffer conditions, this interaction could also be made more specific through the use of a protection strand and toehold-mediated strand displacing [5] or toehold exchange [6] that requires the target strand to compete with an existing strand.

In some embodiments, the surface in FIG. 5 could be paper, glass, plastic, or any other substrate that an oligo can somehow be attached to. Strands may be bound through absorption or drying onto the surface, or chemically binding them such as through the use of a biotin-labeled primer component and a streptavidin coated surface.

In some embodiments, the reaction and visualization workflow can be done entirely diffusively (e.g. eliminate surface from FIG. 5), and concatemerization length can be read out through existing diffusive methods such as molecular beacons [7], and FRET pair displacing (see e.g. [8]), or through gel based assays.

In some embodiments, the primer and hairpin strands themselves may be directly conjugated to the antibodies (i.e. no intermediate bridge strand).

In some embodiments, additional sequence modifications, such as spacers may be included in strands to assist flexibility and allow them to reach each other under a range of configurations.

In some embodiments, fluorescent readout can also be achieved by using fluorophore-labeled dNTPs that are incorporated during the extension reaction, so that the concatemers themselves are fluorescent.

Figure 7A:
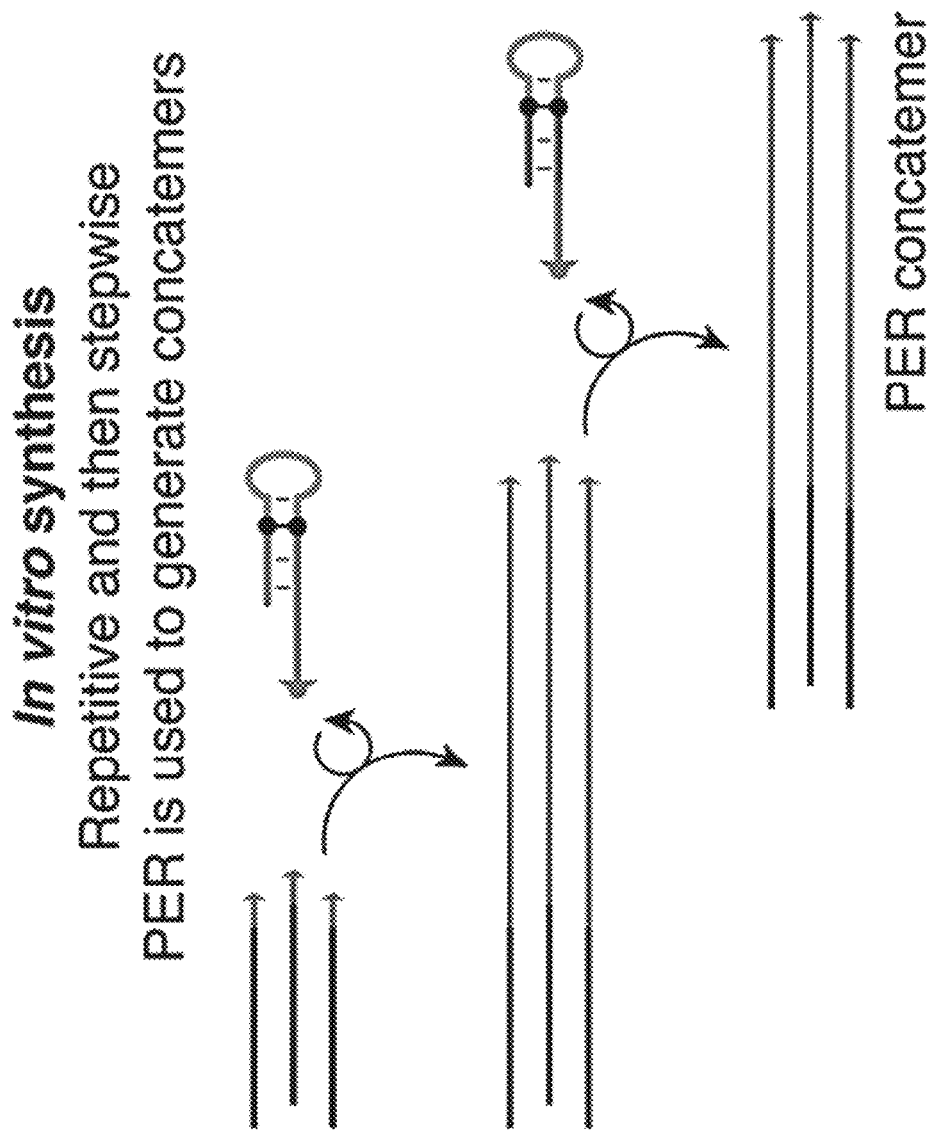
FIGS. 7A-7B provide a proximity-dependent PER using flexible PER concatemer linkers.
Figure 7B:
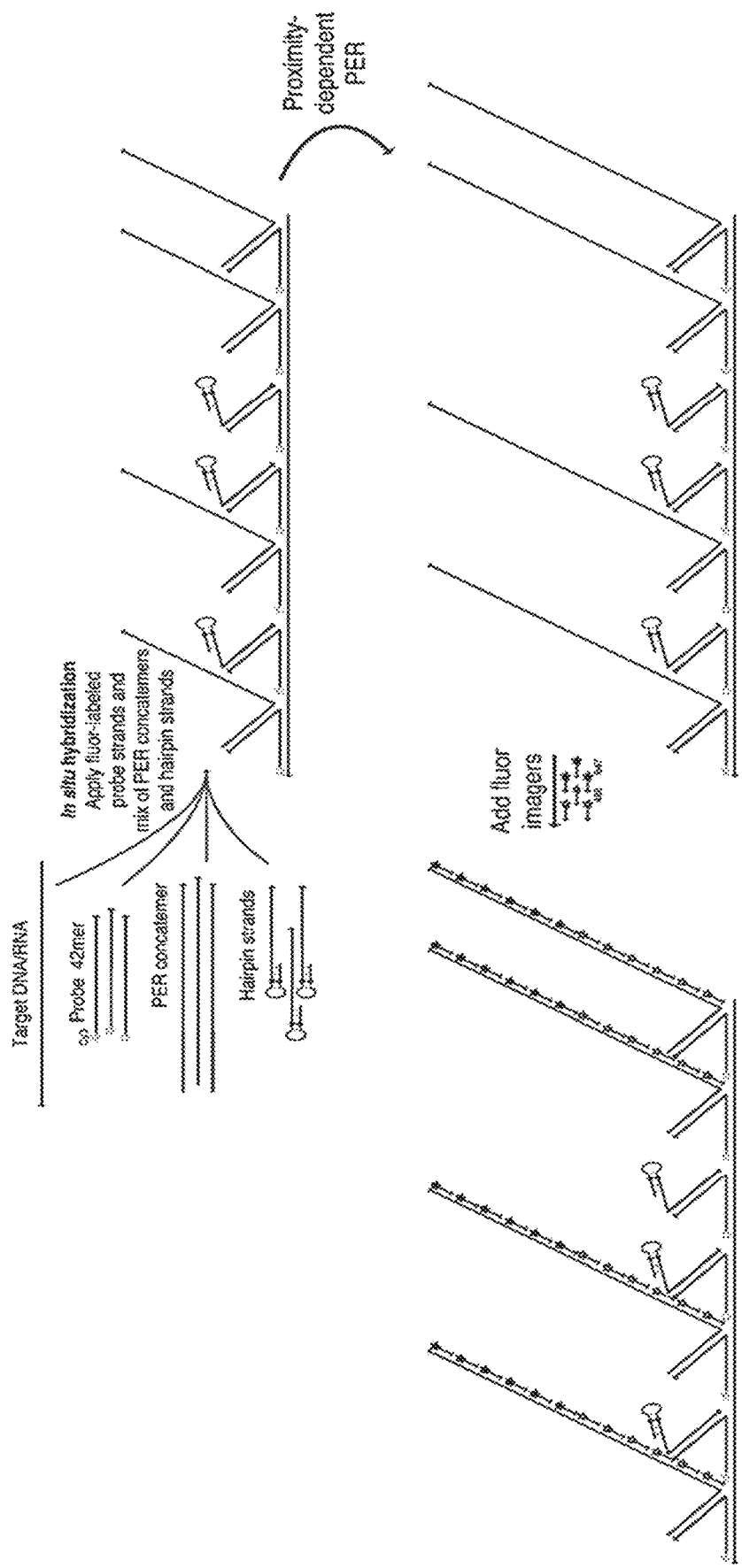

In some embodiments, an arbitrary number of proximal hairpins can be detected to further increase specificity of target binding. One method of achieving this is shown in FIGS. 7A-7B. FIG. 7A shows how two hairpins can be used to produce concatemers of the form 5'-a b a b . . . a b-3', to which a fluorescent strand complementary to the repeated units (such as 5'-b* a*-3') can be bound to produce fluorescent output. FIG. 7B shows a similar setup with 3 hairpins that produces a concatemer of the form 5'-a b c a b c . . . a b c-3'. Hybridizing a fluorescent strand with sequence 5'-c* b* a*-3', for example, would enable specific fluorescent output of the concatemer. The number of hairpins can be increased arbitrarily, so that the number of molecules that must be in spatial proximity for successful and repeated concatemerization is n+1, where n is the number of hairpins.

In some embodiments, output can be multiplexed, such as through the use of multiple orthogonal concatemerization ProPER sequences that get simultaneously extended and mapped to different fluorescence colors.

Co-Zipper Reaction

Some aspects of the present disclosure provide a composition comprising: a first target-binding molecule that binds specifically to a first target molecule; a first concatemer strand comprising a first set of tandem repeat sequences, wherein the first concatemer strand can bind to the first target-binding molecule; and a second concatemer strand comprising a second set of tandem repeat sequences, optionally wherein the second concatemer strand can bind to the first target-binding molecule; and a labeled imager strand that can bind simultaneously to tandem repeat sequences of the first concatemer strand and to tandem repeat sequences of the second concatemer strand.

Other aspects of the present disclosure provide a composition comprising a first concatemer strand comprising domain X* and tandem repeats of domain a; a second concatemer strand comprising domain Y* and tandem repeats of domain b; and a labeled imager strand comprising domain a* and domain b*, wherein domain X*, domain Y*, domain a*, and domain b* each comprise a nucleotide sequence complementary to a nucleotide sequence of domain X, domain Y, domain a, and domain b, respectively, and wherein domain X is located on a target strand and domain Y is located on a target strand.

Concatemer Strands

A concatemer strand, in some embodiments, comprising a set of tandem repeat sequences. As described herein, a "tandem repeat" of a sequence is an adjacent duplication of a particular sequence. It should be understood that a "first set" of tandem repeat sequences differs from a "second set" of tandem repeat sequences. For example, first set of tandem repeat sequences may include a tandem repeat of the sequence ATCGA, while a second set of tandem repeat sequences may include a tandem repeat of the sequence TACGT. Thus, the sequence of a "first concatemer strand" differs from the sequence of a "second concatemer strand."

The length of a first and/or second concatemer strand may vary. In some embodiments, the length of a first and/or second concatemer strand is 1 nm-10 µm. In some embodiments, the length of a first and/or second concatemer strand is 20-500 nucleotides. For example, a first and/or second concatemer strand may have a length of 20-450, 20-400, 20-350, 20-300, 20-250, 20-200, 20-150, 20-100, 20-50, 30-500, 30-450, 30-400, 30-350, 30-300, 30-250, 30-200, 30-150, 30-100, 30-50, 40-500, 40-450, 40-400, 40-350, 40-300, 40-250, 40-200, 40-150, 40-100, 40-50, 50-500, 50-450, 50-400, 50-350, 50-300, 50-250, 50-200, 50-150, 50-100, 50-50, 60-500, 60-450, 60-400, 60-350, 60-300, 60-250, 60-200, 60-150, 60-100, 60-50, 70-500, 70-450, 70-400, 70-350, 70-300, 70-250, 70-200, 70-150, 70-100, 70-50, 80-500, 80-450, 80-400, 80-350, 80-300, 80-250, 80-200, 80-150, 80-100, 80-50, 90-500, 90-450, 90-400, 90-350, 90-300, 90-250, 90-200, 90-150, 90-100, 100-500, 100-450, 100-400, 100-350, 100-300, 100-250, 100-200, or 100-150 nucleotides. In some embodiments, a first and/or second concatemer strand has a length of 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, or 500 nucleotides.

The number of tandem repeat sequences in a concatemer strand may vary. In some embodiments, a concatemer strand comprises 2-100 tandem repeat sequences. For example, a concatemer strand may comprise 2-90, 2-80, 2-70, 2-60, 2-50, 2-40, 2-30, 2-20, 2-10, 3-100, 3-90, 3-80, 3-70, 3-60, 3-50, 3-40, 3-30, 3-20, 3-10, 4-90, 4-80, 4-70, 4-60, 4-50, 4-40, 4-30, 4-20, 4-10, 5-90, 5-80, 5-70, 5-60, 5-50, 5-40, 5-30, 5-20, 5-10, 10-90, 10-80, 10-70, 10-60, 10-50, 10-40, 10-30, 10-20, 15-90, 15-80, 15-70, 15-60, 15-50, 15-40, 15-30, 15-20, 20-90, 20-80, 20-70, 20-60, 20-50, 20-40, 20-30, 25-90, 25-80, 25-70, 25-60, 25-50, 25-40, or 25-30 tandem repeat sequences. In some embodiments, a concatemer strand comprises 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 tandem repeat sequences (e.g., primer domains). In some embodiments, tandem repeats have a length of 20 nucleotides or shorter, or a length of 5 to 15 nucleotides.

Figure 14A:
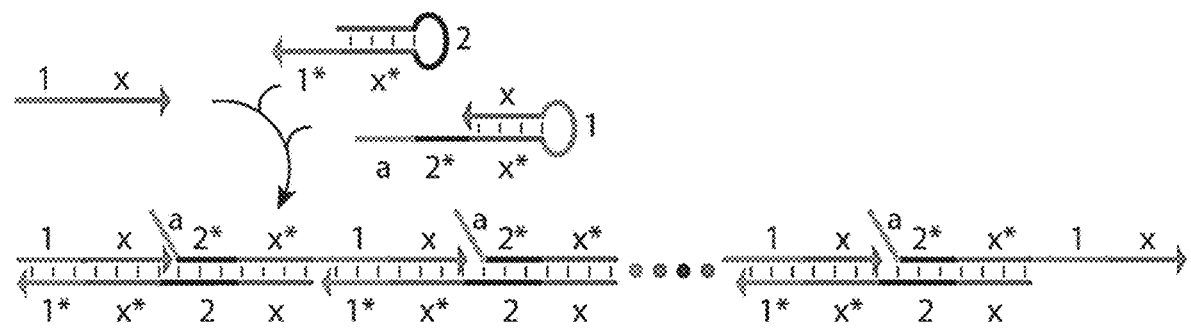
FIGS. 14A-14B are schematics demonstrating the utility of a hybridization chain reaction (HCR) in Co-Zippers.
Figure 14B:
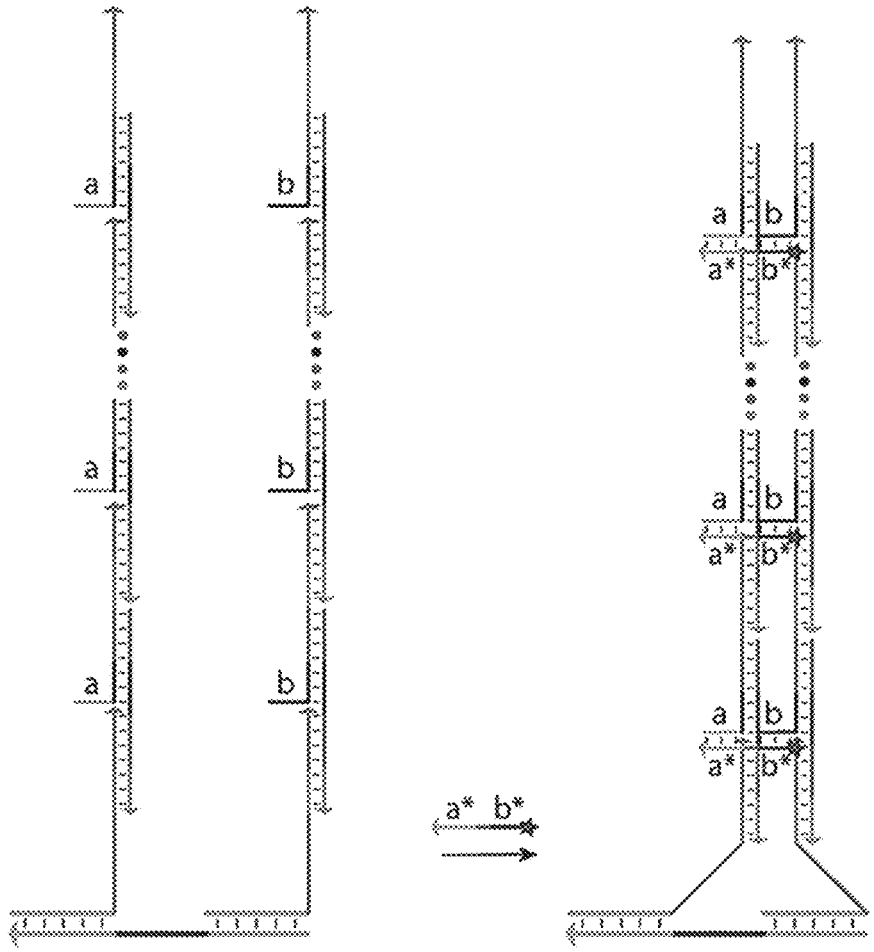

Concatemer strands, as provided herein, may, in some embodiments, be synthesized using a hybridization chain reaction, as shown for example in FIGS. 14A and 14B. Addition of a primer strand of DNA (1+x) to a metastable mixture of two hairpin species triggers a chain reaction of hybridization events where hairpins form a long double-stranded concatemer. In the example in FIGS. 14A and 14B, Single stranded "toehold" domains ('a' and 'b') protruding out of the double-stranded HCR product can maintain stable binding of proximity imager strands only when both are in close proximity to each other. Thus, a composition, in some embodiments, comprises A composition comprising a first primer strand comprising, optionally 5' to 3', domain X*, domain 1, and domain w; a first hairpin strand comprising, optionally 5' to 3', domain w, domain 2, domain w*, and domain 1*; a second hairpin strand comprising, optionally 5' to 3', domain a, domain 2*, domain w*, domain 1, and domain w; a second primer strand comprising, optionally 5' to 3', domain Y*, domain 3, and domain z; a third hairpin strand comprising, optionally 5' to 3', domain z, domain 4, domain z*, and domain 3*; a fourth hairpin strand comprising, optionally 5' to 3', domain b, domain 4*, domain z*, domain 3, and domain z; a labeled imager strand comprising, optionally 5' to 3', domain a* and domain b*; and optionally a polymerase and/or dNTPs, wherein domain X*, domain Y*, domain 1*, domain 2*, domain 3*, domain 4*, domain w*, domain z*, domain a*, and domain b* each comprise a nucleotide sequence complementary to a nucleotide sequence of domain X, domain Y, domain 1, domain 2, domain 3, domain 4, domain w, domain z, domain a, and domain b, respectively, and wherein domain X is located on a first linker strand, and domain Y is optionally located on the first linker strand.

The length of a primer strand may vary. In some embodiments, the length of a primer strand is 3-100 nucleotides. For example, a primer strand may have a length of 3-90, 3-80, 3-70, 3-60, 3-50, 3-40, 3-30, 3-20, 3-10, 4-90, 4-80, 4-70, 4-60, 4-50, 4-40, 4-30, 4-20, 4-10, 5-90, 5-80, 5-70, 5-60, 5-50, 5-40, 5-30, 5-20, 5-10, 10-90, 10-80, 10-70, 10-60, 10-50, 10-40, 10-30, 10-20, 15-90, 15-80, 15-70, 15-60, 15-50, 15-40, 15-30, 15-20, 20-90, 20-80, 20-70, 20-60, 20-50, 20-40, 20-30, 25-90, 25-80, 25-70, 25-60, 25-50, 25-40, or 25-30 nucleotides. In some embodiments, a primer strand has a length of 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides.

The length of a hairpin strand may vary. In some embodiments, the length of a hairpin strand is 20-500 nucleotides. For example, a hairpin strand may have a length of 20-450, 20-400, 20-350, 20-300, 20-250, 20-200, 20-150, 20-100, 20-50, 30-500, 30-450, 30-400, 30-350, 30-300, 30-250, 30-200, 30-150, 30-100, 30-50, 40-500, 40-450, 40-400, 40-350, 40-300, 40-250, 40-200, 40-150, 40-100, 40-50, 50-500, 50-450, 50-400, 50-350, 50-300, 50-250, 50-200, 50-150, 50-100, 50-50, 60-500, 60-450, 60-400, 60-350, 60-300, 60-250, 60-200, 60-150, 60-100, 60-50, 70-500, 70-450, 70-400, 70-350, 70-300, 70-250, 70-200, 70-150, 70-100, 70-50, 80-500, 80-450, 80-400, 80-350, 80-300, 80-250, 80-200, 80-150, 80-100, 80-50, 90-500, 90-450, 90-400, 90-350, 90-300, 90-250, 90-200, 90-150, 90-100, 100-500, 100-450, 100-400, 100-350, 100-300, 100-250, 100-200, or 100-150 nucleotides. In some embodiments, a hairpin strand has a length of 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, or 500 nucleotides.

Co-Zipper Reaction Imager Strands

Figure 11A:
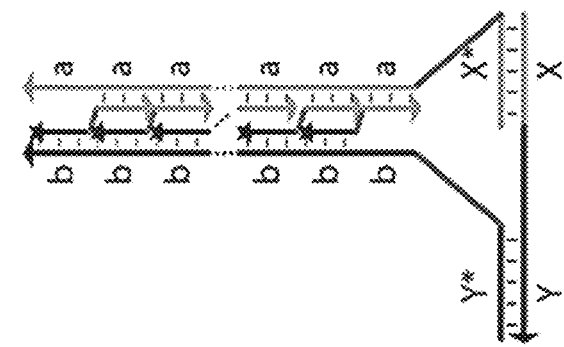
FIGS. 11A-11D provide schematics showing example applications of Co-Zipper.
Figure 11A:
Figure 11A:
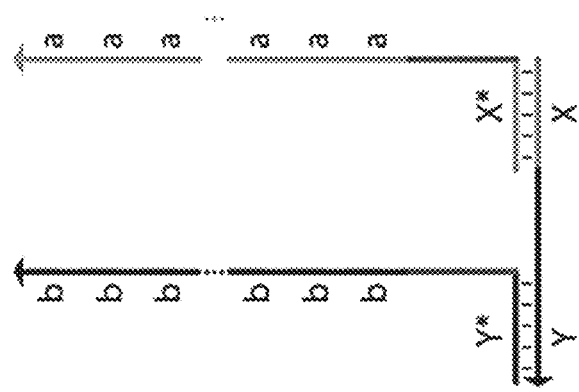
Figure 11A:
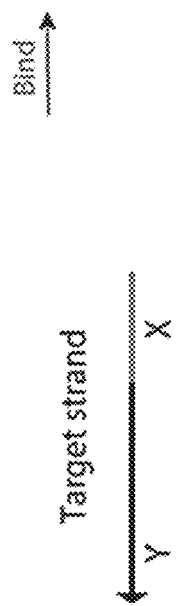

Imager strands, in some embodiments, are short strands that can bind simultaneously to tandem repeat sequences of a first concatemer strand and to tandem repeat sequences of a second concatemer strand (see, e.g., FIG. 11A). In some embodiments, an imager strand comprises a detectable label, such as a fluorophore. The length of an imager strand may vary. In some embodiments, the length of an imager strand is 5-200 nucleotides. In some embodiments, the length of an imager strand is 3-50 nucleotides. For example, an imager strand may have a length of 3-40, 3-30, 3-20, 3-10, 4-50, 4-40, 4-30, 4-20, 4-10, 5-50, 5-40, 5-30, 5-20, 5-10, 10-50, 10-40, 10-30, 10-20, 15-50, 15-40, 15-30, 15-20, 20-50, 20-40, 20-30, 25-50, 25-40, or 25-30 nucleotides. In some embodiments, the length of an imager strand is 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides. In some embodiments, an imager strand comprises a first domain 'b*' and a second domain 'a*' such that the imager strand binds to a first concatemer strand comprising a tandem repeat of domain 'a' and binds to a second concatemer strand comprising a tandem repeat of domain 'b'.

Examples of fluorophores that may be used herein include, without limitation, hydroxycoumarin, methoxycoumarin, Alexa fluor, aminocoumarin, Cy2, FAM, Alexa fluor 405, Alexa fluor 488, Fluorescein FITC, Alexa fluor 430, Alexa fluor 532, HEX, Cy3, TRITC, Alexa fluor 546, Alexa fluor 555, R-phycoerythrin (PE), Rhodamine Red-X, Tamara, Cy3.5 581, Rox, Alexa fluor 568, Red 613, Texas Red, Alexa fluor 594, Alexa fluor 633, Allophycocyanin, Alexa fluor 647, Cy5, Alexa fluor 660, Cy5.5, TruRed, Alexa fluor 680, Cy7 and Cy7.5. Other fluorescent molecules may be used.

In some embodiments, an imager strand (or any other strand described herein) may be labeled (e.g., linked to) a moiety selected from the group consisting of: fluorophores, quantum dots, polymer dots, metal ions, biotin, horseradish peroxidase, tyramide. Other detectable modifier groups are also encompassed herein.

Imager strand may be detected, for example, directly on a concatemer or concatemer-forming strand or may be released via dehybridization (e.g., by modification of the buffer ionic composition or addition of chemicals such as formamide or DMSO, or by application of heat) to be detected by various readout methods appropriate for specific modifications. Detection methods include, without limitation, microscopy, fluorescence scanning, flow cytometry, mass cytometry, mass spectrometry mass-based detection, magnetic methods, aggregate solution based methods (e.g. intercalating dyes like SYBR green), chemical pull-downs, enzymatic assays, and/or sequencing.

Compositions

Co-Zipper compositions of the present disclosure are described by the following numbered paragraphs:

1. A composition comprising: a first target-binding molecule that binds specifically to a first target molecule; a first concatemer strand comprising a first set of tandem repeat sequences, wherein the first concatemer strand can bind to the first target-binding molecule; and a second concatemer strand comprising a second set of tandem repeat sequences, optionally wherein the second concatemer strand can bind to the first target-binding molecule; and a labeled imager strand that can bind simultaneously to tandem repeat sequences of the first concatemer strand and to tandem repeat sequences of the second concatemer strand. See, e.g., FIG. 11B.
2. The composition of paragraph 1, wherein the first target-binding molecule is a polypeptide, optionally wherein the polypeptide is an antibody.
3. The composition of paragraph 1 or 2, wherein the first concatemer strand comprises two or more tandem repeat sequences and/or the second concatemer strand comprises two or more tandem repeat sequences.
4. The composition of any one of paragraphs 1-3, wherein a tandem repeat sequence of the first and/or second concatemer has a length of 20 nucleotides or shorter, or a length of 5 to 15 nucleotides.
5. The composition of any one of paragraphs 1-4, wherein the second concatemer can bind to the first target-binding molecule. See, e.g., FIG. 11B.
6. The composition of any one of paragraphs 1-5, wherein the first concatemer strand and the second concatemer strand bind to the first target-binding molecule through an intermediate linker.
7. The composition of any one of paragraphs 1-6, wherein the first target-binding molecule is linked to a first linker strand comprising a first domain to which the first concatemer strand can bind.
8. The composition of paragraph 7, wherein the first linker strand further comprises a second domain to which the second concatemer strand can bind. See, e.g., FIG. 11B.
9. The composition of paragraph 8, wherein the first domain is separated from the second domain by 1 nm to 10 μm.
10. The composition of paragraph 9, wherein the first domain and/or the second domain has a length of 1 nm to 10 μm.
11. The composition of any one of paragraphs 1-10 further comprising the first target molecule, optionally wherein the target molecule is a DNA, a RNA, or a protein, and optionally wherein the target molecule is present in a fixed tissue.
12. The composition of any one of paragraphs 1-4, wherein the second concatemer strand can bind to a second target-binding molecule. See, e.g., FIG. 11C.
13. The composition of paragraph 12, wherein the second target-binding molecule is linked to a second linker strand comprising a second domain to which the second concatemer strand can bind. See, e.g., FIG. 11C.
14. The composition of any one of paragraphs 7-13, wherein the first linker strand has a length of 1 nm to 10 μm.
15. The composition of paragraph 14 or 15, wherein the second linker strand has a length of 1 nm to 10 μm.
16. The composition of any one of paragraphs 12-15 further comprising the second target-binding molecule.
17. The composition of paragraph 16, wherein the second target-binding molecule binds specifically to the first target molecule, optionally wherein the first and second target-binding molecules bind to different regions of the first target molecule. See, e.g., FIG. 11C.
18. The composition of any one of paragraphs 12-17, wherein the second target-binding molecule is a polypeptide, optionally wherein the polypeptide is an antibody.
19. The composition of any one of paragraphs 1-18, wherein the labeled imager strand comprises a detectable label selected from fluorophores, quantum dots, polymer dots, metal ions, biotin, horseradish peroxidase, magnetic particles, and tyramide.
20. The composition of any one of paragraphs 16-19, wherein the second target-binding molecule binds specifically to a second target molecule, optionally wherein the second target molecule is a DNA, a RNA, or a protein, and optionally wherein the second target molecule is present in a fixed tissue. See, e.g., FIG. 11D.
21. The composition of paragraph 20 further comprising the second target molecule.
22. A composition comprising: a target-binding molecule linked to (i) a first concatemer strand comprising a first set of tandem repeat sequences and (ii) a second concatemer strand comprising a second set of tandem repeat sequences; a labeled imager strand simultaneously bound to tandem repeat sequences of the first concatemer strand and to tandem repeat sequences of the second concatemer strand; and optionally a target bound by the target-binding molecule. See, e.g., FIG. 11B.
23. A composition comprising: a first concatemer strand comprising a first set of tandem repeat sequences; a second concatemer strand comprising a second set of tandem repeat sequences; a labeled imager strand that can bind simultaneously to tandem repeat sequences of the first concatemer strand and to tandem repeat sequences of the second concatemer strand, and optionally a target strand to which the first and second concatemer strands can bind. See, e.g., FIG. 11A.
24. A composition comprising: a first concatemer strand comprising domain X* and tandem repeats of domain a; a second concatemer strand comprising domain Y* and tandem repeats of domain b; and a labeled imager strand comprising domain a* and domain b*, wherein domain X*, domain Y*, domain a*, and domain b* each comprise a nucleotide sequence complementary to a nucleotide sequence of domain X, domain Y, domain a, and domain b, respectively, and wherein domain X is located on a target strand and domain Y is located on a target strand. See, e.g., FIG. 11A.
25. The composition of paragraph 24, wherein domain X and domain Y are located on the same target strand, and optionally wherein domain X and domain Y are separated from each other by a distance of 10 µm or less, or 100 nm or less. See, e.g., FIG. 11B.
26. The composition of paragraph 25, wherein the target strand is linked to a target-binding molecule, optionally wherein the target-binding molecule is a polypeptide, and optionally wherein the polypeptide is an antibody.
27. The composition of paragraph 24, wherein domain X is located on a first target strand and domain Y is located on a second target strand. See, e.g., FIG. 11C.
28. The composition of paragraph 27, wherein the first target strand is linked to a first target-binding molecule and the second target strand is linked to a second target-binding molecule, optionally wherein the first target-binding molecule is a first polypeptide and/or the second target-binding molecule is a second polypeptide, and optionally wherein the first polypeptide is a first antibody and/or the second polypeptide is a second antibody.
29. The composition of paragraph 28, wherein the first polypeptide and the second polypeptide bind specifically to the same target molecule, or wherein the first polypeptide and the second polypeptide bind specifically to different target molecules.
30. A composition comprising a first primer strand comprising, optionally 5' to 3', domain X*, domain 1, and domain w; a first hairpin strand comprising, optionally 5' to 3', domain w, domain 2, domain w*, and domain 1*; a second hairpin strand comprising, optionally 5' to 3', domain a, domain 2*, domain w*, domain 1, and domain w; a second primer strand comprising, optionally 5' to 3', domain Y*, domain 3, and domain z; a third hairpin strand comprising, optionally 5' to 3', domain z, domain 4, domain z*, and domain 3*; a fourth hairpin strand comprising, optionally 5' to 3', domain b, domain 4*, domain z*, domain 3, and domain z; a labeled imager strand comprising, optionally 5' to 3', domain a* and domain b*; and optionally a polymerase and/or dNTPs, wherein domain X*, domain Y*, domain 1*, domain 2*, domain 3*, domain 4*, domain w*, domain z*, domain a*, and domain b* each comprise a nucleotide sequence complementary to a nucleotide sequence of domain X, domain Y, domain 1, domain 2, domain 3, domain 4, domain w, domain z, domain a, and domain b, respectively, and wherein domain X is located on a first linker strand, and domain Y is optionally located on the first linker strand. See, e.g., FIG. 14A.
31. The composition of paragraph 30, wherein the composition further comprises the first linker strand.
32. The composition of paragraph 30 or 31, wherein the first linker strand is linked to a first target-binding molecule that binds specifically to a first target molecule.
33. The composition of paragraph 32, wherein the first target-binding molecule is a first polypeptide, and optionally wherein the first polypeptide is a first antibody.
34. The composition of paragraph 32 or 33, wherein the first target molecule is a DNA, a RNA, or a protein.
35. The composition of any one of paragraphs 30-34, wherein domain Y is located on the first linker strand.
36. The composition of any one of paragraphs 30-35, wherein domain Y is located on a second linker strand.
37. The composition of paragraph 36, wherein the composition further comprises the second linker strand.
38. The composition of paragraph 36 or 37, wherein the second linker strand is linked to a second target-binding molecule.
39. The composition of paragraph 38, wherein the second target-binding molecule binds specifically to the first target molecule.
40. The composition of paragraph 38 or 39, wherein the second target-binding molecule is a second polypeptide, and optionally wherein the second polypeptide is a second antibody.
41. The composition of paragraph 40, wherein the second target-binding molecule binds specifically to a second target molecule.
42. The composition of paragraph 41, wherein the second target molecule is a DNA, a RNA, or a protein.

Methods

Some aspects provide a method of screening for a target molecule, the method comprising contacting a composition suspected of comprising a target molecule with a Co-Zipper composition of the present disclosure, and detecting presence or absence of the labeled imager strand, wherein presence of the labeled imager strand indicates presence of the target molecule.

Other aspects provide a method of detecting a target molecule, the method comprising contacting the target molecule with a Co-Zipper composition of the present disclosure and detecting the labeled imager strand, thereby detecting the target molecule.

Still other aspects provide a method of screening for an interaction between two target molecules, the method comprising contacting a composition suspected of comprising target molecules with the a Co-Zipper composition of the present disclosure, and detecting presence or absence of the labeled imager strand, wherein presence of the labeled imager strand indicates presence of an interaction between the target molecules.

Further aspects provide a method of detecting an interaction between two target molecules, the method comprising contacting a first target molecule and a second target molecule with a Co-Zipper composition of the present disclosure and detecting the labeled imager strand, thereby detecting an interaction between the first target molecule and the second target molecule.

Additional aspects provide a method comprising contacting a target strand with a first concatemer strand comprising a first set of tandem repeat sequences, a second concatemer strand comprising a second set of tandem repeat sequences, and a labeled imager strand that can bind simultaneously to tandem repeat sequences of the first concatemer strand and to tandem repeat sequences of the second concatemer strand, wherein the target strand comprises a first domain to which the first concatemer can bind and a second domain to which the second concatemer can bind, and optionally wherein the first domain is separated from the second domain by 1 nm to 10 µm.

The high specificity and increased signal to background sensitivity of Co-Zipper opens many promising applications. FIGS. 11A-11D show different ways it can utilized to specifically detect DNA, RNA, and protein targets, as well as how it could be used to study interactions such as protein-protein binding in a biomolecular complex. These applications have great potential in fundamental biological research and development of disease diagnostic and medical imaging methods.

Figure 12:
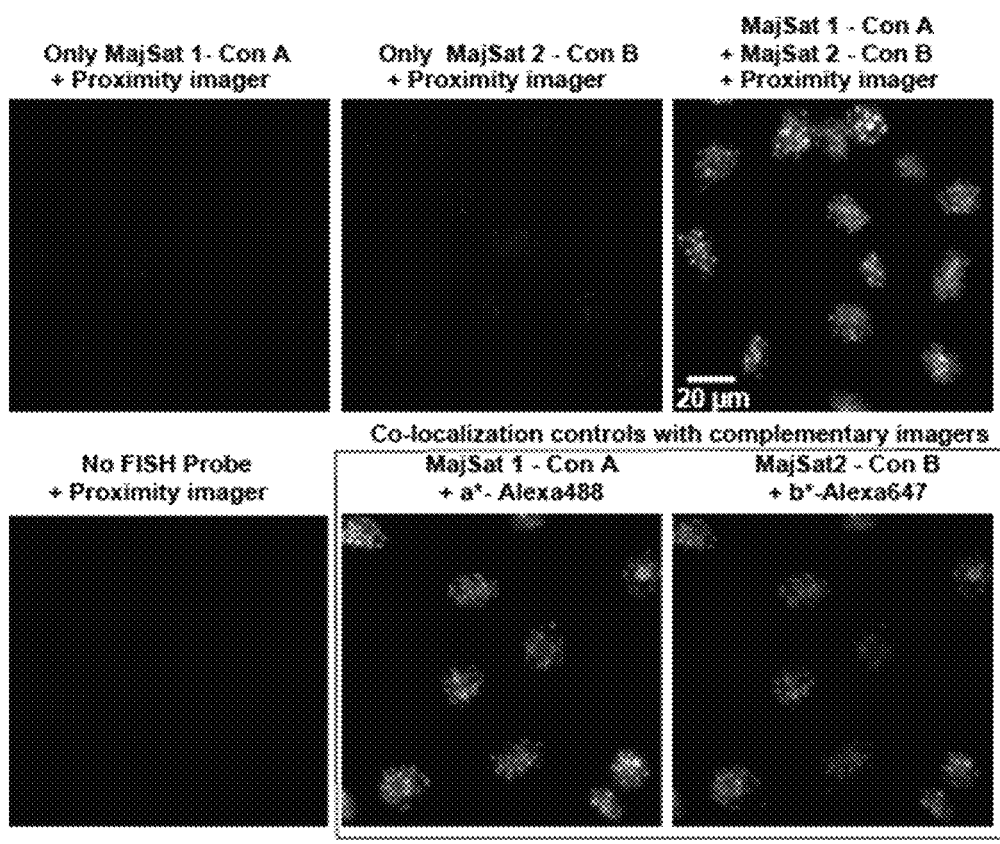
FIG. 12 shows the application of a Co-Zipper for detection of major satellite repeats in mouse embryonic fibroblasts using DNA in situ hybridization probes that target different fragments of the repeat sequence. The left and center images in the top row show negative controls in which only one of the concatemers carrying FISH probes was hybridized, followed by application of the proximity imager. The right image in the top row shows the signal from the proximity imager when both probes were present in close proximity. The bottom row shows a negative control (left image) in which both FISH probes were omitted before addition of the proximity imager and co-localization positive controls (center and right images) and subsequent detection of each concatemer with complementary imagers (as opposed to the imager strand that binds both concatemers).

High-specificity and low-background in situ imaging. Co-Zipper is a valuable method for imaging of targets with high-specificity and low-background. Concatemers generated by PER or rolling circle amplification can be utilized to target DNA/RNA/proteins in situ in a fixed cell or tissue sample. In this case, probes targeting the same target are tagged with different primers (for direct detection) or bridge sequences (for indirect detection) (FIG. 11A). The output is only generated when both concatemers are in close proximity. FIG. 12 shows an example in situ application. FISH probes targeting two repeat sequences in major satellite repeats of mouse embryonic fibroblasts, are appended with PER primers on 3' and are pre-extended into orthogonal concatemers via PER in vitro. These were then used for an in situ hybridization experiment and followed by addition proximity imagers that yield strong signal only when bound to both concatemers, as they are designed to bind the individual concatemers very weakly as shown in the negative controls.

Figure 11B:
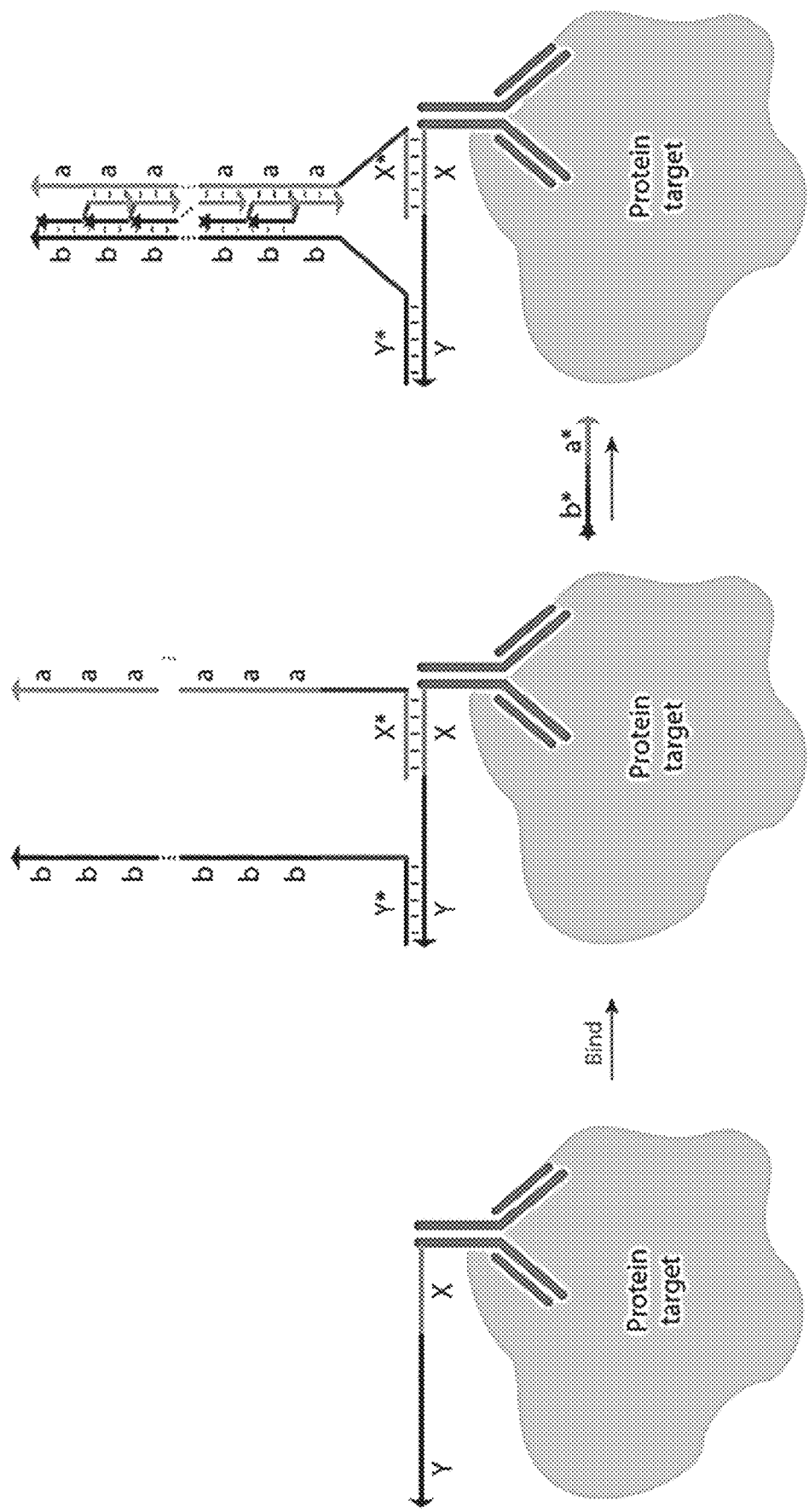
Figure 11C:
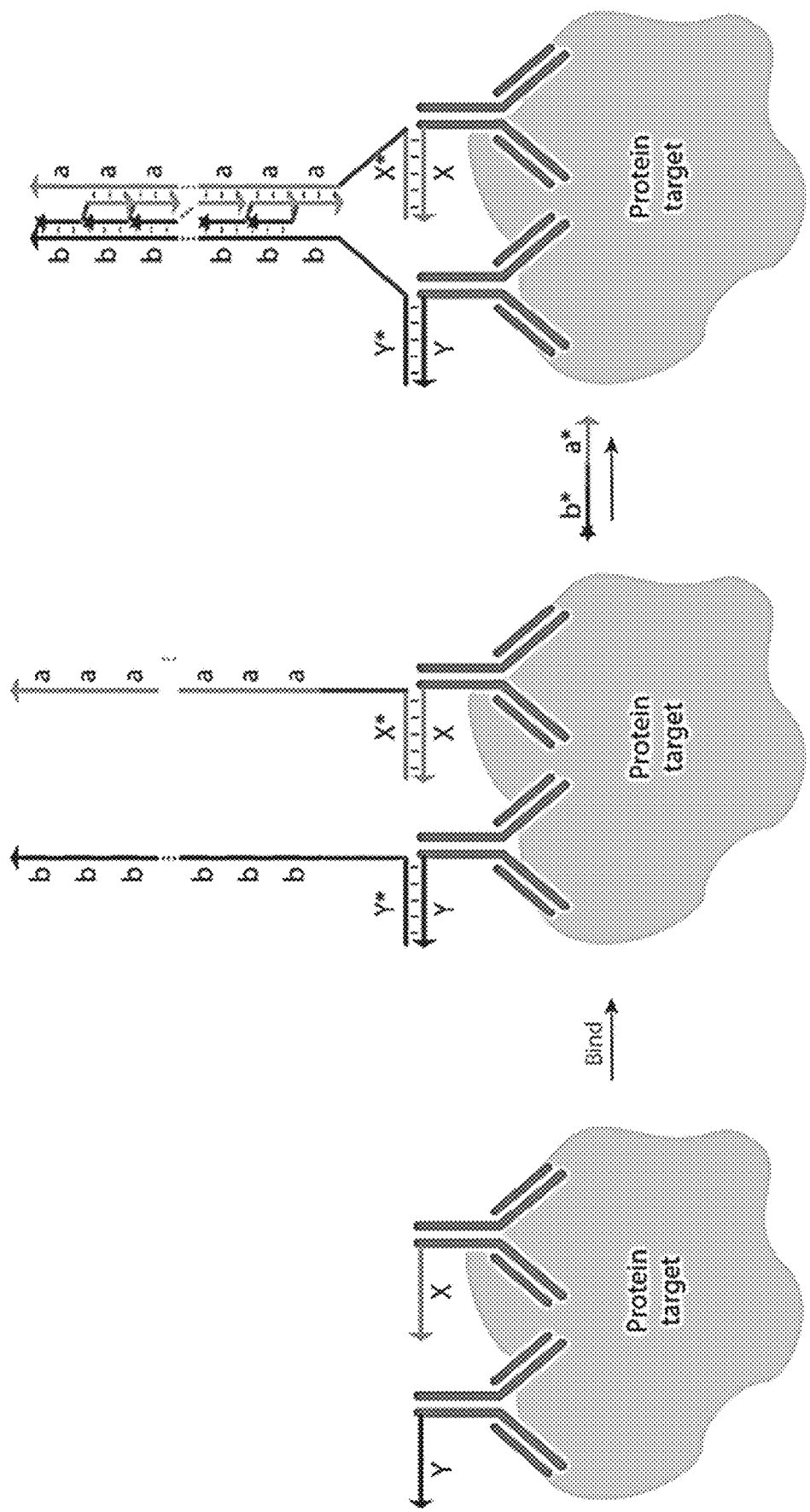
Figure 11D:
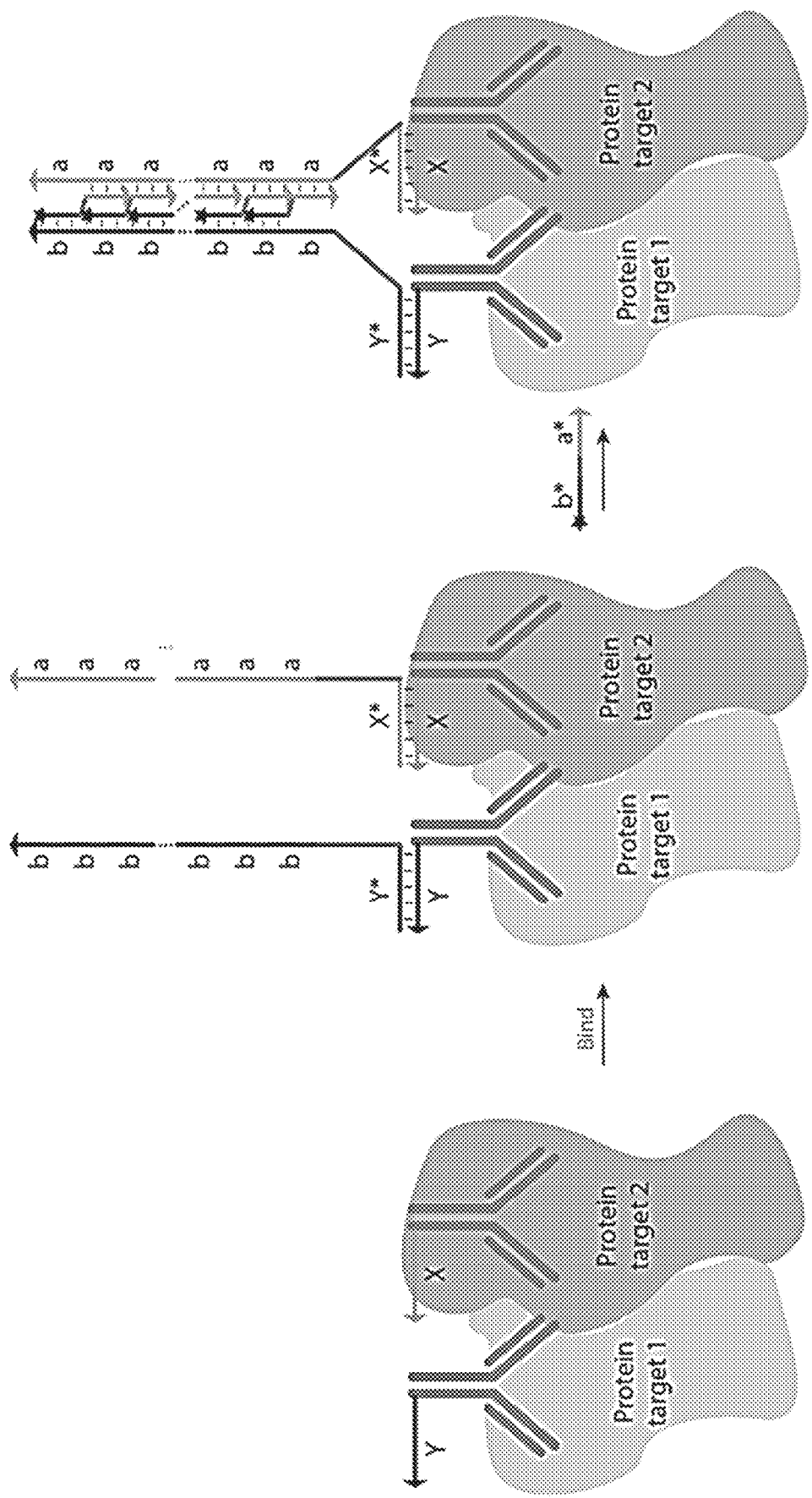
Figure 13:
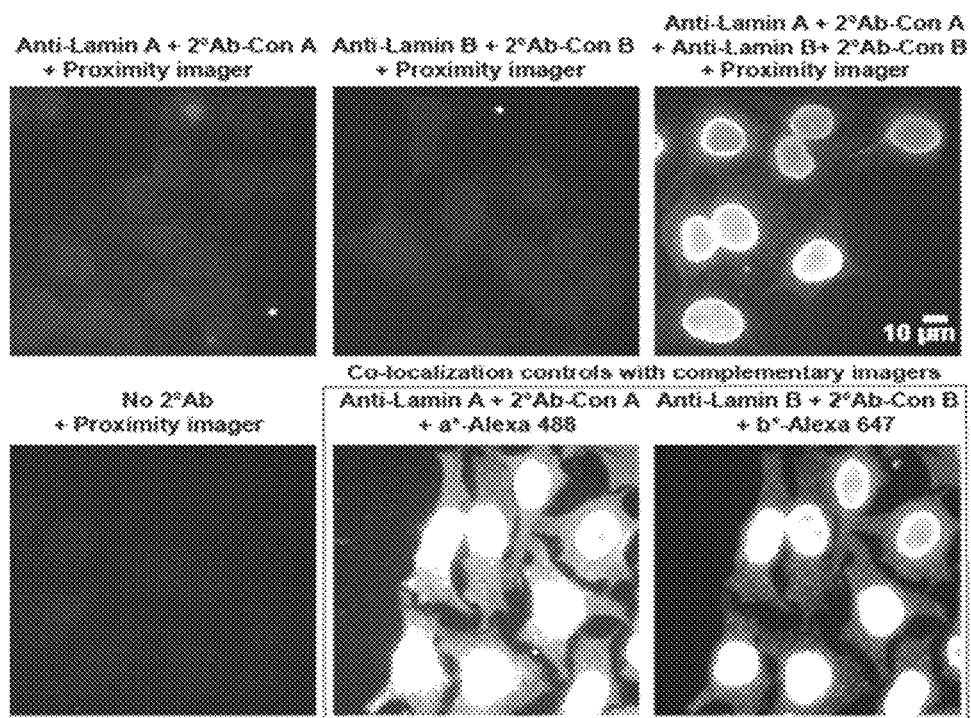
FIG. 13 shows the application of a Co-Zipper for detection of interacting proteins Lamin A and Lamin B using DNA-conjugated mouse and rabbit secondary antibodies on fixed HeLa cells. The left and center images in the top row show negative controls in which only a single antibody was bound, followed by application of the proximity imager. The right image in the top row shows the signal from the proximity imager in the presence of both antibodies. Only nuclear signal is visible due to co-localization of the two targets in the nuclear membrane. The bottom row shows the negative control (left image) in which both secondary antibodies were omitted before addition of the proximity imager and co-localization positive controls (center and right images) and subsequent detection of each concatemer with complementary imagers (as opposed to the imager strand that binds both concatemers).

Interaction partner detection. Co-Zipper can be used for detection of interaction partners in solution or in situ. In this case, the concatemers are tagged onto different molecules of interest either directly or through use of complementary bridge sequences (FIG. 11D). The output is only generated when both concatemers are in close proximity. FIG. 13 shows an example in situ application. Two nuclear lamina proteins Lamin A and B were probed by primary antibodies against them followed by cognate secondary antibodies conjugated to two orthogonal bridge sequences. Two orthogonal primers appended with bridge complements were pre-extended into concatemers via PER in vitro. After immunostaining the concatemers were simultaneously applied onto the samples and hybridized onto the bridges. This was followed by addition of the proximity imager, which revealed the positions where both proteins are colocalized (i.e. nuclear lamina), and gave no signal when one of the antibodies were omitted. The controls where imagers that bind stably to individual concatemers show significant staining in the cytoplasm in comparison to the very specific nuclear signal obtained by the proximity imager.

Multiplexed detection. Co-Zipper enables easy multiplexing through use of orthogonal concatemers. Multiplexing can be done by combining a unique concatemer with a universal concatemer for each target or pair. Alternatively it also makes it possible to reach a higher level of multiplexing with a lower number of orthogonal sequence designs through the combinatorial detection system that can be utilized by the proximity imagers. This allows reaching $n*(n-1)/2$ orthogonal binary systems, by using n orthogonal concatemers. Also, an alternative site can be used for detection of the proximity probe.

Highly specific and sensitive biomarker detection. Co-Zipper can be used for in solution and in situ diagnostic applications. Rapid, specific, and sensitive detection capability it offers enables high-confidence in situ imaging of low abundance biomarkers in tissue samples which are typically difficult to image due to high background and low signal.

Exemplary Co-Zipper Features

Specific detection: Because the detection of target(s) rely on the successful binding of fluorescent probes to different concatemers, the specificity of detection is increased compared to methods that only have one detection event specific to the target. This coincidence detection reduces the background in a non-linear fashion.

Multiple proximity checks: The proximity of the two concatemers is checked at every step of fluorescent probe hybridization, since each hybridization step relies on the proximity of the two concatemers, so the signal amplification level reflects physical proximity. Thus, the detection becomes extremely specific, resulting in amplified signal only for proximal concatemers.

Amplified signal: Concatemers provide robust signal amplification at targets detected with high accuracy.

Other Embodiments

In some embodiments, Co-Zipper assays can be performed in solution, on immobilized surfaces and substrates, in sandwich form or in situ. They could be used to detect proteins, RNA, DNA, as well as other biomarkers, analytes, small molecules, viruses, whole cells or cell fragments or any other target can be tagged with nucleic acid probes directly or indirectly (using secondary probes). The probes to be used for specific tagging could be antibodies, nanobodies, or other affinity binders such as affibodies or aptamers, RNA or DNA in situ hybridization probes, ligands, recombinant tags, unnatural amino acids or nucleotides or small molecules.

In some embodiments, instead of concatemers of tandem repeats as in the case of PER or RCA, DNA tags with interspersed repeats or unique sequences could be employed for labeling and can be detected by proximity imagers. In this case more than one proximity imager can be designed to bind the concatemers simultaneously.

In some embodiments, instead of single stranded concatemers single or double stranded branched DNA structures or double stranded DNA-assemblies can be employed. Such structures can, for example, be prepared by hybridization chain reaction (HCR) [11] with addition of a toehold domain on one of the hairpins (FIG. 14A). In this case, single stranded toehold domains can be left to protrude from each of the structures, which can maintain stable binding of proximity imagers only when they are in close proximity, but not by themselves (FIG. 14B).

In some embodiments, concatemer length and hybridization length of the proximity imager can be modified depending on the experimental conditions and desired application. Changes the hybridization length or buffer conditions or temperature can be performed to modulate the binding time. The binding of complementary regions a/a* and b/b* on the concatemers and proximity imager may be transient (such that the average dwell time is on the order of minutes or less), or they may be bound more strongly (e.g. bound time of minutes to hours or more). Short binding times could be utilized for specific yet transient hybridization of the proximity imagers to enable repeated sampling or single-molecule detection experiments and high-resolution imaging.

In some embodiments, in addition to changing binding buffer conditions, temperature or hybridization length, the interaction between proximity imager and concatemers could also be more specifically controlled through the use of a protection strand and toehold-mediated strand displacing [9] or toehold exchange [10] that requires the proximity imager to compete with an existing strand.

In some embodiments, multiple targets can be simultaneously detected through use of multiple orthogonal sequences in concatemers. Multiplexing can be achieved spectrally (via use of proximity imagers with different fluorophores) or sequentially. Sequential detection is enabled by programmable removal of proximity imagers by adjusting simple wash conditions. Removal can be enabled by changes in salt concentration, formamide amount, changing the temperature, or enzymatic cleavage. Multiple targets can also be sequentially detected in pairwise manner by proximity imager sequences programmed to detect different pairs in each round.

In some embodiments, multi-way interaction detection: In addition to detection of pairwise interactions, Co-Zipper can be modified to detect multi-way interactions. This can be achieved by altering the design to enable proximity probe to bind stable only when multiple concatemers are in close proximity.

In some embodiments, target, concatemer, probe (e.g. antibody) and other components (bridges, splints etc.) may be annealed together, or they may be combined together isothermally (e.g. at room temperature, 37° C., 46° C., etc.). They may be also bound under conditions that improve their specificity to the target strand, such as using standard ISH (In Situ Hybridization) buffers like SSCT and PBS, often with the addition of formamide. This binding may be done diffusively (in solution), or with one or more of the components attached to a substrate. For example, one of the concatemers (with or without the target) might be bound to the surface, with the other one subsequently hybridized to the splint or to the same or different target.

In some embodiments, concatemers can be detected with proximity imagers diffusively in solution mixed with targets, or under immobilized onto surfaces (beads, paper, hydrogels, glass, plastic, nanoparticles) or applied onto targets in situ.

In some embodiments, the concatemers themselves may be directly conjugated to the antibodies or other probes (i.e. no intermediate bridge strand) or the primers on the probes can be extended into concatemer in advance of, simultaneously, or after labeling.

In some embodiments, additional sequence modifications, such as spacers may be included in proximity imager to modulate the reach distance under different configurations.

In some embodiments, fluorescent readout can also be achieved by using fluorophore-labeled dNTPs that are incorporated during the extension reaction, so that the concatemers themselves are fluorescent. In this case FRET between the fluorophores on proximal concatemers could be used as output [FRET1]. A similar approach can be applied to double stranded structures as in the case of HCR.

Target-Binding Molecules

In some embodiments, a strand (e.g., catalytic strand, concatemer-forming strand, and/or concatemer strand) can bind to (or binds to) a target-binding molecule. A target-binding molecule may any biomolecule, such as a polypeptide or a polynucleotide. In some embodiments, a target-binding molecule is a polypeptide. In some embodiments, a target-binding molecule is a protein (e.g., full-length protein or peptide). In some embodiments, a target-binding molecule is an antibody, such as a monoclonal antibody. The term "antibody" encompasses whole antibodies and antibody fragments (e.g., scFvs).

The binding interaction between a target-binding molecule and a target molecule may be transient (e.g., average dwell time on the order of minutes or less), or the molecules may be bound more stably or strongly (e.g., average dwell time on the order of minutes to hours or more). In some embodiments, the average dwell time between a target-binding molecule and a target molecule is 1 to 10 nanoseconds, 1 to 50 nanoseconds, 25 to 100 nanoseconds, 50 to 250 nanoseconds, or 250 to 1000 nanoseconds. In some embodiments, the average dwell time between a target-binding molecule and a target molecule is 1 to 10 seconds, 1 to 50 seconds, 25 to 100 seconds, 50 to 250 seconds, or 250 to 1000 seconds. In some embodiments, the average dwell time between a target-binding molecule and a target molecule is 1 to 10 minutes, 1 to 50 minutes, 25 to 100 minutes, 50 to 250 minutes, or 250 to 1000 minutes. In some embodiments, the average dwell time between a target-binding molecule and a target molecule is 1 to 10 hours, 1 to 50 hours, 25 to 100 hours, 50 to 250 hours, or 250 to 1000 hours. In some embodiments, the binding affinity between a target-binding molecule and a target molecule is 5 nM to 1000 nM, 5 nM to 500 nM, 250 nM to 750 nM, 500 nM to 1000 nM, 1 to 100 μM, 1 to 50 μM, 1 to 25 μM, 1 to 10 μM, or 1 to 5 μM. In addition to changing binding buffer conditions, the binding affinity and/or dwell time can be altered through the use of a protection strand and toehold-mediated strand displacing [5] or toehold exchange [6] that requires the target strand to compete with an existing strand.

Linker Strands

In some embodiments, a strand (e.g., catalytic strand, concatemer-forming strand, and/or concatemer strand) can bind to a target-binding molecule directly or indirectly through in intermediate linker. In some embodiments, the intermediate linker is a linker strand (e.g., a single-stranded nucleic acid). A linker strand, in some embodiments, comprises domains to which a strand can bind. In some embodiments, a linker strand comprises domain 'X'. In some embodiments, a linker strand comprises domain 'Y'. In some embodiments, a linker strand comprises domain 'X' and domain 'Y'.

The length of a linker strand may vary. In some embodiments, the length of a linker strand is 1-10000 nucleotides, or 1 nm-10 μm. In some embodiments, the length of a linker strand is 10-100 nucleotides. For example, a linker strand may have a length of 10-90, 10-80, 10-70, 10-60, 10-50, 10-40, 10-30, 10-20, 15-90, 15-80, 15-70, 15-60, 15-50, 15-40, 15-30, 15-20, 20-90, 20-80, 20-70, 20-60, 20-50, 20-40, 20-30, 25-90, 25-80, 25-70, 25-60, 25-50, 25-40, or 25-30 nucleotides. In some embodiments, a linker strand has a length of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides. In some embodiments, a linker strand (e.g., a first and/or second linker strand) has a length of fewer than 100 nucleotides, fewer than 50 nucleotides, or 20 to 50 nucleotides.

The length of a domain (domain 'X' and/or domain 'Y') of a linker strand may vary. In some embodiments, the length of a domain of a linker strand is 3-100 nucleotides. For example, a domain of a linker strand may have a length of 3-90, 3-80, 3-70, 3-60, 3-50, 3-40, 3-30, 3-20, 3-10, 4-90, 4-80, 4-70, 4-60, 4-50, 4-40, 4-30, 4-20, 4-10, 5-90, 5-80, 5-70, 5-60, 5-50, 5-40, 5-30, 5-20, 5-10, 10-90, 10-80, 10-70, 10-60, 10-50, 10-40, 10-30, 10-20, 15-90, 15-80, 15-70, 15-60, 15-50, 15-40, 15-30, 15-20, 20-90, 20-80, 20-70, 20-60, 20-50, 20-40, 20-30, 25-90, 25-80, 25-70, 25-60, 25-50, 25-40, or 25-30 nucleotides. In some embodiments, a domain of a linker strand has a length of 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides. In some embodiments, a domain has a length of 20 nucleotides or shorter, or a length of 5 to 15 nucleotides.

The distance between two domains (e.g., between domain 'X' and domain 'Y') of a linker strand, in some embodiments, is 1-10000 nucleotides, or 1 nm-10 μm. The distance between two domains (e.g., between domain 'X' and domain 'Y') of a linker strand, in some embodiments, is fewer than 50 nucleotides. For example, one domain (e.g., domain 'X') may be separated from another domain (e.g., domain 'Y') by 0-50, 0-40, 0-30, 0-20, 0-10, 1-50, 1-40, 1-30, 1-20, 1-10, 2-50, 2-40, 2-30, 2-20, 2-10, 3-50, 3-40, 3-30, 3-20, 3-10, 4-50, 4-40, 4-30, 4-20, 4-10, 5-50, 5-40, 5-30, 5-20, or 5-10 nucleotides. In some embodiments, one domain (e.g., domain 'X') may be separated from another domain (e.g., domain 'Y') by 0, 1, 2, 3, 4, 5, 6, 7, 8, 9, 10, 11, 12, 13, 14, 15, 16, 17, 18, 19, or 20 nucleotides. In some embodiments, one domain (e.g., domain 'X') is separated from another domain (e.g., domain 'Y') by fewer than 25 nucleotides, or 5 to 15 nucleotides.

Target Molecules

A target molecule (e.g., a first target molecule or a second target molecule) may be any biomolecule (e.g., biomarker), such as a DNA, a RNA, or a protein (e.g., antibody, nanobody, aptamer, peptide tag, or other probe molecule). Other examples of target molecules include lipids, small molecules, and molecular chimeras. In some embodiments, a target molecule (or a target-binding molecule) is present in a fixed tissue. In some embodiments, a target molecule (or a target-binding molecule) is present in a solution, such as an aqueous buffer. In some embodiments, a target molecule (or a target-binding molecule) is attached to a surface (e.g., glass, paper, nitrocellulose, mica, etc.). In some embodiments, a target molecule is part of a biomolecular complex. In some embodiments, a target molecule is a diagnostic target molecule and/or a therapeutic target molecule.

The examples included in this disclosure depicting detection of nucleic acid targets and antibody targets are for the purpose of illustration and are not intended to be limiting. Examples of target molecules include, without limitation, proteins, saccharides (e.g., polysaccharides), lipids, nucleic acids (e.g., DNA, RNA, microRNAs), and small molecules. Targets may be DNA or RNA. In some embodiments, a molecular target is a biomolecule. As used herein, a "biomolecule" is any molecule that is produced by a living organism, including large macromolecules such as proteins, polysaccharides, lipids and nucleic acids (e.g., DNA and RNA such as mRNA), as well as small molecules such as primary metabolites, secondary metabolites, and natural products. Examples of molecular targets, specifically biomolecules, include, without limitation, DNA, RNA, cDNA, or the DNA product of RNA subjected to reverse transcription.

In some embodiments, a target molecule is a protein target such as, for example, proteins of a cellular environment (e.g., intracellular or membrane proteins). Examples of proteins include, without limitation, fibrous proteins such as cytoskeletal proteins (e.g., actin, arp2/3, coronin, dystrophin, FtsZ, keratin, myosin, nebulin, spectrin, tau, titin, tropomyosin, tubulin and collagen) and extracellular matrix proteins (e.g., collagen, elastin, f-spondin, pikachurin, and fibronectin); globular proteins such as plasma proteins (e.g., serum amyloid P component and serum albumin), coagulation factors (e.g., complement proteins, C1-inhibitor and C3-convertase, Factor VIII, Factor XIII, fibrin, Protein C, Protein S, Protein Z, Protein Z-related protease inhibitor, thrombin, Von Willebrand Factor) and acute phase proteins such as C-reactive protein; hemoproteins; cell adhesion proteins (e.g., cadherin, ependymin, integrin, Ncam and selectin); transmembrane transport proteins (e.g., CFTR, glycophorin D and scramblase) such as ion channels (e.g., ligand-gated ion channels such nicotinic acetylcholine receptors and GABAa receptors, and voltage-gated ion channels such as potassium, calcium and sodium channels), synport/antiport proteins (e.g., glucose transporter); hormones and growth factors (e.g., epidermal growth factor (EGF), fibroblast growth factor (FGF), vascular endothelial growth factor (VEGF), peptide hormones such as insulin, insulin-like growth factor and oxytocin, and steroid hormones such as androgens, estrogens and progesterones); receptors such as transmembrane receptors (e.g., G-protein-coupled receptor, rhodopsin) and intracellular receptors (e.g., estrogen receptor); DNA-binding proteins (e.g., histones, protamines, CI protein); transcription regulators (e.g., c-myc, FOXP2, FOXP3, MyoD and P53); immune system proteins (e.g., immunoglobulins, major histocompatibility antigens and T cell receptors); nutrient storage/transport proteins (e.g., ferritin); chaperone proteins; and enzymes.

In some embodiments, a target molecule (or a target-binding molecule, discussed above) is an antibody. As used herein, the term "antibody" includes full-length antibodies and any antigen binding fragment (e.g., "antigen-binding portion") or single chain thereof. The term "antibody" includes, without limitation, a glycoprotein comprising at least two heavy (H) chains and two light (L) chains interconnected by disulfide bonds, or an antigen binding portion thereof. Antibodies may be polyclonal or monoclonal; xenogeneic, allogeneic, or syngeneic; or modified forms thereof (e.g., humanized, chimeric). As used herein, "antigen-binding portion" of an antibody, refers to one or more fragments of an antibody that retain the ability to specifically bind to an antigen. The antigen-binding function of an antibody can be performed by fragments of a full-length antibody. Examples of binding fragments encompassed within the term "antigen-binding portion" of an antibody include (i) a Fab fragment, a monovalent fragment consisting of the VH, VL, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VH and VL domains of a single arm of an antibody, (v) a dAb fragment (Ward et al., Nature 341:544 546, 1989), which consists of a VH domain; and (vi) an isolated complementarity determining region (CDR) or (vii) a combination of two or more isolated CDRs, which may optionally be joined by a synthetic linker. Furthermore, although the two domains of the Fv fragment, VH and VL, are coded for by separate genes, they can be joined, using recombinant methods, by a synthetic linker that enables them to be made as a single protein chain in which the VH and VL regions pair to form monovalent molecules (known as single chain Fv (scFv); see, e.g., Bird et al. Science 242:423 426, 1988; and Huston et al. Proc. Natl. Acad. Sci. USA 85:5879-5883, 1988). Such single chain antibodies are also encompassed within the term "antigen-binding portion" of an antibody. These antibody fragments are obtained using conventional techniques known to those with skill in the art, and the fragments are screened for utility in the same manner as are intact antibodies.

In some embodiments, a target molecule is present in a tissue sample, optionally a fixed tissue. In some embodiments, a tissue may be treated with a mild fixation reagent or under mild fixation conditions (i.e., a reagent or conditions that preserve a tissue). In some embodiments, a target molecule is present in a solution, e.g., an aqueous solution. In some embodiments, a target molecule is attached to a solid support or solid surface.

The compositions and methods of the present disclosure may be used to detect a single target molecule or multiple target molecules, e.g., multiple target molecules that belong to the same molecular complex. In some embodiments, multiple target molecules may be multiple proteins that belong the same protein complex, e.g., multiple proteins that belong to the Mediator complex or any other transcriptional complex. In some embodiments, multiple target molecules may be multiple antibodies in a mixture, e.g., two or more distinct antibodies in a mixture.

In some embodiments, two or more targets are detected using any of the method provided herein. In some embodiments, the number of targets detected in a single reaction may be increased by increasing the number of catalytic molecules capable of binding directly or indirectly to a target molecule. In some embodiments, at least 2, 3, 4, 5, 10, 15, 20, 30, 40, 50, 60, 70, 80, 90, or 100 different target molecules are detected in a single reaction. In some embodiments, 1-5, 1-10, 1-20, 1-50, or 1-100 different target molecules are detected in a single reaction.

The distance between any two targets (or between two domains or sequences of a target or linker strand) may be 1 nm-10 µm. For example, the distance between any two molecules or domains detected may be 1 nm-100 nm, 1 nm-500 nm, 1 nm-1 µm, or 1 nm-5 µm.

Target Strands

In some embodiments, a strand (e.g., catalytic strand, concatemer-forming strand, and/or concatemer strand) can bind directly to a target strand (e.g., a DNA or RNA). A target strand, in some embodiments, comprises sequences (domains) of interest to which a strand is designed to bind. In some embodiments, a target strand comprises domain 'X' (e.g., comprising a first sequence of interest). In some embodiments, a target strand comprises domain 'Y' (e.g., comprising a second sequence of interest). In some embodiments, a target strand comprises domain 'X' and domain 'Y'.

The length of a domain (domain 'X' and/or domain 'Y') of a target strand may vary. In some embodiments, the length of a target strand is 1-10000 nucleotides, or 1 nm-10 µm. In some embodiments, the length of a domain of a target strand is 3-100 nucleotides. For example, a domain of a target strand may have a length of 3-90, 3-80, 3-70, 3-60, 3-50, 3-40, 3-30, 3-20, 3-10, 4-90, 4-80, 4-70, 4-60, 4-50, 4-40, 4-30, 4-20, 4-10, 5-90, 5-80, 5-70, 5-60, 5-50, 5-40, 5-30, 5-20, 5-10, 10-90, 10-80, 10-70, 10-60, 10-50, 10-40, 10-30, 10-20, 15-90, 15-80, 15-70, 15-60, 15-50, 15-40, 15-30, 15-20, 20-90, 20-80, 20-70, 20-60, 20-50, 20-40, 20-30, 25-90, 25-80, 25-70, 25-60, 25-50, 25-40, or 25-30 nucleotides. In some embodiments, a domain of a target strand has a length of 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides. In some embodiments, a domain has a length of 20 nucleotides or shorter, or a length of 5 to 15 nucleotides.

The distance between two domains (e.g., between domain 'X' and domain 'Y') of a linker strand, in some embodiments, is 1-10000 nucleotides, or 1 nm-10 µm. The distance between two domains (e.g., between domain 'X' and domain 'Y') of a target strand, in some embodiments, is fewer than 50 nucleotides. For example, one domain (e.g., domain 'X') may be separated from another domain (e.g., domain 'Y') by 0-50, 0-40, 0-30, 0-20, 0-10, 1-50, 1-40, 1-30, 1-20, 1-10, 2-50, 2-40, 2-30, 2-20, 2-10, 3-50, 3-40, 3-30, 3-20, 3-10, 4-50, 4-40, 4-30, 4-20, 4-10, 5-50, 5-40, 5-30, 5-20, or 5-10 nucleotides. In some embodiments, one domain (e.g., domain 'X') may be separated from another domain (e.g., domain 'Y') by 0, 1, 2, 3, 4, 5, 6, 7, 8, 9, 10, 11, 12, 13, 14, 15, 16, 17, 18, 19, or 20 nucleotides. In some embodiments, one domain (e.g., domain 'X') is separated from another domain (e.g., domain 'Y') by fewer than 25 nucleotides, or 5 to 15 nucleotides.

Nucleic Acids

It should be understood that the nucleic acids of the present disclosure do not occur in nature. Thus, the nucleic acids may be referred to as "engineered nucleic acids." An "engineered nucleic acid" is a nucleic acid (e.g., at least two nucleotides covalently linked together, and in some instances, containing phosphodiester bonds, referred to as a phosphodiester "backbone") that does not occur in nature. Engineered nucleic acids include recombinant nucleic acids and synthetic nucleic acids. A "recombinant nucleic acid" is a molecule that is constructed by joining nucleic acids (e.g., isolated nucleic acids, synthetic nucleic acids or a combination thereof) and, in some embodiments, can replicate in a living cell. A "synthetic nucleic acid" is a molecule that is amplified or chemically, or by other means, synthesized. A synthetic nucleic acid includes those that are chemically modified, or otherwise modified, but can base pair with (also referred to as "binding to," e.g., transiently or stably) naturally-occurring nucleic acid molecules. Recombinant and synthetic nucleic acids also include those molecules that result from the replication of either of the foregoing.

As used herein, the term "complementary" refers to the ability of two nucleotides or two sets of nucleotides to precisely pair/bind to one another. For example, if a single nucleotide of a first sequence or strand is capable of hydrogen bonding with a nucleotide at the corresponding position of second sequence or strand, then the bases are considered to be complementary to each other at that position. Nucleobase pairings may include both canonical Watson-Crick base pairing and non-Watson-Crick base pairing.

While an engineered nucleic acid, as a whole, is not naturally-occurring, it may include wild-type nucleotide sequences. In some embodiments, an engineered nucleic acid comprises nucleotide sequences obtained from different organisms (e.g., obtained from different species). For example, in some embodiments, an engineered nucleic acid includes a murine nucleotide sequence, a bacterial nucleotide sequence, a human nucleotide sequence, a viral nucleotide sequence, or a combination of any two or more of the foregoing sequences. In some embodiments, an engineered nucleic acid contain one or more random bases.

In some embodiments, an engineered nucleic acid of the present disclosure may comprise a backbone other than a phosphodiester backbone. For example, an engineered nucleic acid, in some embodiments, may comprise phosphoramide, phosphorothioate, phosphorodithioate, O-methylphophoroamidite linkages, peptide nucleic acids or a combination of any two or more of the foregoing linkages. An engineered nucleic acid may be single-stranded (ss) or double-stranded (ds), as specified, or an engineered nucleic acid may contain portions of both single-stranded and double-stranded sequence. In some embodiments, an engineered nucleic acid contains portions of triple-stranded sequence, or other non-Watson-Crick base pairing such as G-quartets, G-quadruplexes, and i-motifs. An engineered nucleic acid may comprise DNA (e.g., genomic DNA, cDNA or a combination of genomic DNA and cDNA), RNA or a hybrid molecule, for example, where the nucleic acid contains any combination of deoxyribonucleotides and ribonucleotides (e.g., artificial or natural), and any combination of two or more bases, including uracil, adenine, thymine, cytosine, guanine, inosine, xanthine, hypoxanthine, isocytosine and isoguanine.

Engineered nucleic acids of the present disclosure may be produced using standard molecular biology methods (see, e.g., Green and Sambrook, *Molecular Cloning*, A Laboratory Manual, 2012, Cold Spring Harbor Press). In some embodiments, nucleic acids are produced using GIBSON ASSEMBLY® Cloning (see, e.g., Gibson, D. G. et al. *Nature Methods*, 343-345, 2009; and Gibson, D. G. et al. *Nature Methods*, 901-903, 2010, each of which is incorporated by reference herein). GIBSON ASSEMBLY® typically uses three enzymatic activities in a single-tube reaction: 5' exonuclease, the 3' extension activity of a DNA polymerase and DNA ligase activity. The 5' exonuclease activity chews back the 5' end sequences and exposes the complementary sequence for annealing. The polymerase activity then fills in the gaps on the annealed domains. A DNA ligase then seals the nick and covalently links the DNA fragments together. The overlapping sequence of adjoining fragments is much longer than those used in Golden Gate Assembly, and therefore results in a higher percentage of correct assemblies. Other methods of producing engineered nucleic acids are known in the art and may be used in accordance with the present disclosure.

Additional Reaction Components and Conditions

In some embodiments, a composition comprises and/or a method makes use of a polymerase, such as a strand displacing polymerase. In some embodiments, the polymerase is a DNA polymerase (DNAP), such as a DNA polymerase having DNA strand displacement activity (a strand displacing polymerase). "Strand displacement" describes the ability to displace downstream DNA encountered during synthesis. Examples of polymerases having DNA strand displacement activity that may be used as provided herein include, without limitation, phi29 DNA polymerase (e.g., NEB #M0269), Bst DNA polymerase, large fragment (e.g., NEB #M0275), or Bsu DNA polymerase, large fragment (e.g., NEB #M0330). Other polymerases having strand displacement activity may be used. In some embodiments, the polymerase is a RNA polymerase.

In some embodiments, the polymerase is phi29 DNA polymerase. In such embodiments, the reaction conditions may be as follows: 1× reaction buffer (e.g., 50 mM Tris-HCl, 10 mM MgCl$_2$, 10 mM (NH$_4$)$_2$SO$_4$, 4 mM DTT) supplement with purified bovine serum albumin (BSA), pH 7.5, incubated at 30° C.

In some embodiments, the polymerase is Bst DNA polymerase, large fragment. In such embodiments, the reaction conditions may be as follows: 1× reaction buffer (e.g., 20 mM Tris-HCl, 10 mM (NH$_4$)$_2$SO$_4$, 10 mM KCl, 2 mM MgSO$_4$, 0.1% TRITON® X-100), pH 8.8, incubated at 65° C.

In some embodiments, the polymerase is Bsu DNA polymerase. In such embodiments, the reaction conditions may be as follows: 1× reaction buffer (e.g., 50 mM NaCl, 10 mM Tris-HCl, 10 mM MgCl$_2$, 1 mM DTT), pH 7.9, incubated at 37° C.

The concentration of particular strands and dNTPs in a primer exchange reaction composition or system may be varied depending, for example, on the particular application and kinetics required for that particular application.

The concentration of strand in a reaction described herein may be, for example, 5 nM to 1000 nM. In some embodiments, the strand concentration in a reaction described herein is 5-10, 5-20, 5-30, 5-40, 5-50, 5-60, 5-70, 5-80, 5-90, 5-100, 5-125, 5-150, 5-200, 10-50, 10-75, 10-100, 10-150, 10-200, 25-75, 25-100, 25-125 or 25-200 nM. In some embodiments, the strand concentration in a reaction is 10-200, 10-300, 10-400, 10-500, 10-600, 10-70, 10-800, 10-900 or 10-100 nM. In some embodiments, the strand concentration in a reaction is 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195 or 200 nM. In some embodiments, the strand concentration in a reaction is 10, 20, 30, 40, 50, 60, 70, 80, 90 or 100 nM. The concentration of strand in a reaction may be less than 5 nM or greater than 1000 nM. The concentration of strand in a reaction may be less than 10 nM or greater than 1000 nM.

The ratio of any two strands (e.g., catalytic strand to concatemer-forming strand, or first concatemer strand to second concatemer strand) in a reaction described herein, in some embodiments, may be approximately 1:1.

The number of a particular type of strand in a reaction (e.g., ProPER or Co-Zipper) is non-limiting. A reaction may comprise, for example, 1-10$^{10}$ strands. In some embodiments, a reaction comprises 1-10, 1-10$^2$, 1-10$^3$, 1-10$^4$, 1-10$^5$, 1-10$^6$, 1-10$^7$, 1-10$^8$, 1-10$^9$, 1-10$^{10}$, or more, strands of a particular type (e.g., concatemer-forming strand, catalytic strand, and/or concatemer strand). In some embodiments, a reaction comprises 1-5, 1-10, 1-15, 1-20, 1-25, 1-30, 1-35, 1-40, 1-45, 1-50, 1-55, 1-60, 1-65, 1-70, 1-75, 1-80, 1-85, 1-90, 1-95, 1-100, 5-10, 5-15, 5-20, 5-25, 5-30, 5-35, 5-40, 5-45, 5-50, 5-55, 5-60, 5-65, 5-70, 5-75, 5-80, 5-85, 5-90, 5-95, 5-100, 10-15, 10-20, 10-25, 10-30, 10-35, 10-40, 10-45, 10-50, 10-55, 10-60, 10-65, 10-70, 10-75, 10-80, 10-85, 10-90, 10-95 or 10-100 strands. In some embodiments, a reaction comprises 1, 2, 3, 4, 5, 6, 7, 8, 9, 10, 11, 12, 13, 14, 15, 16, 17, 28, 19, 20, 21, 22, 23, 24 or 25 strands.

The kinetics of a reaction (e.g., a primer exchange reaction) may be controlled by varying temperature, time, buffer/salt conditions, and deoxyribonucleotide triphosphate (dNTP) concentrations, for example. Polymerases, like most enzymes, are sensitive to many buffer conditions, including ionic strength, pH and types of metal ions present (e.g., sodium ions vs. magnesium ions). Thus, the temperature at which a reaction is performed may vary from, for example, 4° C. to 65° C. (e.g., 4° C., 25° C., 37° C., 42° C. or 65° C.). In some embodiments, the temperature at which a reaction is performed is 4-25° C., 4-30° C., 4-35° C., 4-40° C., 4-45° C., 4-50° C., 4-55° C., 4-60° C., 10-25° C., 10-30° C., 10-35° C., 10- 40° C., 10-45° C., 10-50° C., 10-55° C., 10-60° C., 25-30° C., 25-35° C., 25-40° C., 25-45° C., 25-50° C., 25-55° C., 25-60° C., 25-65° C., 35-40° C., 35-45° C., 35-50° C., 35-55° C., 35-60° C., or 35-65° C. In some embodiments, a reaction is performed at room temperature, while in other embodiments, a reaction is performed at 37° C.

A reaction may be performed (incubated) for 30 minutes (min) to 24 hours (hr). In some embodiments, a reaction is carried out for 10 min, 35 min, 40 min, 45 min, 50 min, 55 min, 60 min, 1 hr, 2 hr, 3 hr, 4 hr, 5 hr, 6 hr, 7 hr, 8 hr, 9 hr, 10 hr, 11 hr, 12 hr, 18 hr or 24 hr.

Deoxyribonucleotides (dNTPs) are the "fuel" that drives a reaction herein (e.g., a primer exchange reaction). Thus, the kinetics of a reaction, in some embodiments, depends on the concentration of dNTPs in a reaction. The concentration of dNTPs in a prim reaction may be, for example, 2-1000 µM. In some embodiments, the dNTP concentration in a reaction is 2-10 µM, 2-15 µM, 2-20 µM, 2-25 µM, 2-30 µM, 2-35 µM, 2-40 µM, 2-45 µM, 2-50 µM, 2-55 µM, 2-60 µM, 2-65 µM, 2-70 µM, 2-75 µM, 2-80 µM, 2-85 µM, 2-90 µM, 2-95 µM, 2-100 µM, 2-110 µM, 2-120 µM, 2-130 µM, 2-140 µM, 2-150 µM, 2-160 µM, 2-170 µM, 2-180 µM, 2-190 µM, 2-200 µM, 2-250 µM, 2-300 µM, 2-350 µM, 2-400 µM, 2-450 µM, 2-500 µM, 2-600 µM, 2-700 µM, 2-800 µM, 2-900 µM or 2-1000 µM. For example, the dNTP concentration in a reaction may be 2 µM, 5 µM, 10 µM, 15 µM, 20 µM, 25 µM, 30 µM, 35 µM, 40 µM, 45 µM, 50 µM, 55 µM, 60 µM, 65 µM, 70 µM, 75 µM, 80 µM, 85 µM, 90 µM, 95 µM, 100 µM, 105 µM, 110 µM, 115 µM, 120 µM, 125 µM, 130 µM, 135 µM, 140 µM, 145 µM, 150 µM, 155 µM, 160 µM, 165 µM, 170 µM, 175 µM, 180 µM, 185 µM, 190 µM, 195 µM or 200 µM. In some embodiments, the dNTP concentration in a pr reaction is 10-20 µM, 10-30 µM, 10-40 µM, 10-50 µM, 10-60 µM, 10-70 µM, 10-80 µM, 10-90 µM or 10-100 µM.

In some embodiments, dNTP variants are used. For example, reactions herein may use hot start/clean amp dNTPs, phosphorothioate dNTPs, or fluorescent dNTPs. Other dNTP variants may be used. Because some modified dNTPs are less favorable than normal (unmodified) DNA-DNA binding, a catalytic strand back displacement process may be increased with their usage. Similarly, a catalytic strand comprised of a different type of nucleic acid (e.g., LNA, RNA or interspersed modified bases such as methyl dC or super T IDT modifications) may be used in some embodiments to increase the speed of a reaction by forming stronger bonds than the synthesized primer domain with respect to the catalytic strand.

EXAMPLES

Example 1: Experimental Validation of Proximity Primer Exchange Reaction (ProPER)

Compelling methods for detecting biomolecules, such as for disease diagnostics or imaging of tissues, require reactions should be (1) highly specific to the targets of interest, and (2) sensitive enough to detect low amounts or single copies of the biomolecule. We present the Proximity Primer Exchange Reaction (ProPER) that has unique advantages in achieving both of these goals. By relying on the successful targeting of multiple strands to a single target of interest, the background of detection can be significantly decreased. Moreover, this proximity is checked repeatedly in the process of the concatemerization, further ensuring specific interactions. The long strand produced by ProPER concatemerization can be used as a scaffold for fluorescent molecules, enabling the use of ProPER as a form of signal amplification. This allows the aggregation of potentially dozens or more fluorophores to single target biomolecules, producing signal which can then be visualized directly on a microscope or fluorescence scanner. The method is therefore both highly specific and highly sensitive and has the potential to outperform existing methods for detecting and imaging biomolecules.

Figure 1B:
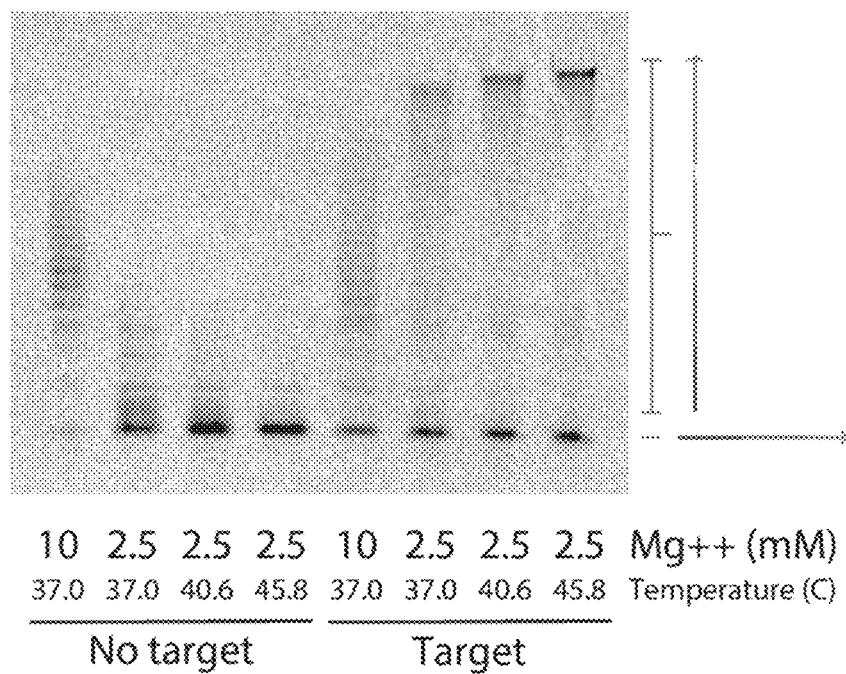

To experimentally validate the system, an optimization process was performed (FIGS. 1A-1B). The concatemer-forming strand and catalytic hairpin components were localized onto the same nucleic acid ('splint') strand, with a 10-nucleotide linker between their hybridization regions, and kept within spatial proximity (FIG. 1A) in solution. 2 nM of a Cy5-labeled concatemer-forming strand was combined with 2 nM of the catalytic hairpin strand and 2 nM of the splint strand (if present). Bst strand displacing polymerase and the appropriate dNTPs were added before PER concatemerization took place over a 1 hour period, and then the polymerase was heat inactivated at 80° C. for 20 minutes. The 8 reactions were then run on a 15% TBE-Urea PAGE denaturing gel and scanned under the Cy5 channel to visualize concatemerization. The reactions were performed in 1×PBS buffer with magnesium (MgSO4) supplemented between 2.5 mM and 10 mM final concentration, and the reactions were run between 37.0° C. and 45.8° C., as indicated below the gel lanes. (FIG. 1B). Under ideal conditions, the absence of the splint strand (target) produced no concatemerization, whereas including the splint strand resulted in the production of a long concatemer. The 4th condition tested, specifically at 45.8° C. with 2.5 mM magnesium present, resulted in very little concatemerization of the primer in the absence of the splint (4th lane from left), whereas the same condition with the splint present resulted in long concatemers several hundred bases long (rightmost lane in gel).

Example 2: Linker Distance Evaluation in ProPER

Figure 2A:
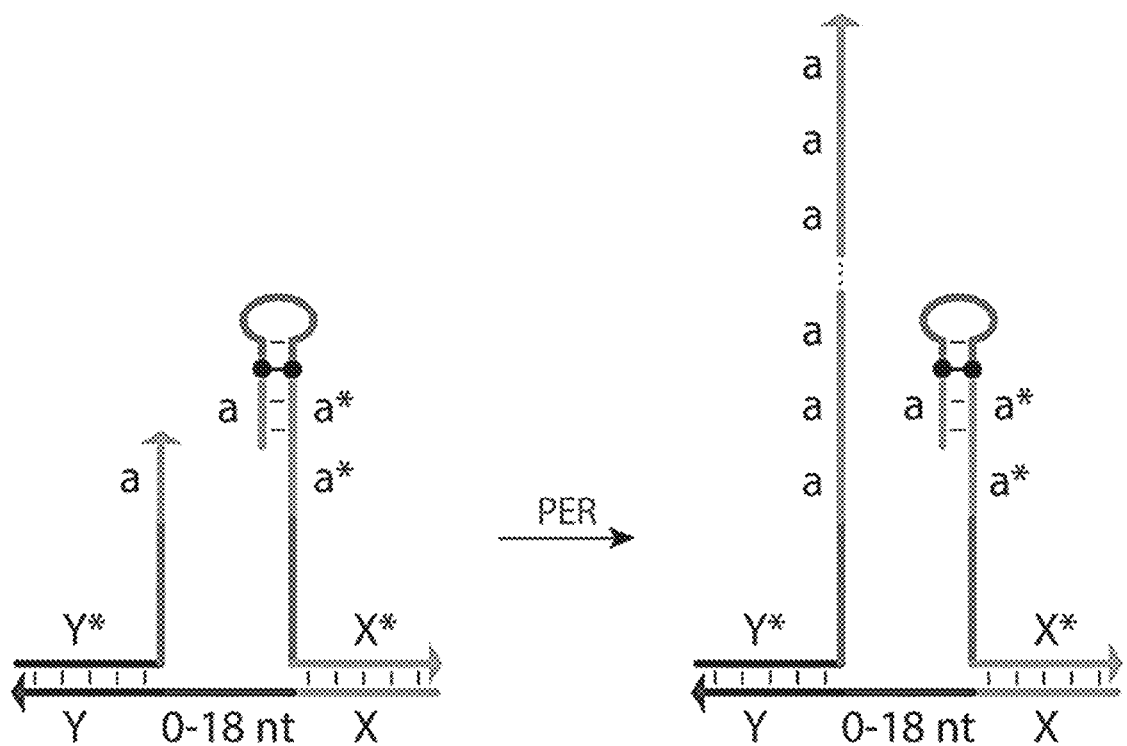
FIGS. 2A-2B provide an evaluation of the effects of linker distance on the utility of ProPER.
Figure 2B:
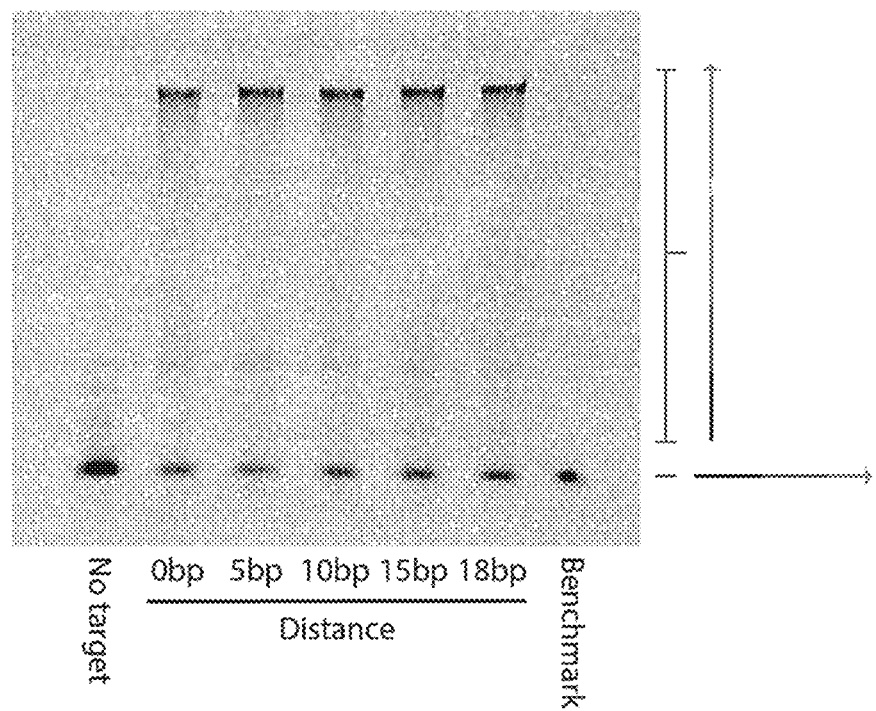

To assess the system's flexibility to a range of linker distances, an initial test was performed, in which the distance between the hybridization regions of the primer and hairpin components (domains Y* and X* in FIG. 1A) was varied between 0 and 18 nucleotides (FIG. 2A). 2 nM of a Cy5-labeled concatemer-forming strand was combined with 2 nM of the catalytic hairpin strand and 2 nM of the splint 'target' strand (if present). B st strand displacing polymerase and the appropriate dNTPs were added before PER concatemerization took place over a 1 hour period, and then the polymerase was heat inactivated at 80° C. for 20 minutes. The 6 reactions (plus a benchmark reaction that had only the primer and hairpins diluted to 2 nM each in 1×PBS for the last lane) were then run on a 15% TBE-Urea PAGE denaturing gel and scanned under the Cy5 channel to visualize concatemerization. The reactions were performed in 1×PBS buffer with magnesium (MgSO4) supplemented to 2.5 mM final concentration, and the reactions were run at 45.8° C. For the range of 5 distances tested, concatemerization efficiency turned out to be quite high and indistinguishable from each other under the particular gel experimental conditions (FIG. 2B). Specifically, negligible concatemerization occurred without the splint strand present, whereas all of the splints tested produced very long (several hundreds of bases) concatemers. The system was therefore flexible to a range of proximity distances.

Example 3: Applications of ProPER

Figure 3A:
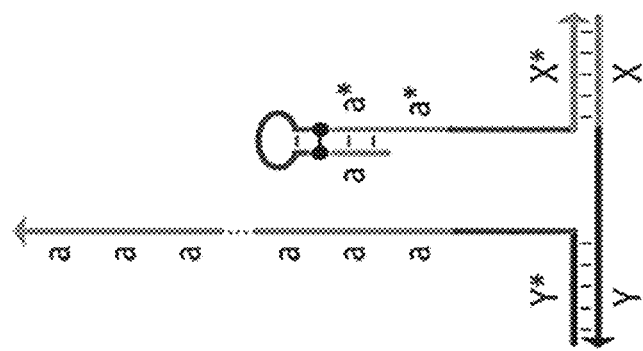
FIGS. 3A-3D provide schematics showing example applications of ProPER.
Figure 3A:
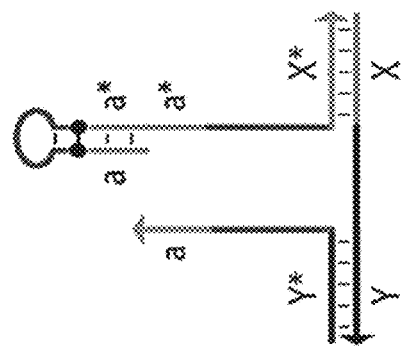
Figure 3A:
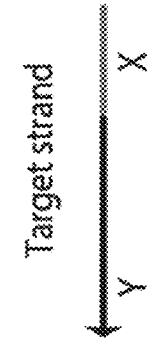
Figure 3B:
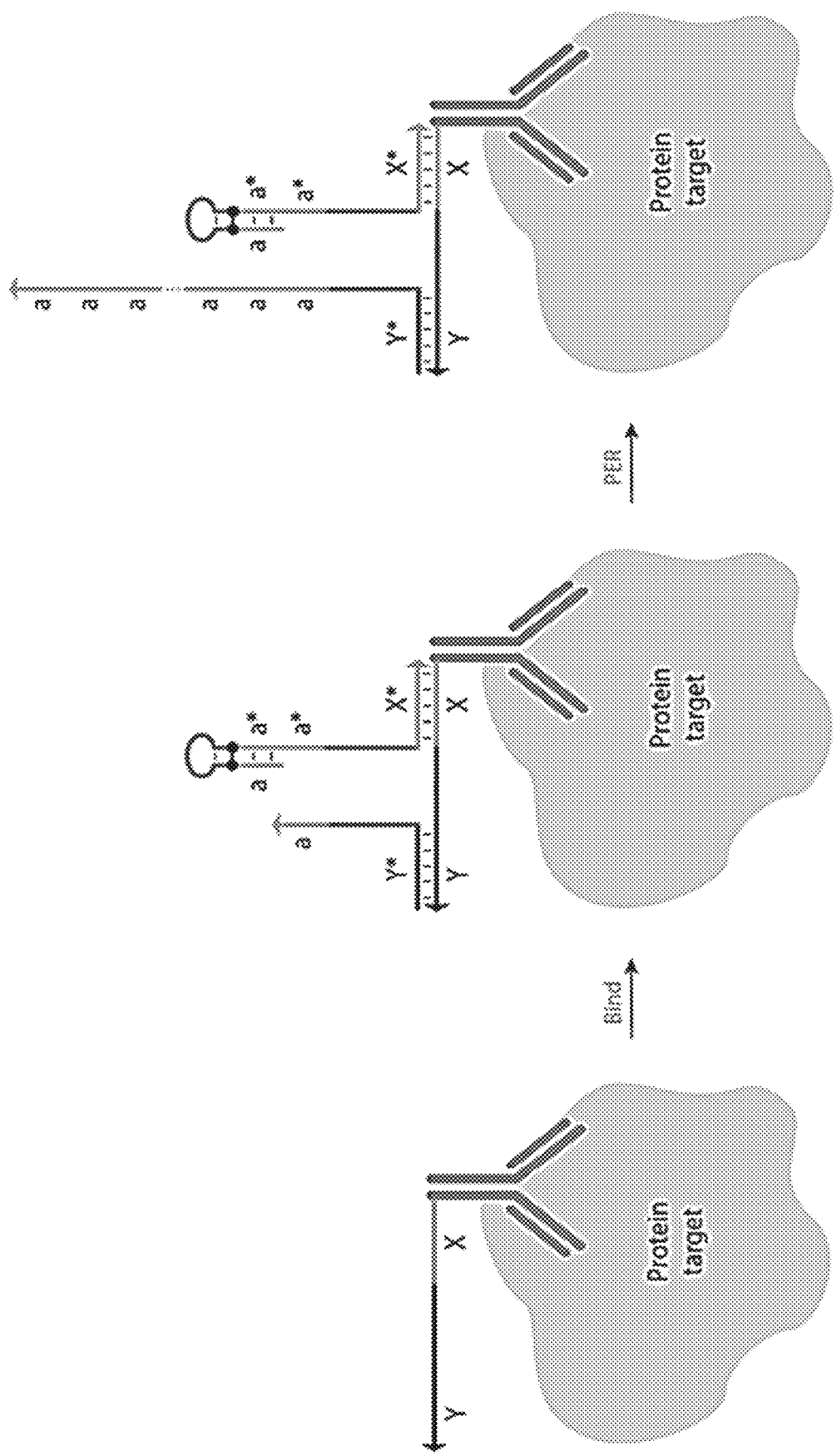
Figure 3C:
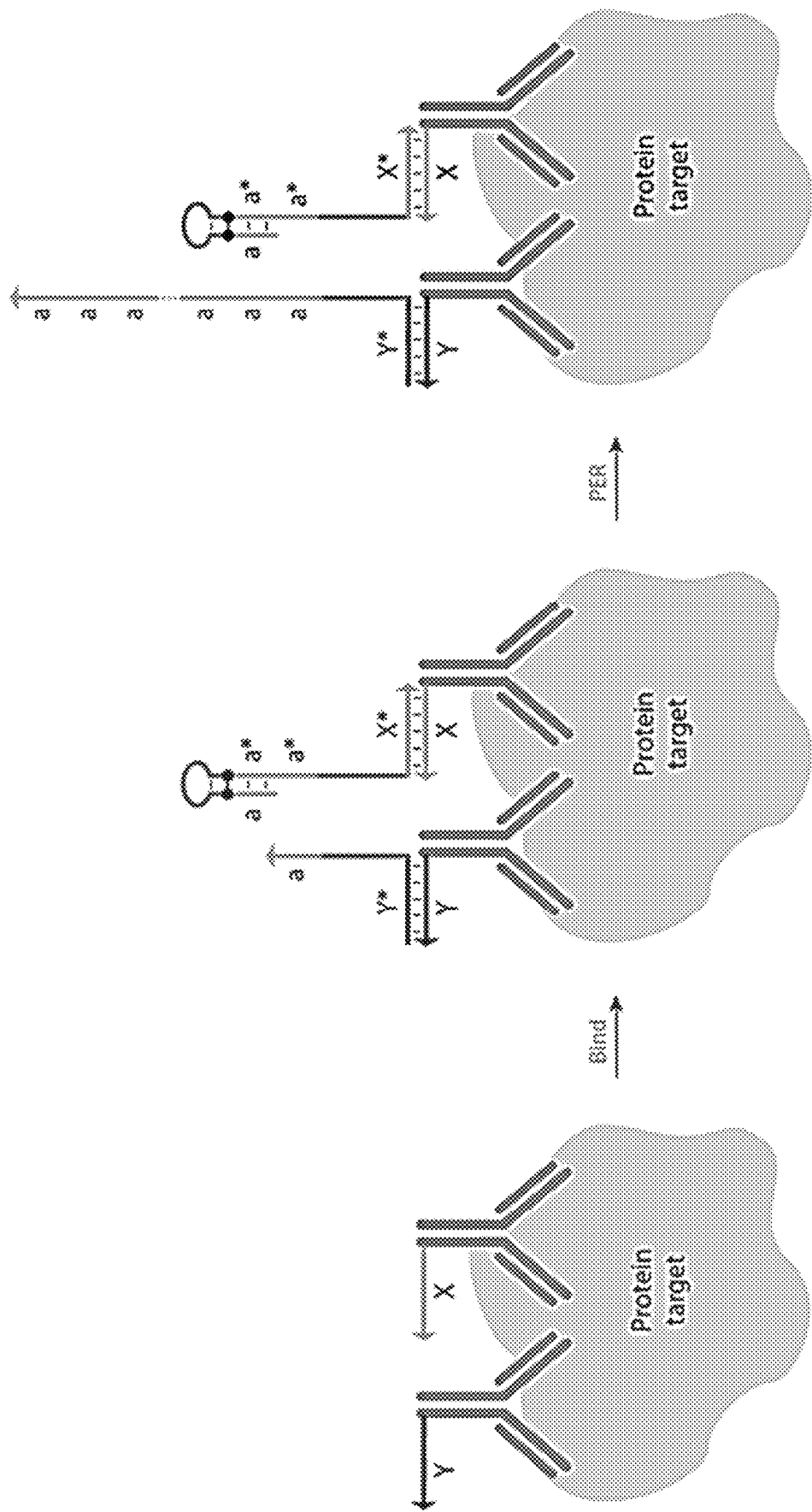
Figure 3D:
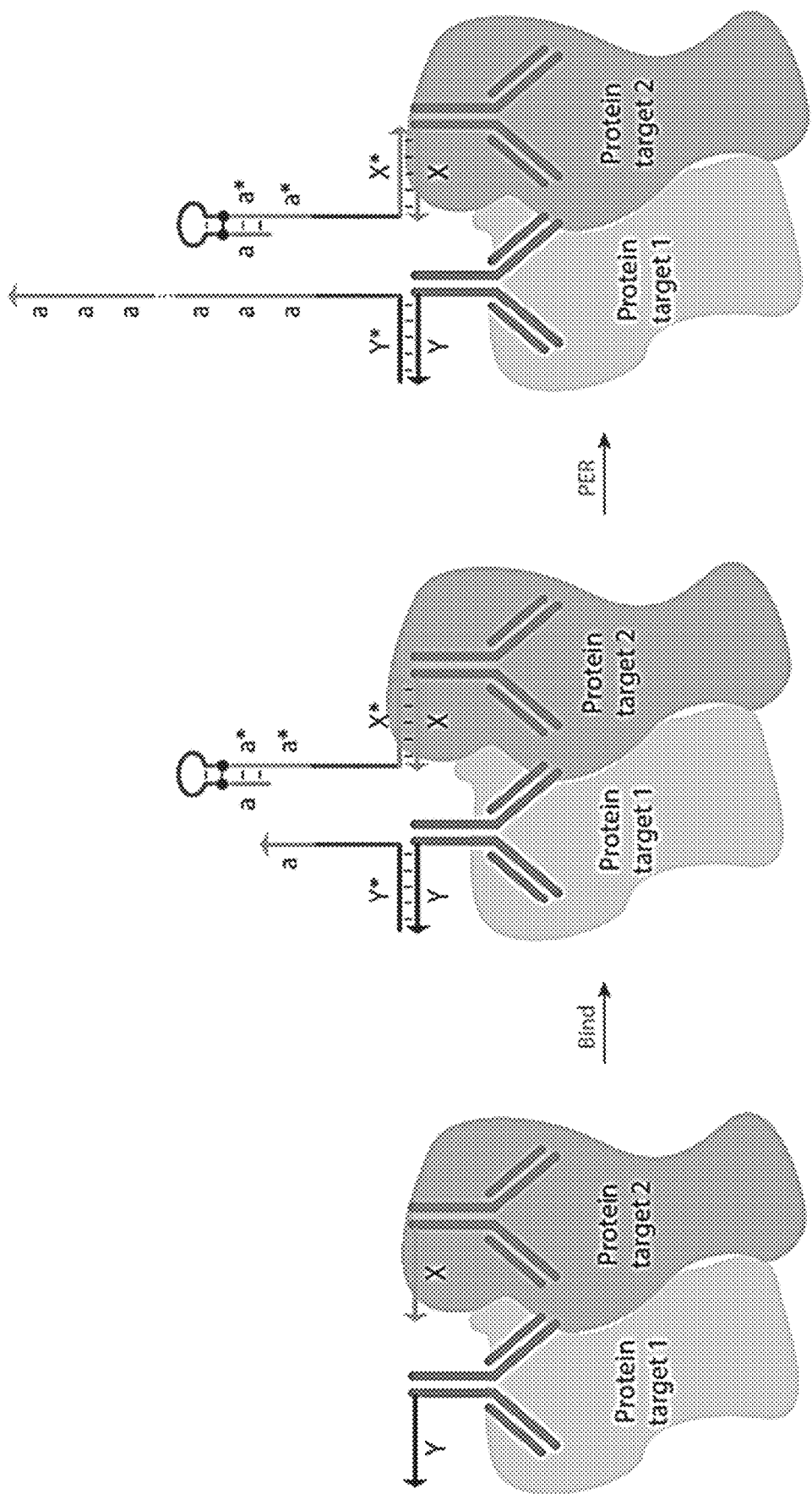

Applications of ProPER are performed diffusively in solution on immobilized targets for in vitro diagnostics, and in situ on strands fixed to a sample for low-background fluorescent imaging. First, a Proximity Primer Exchange Reaction (ProPER) is used to detect a nucleic acid target (DNA/RNA), wherein the concatemer-forming strand and catalytic hairpin strands are designed only to co-localize in the presence of the target ('splint') strand (FIG. 3A). The target sequence is tested in solution, immobilized, and detected in situ. Next, a ProPER is used to target a bridge strand conjugated to an antibody that targets a protein of interest (FIG. 3B). Third, a ProPER is used to very specifically detect individual proteins wherein the concatemer-forming strand is connected to one antibody that targets the protein and the catalytic hairpin is connected to another antibody that targets a different site on the protein (FIG. 3C). Finally, the proximity of two proteins are detected using a ProPER where the concatemer-forming strand and catalytic hairpin components are localized to antibodies that target proteins within the same biomolecular complex (FIG. 3D).

Example 4: Fluorescent Readout in ProPER

The concatemer produced by a ProPER is hybridized to complementary fluorescent imager strands, such as with the two-domain a* a* strand depicted in FIG. 4. The strength of the fluorescence signal reflects the length of the concatemer produced. Fluorescence is also visualized in bulk (for example when targets and concatemers are fixed to a surface and the total level of fluorescence is measured) or with a microscope to reveal the spatial positioning of the concatemers.

Example 5: Biomarker Detection Using ProPER

To detect biomarkers, one of the components, either a concatemer-forming strand or a catalytic hairpin, is attached to a surface (which may be paper, glass, plastic, or another substrate). Then, the remaining components are bound to this substrate-bound component. For example, blood serum or other fluids containing nucleic acid analytes of interest may be pre-mixed with a catalytic hairpin, or strands may be introduced sequentially through a series of bind and wash steps on the substrate. Once the primer-target-hairpin complex is formed, the additional hairpin strands are washed away through aspiration and re-suspension. Next, ProPER may be performed to produce concatemers, one for each bound target molecule of interest. Fluorescent imager strands are introduced to bind to the concatemer and then excess unbound imager strands are washed away. Finally, fluorescence output is read with one of two strategies: bulk fluorescence or spot counting. For bulk fluorescence, the total fluorescence level is read on the surface with an LED- or laser-based scanner, such as a plate reader. Alternatively, the number of individual fluorescent spots is counted, such as with a microscope or automated counter, and the density of spots can be mapped quantitatively to a concentration estimate of the original analyte. (FIG. 5)

Example 6: Multiple Proximity Detection Using ProPER

Figure 6A:
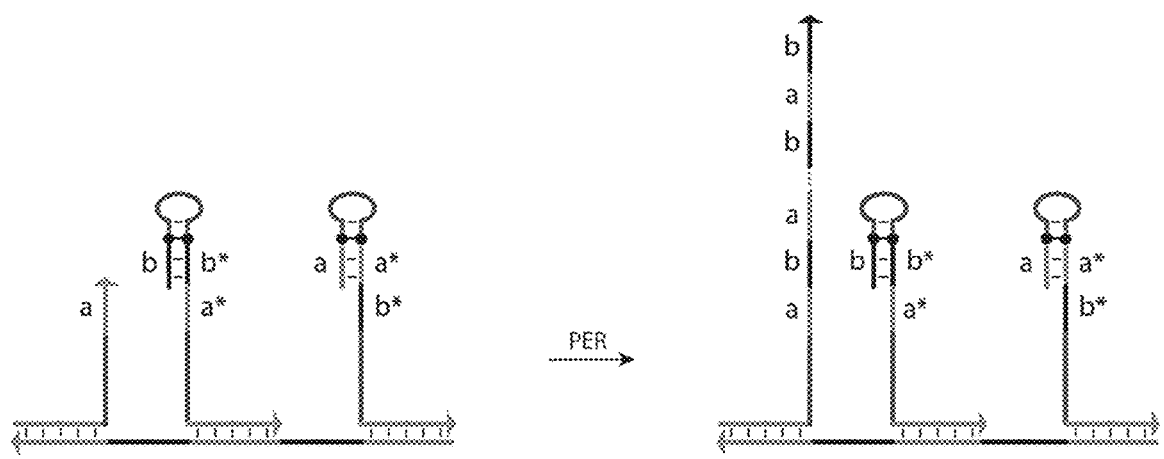
FIGS. 6A-6B provide schematics showing the use of ProPER in multiple proximity detection.
Figure 6B:
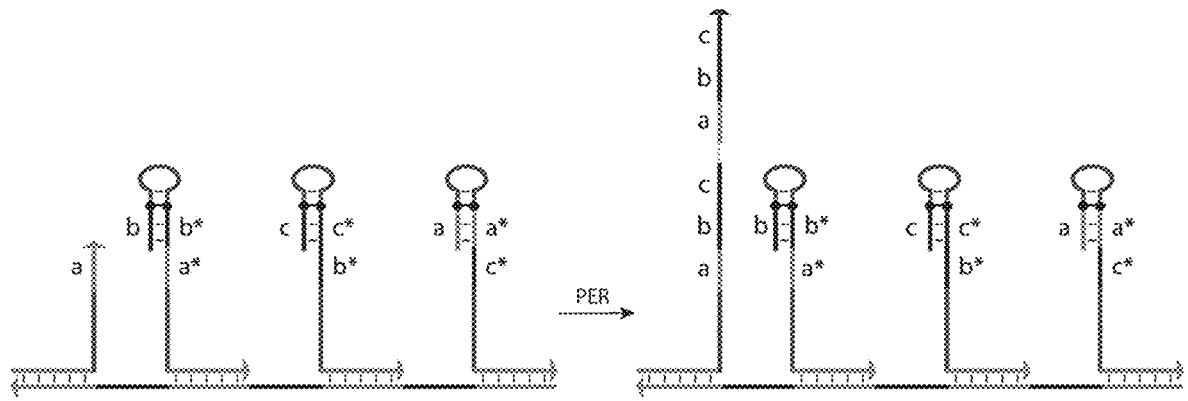

ProPER may be used to assess whether an arbitrary number of proximal hairpins can be detected to further increase specificity of target binding. One method of achieving this increased specificity is shown in FIGS. 6A-6B. FIG. 6A demonstrates that two catalytic hairpins are used to produce concatemers of the form 5'-a b a b . . . a b-3', to which a fluorescent imager strand complementary to the repeated units (such as 5'-b* a*-3') is bound to produce fluorescent output. FIG. 6B shows a similar setup with 3 hairpins that produces a concatemer of the form 5'-a b c a b c . . . a b c-3'. Hybridizing a fluorescent strand with sequence 5'-c* b* a*-3', enables specific fluorescent output of the concatemer. The number of hairpins may be increased arbitrarily, so that the number of molecules that are in spatial proximity for successful and repeated concatemerization is n+1, wherein n represents the number of hairpins.

Example 7: Proximity-Dependent PER Using Flexible PER Concatemer Linkers

Proximity detection was further verified using a variant of the ProPER approach and a long flexible linker (FIGS. 7A-7B). First, a repetitive in vitro PER reaction was used to generate a long concatemer on the 3' end of 42 mer 'bridge' strands with the first concatemer-forming strand (FIG. 7A). Then, a stepwise PER hairpin was introduced to append a different second PER primer sequence onto the 3' end of these PER concatemers. An in situ hybridization was performed by combining Cy3-labeled imager strands containing 42 mer bridge sequences with a mix of extended PER concatemers and catalytic hairpin strands, both of which contained the complementary 42 mer sequence to hybridize them to the concatemer-forming strands (FIG. 7B). This resulted in a mix of PER concatemer-forming strand and catalytic hairpins bound to strands tiled along the genome locus. The proximity-dependent PER reaction was then performed in situ as depicted previously, by introducing polymerase and dNTPs in buffer. Fluor-labeled imager strands targeting both the first (in vitro) and second (in situ) primer domain sequences on the concatemer-forming strands were then hybridized before imaging. This variant of proximity-dependent PER, which uses a flexible linker on the proximity-dependent PER primer strand, has several advantages. First, because the linker length was programmable by changing the in vitro PER conditions, the distance that the primer can reach may allow for different distances to be measured. Also, this linker can be imaged using the same method of fluorescent imager binding as the proximity-dependent PER concatemer sequence, enabling both the underlying probe sequences and the proximity-dependent reactions to be simultaneously visualized. This can be used for a two-color co-localization to validate the proximity-dependent PER signal only occurs where there are also probes present and also to inform where probes that were not proximal to hairpins were bound. Alternatively linkers of different sizes can be pre-synthesized by chemical DNA synthesis, with the primer site on 3', however utilizing PER for this step makes the synthesis more flexible for versatile needs and more cost-efficient.

Figure 8A:
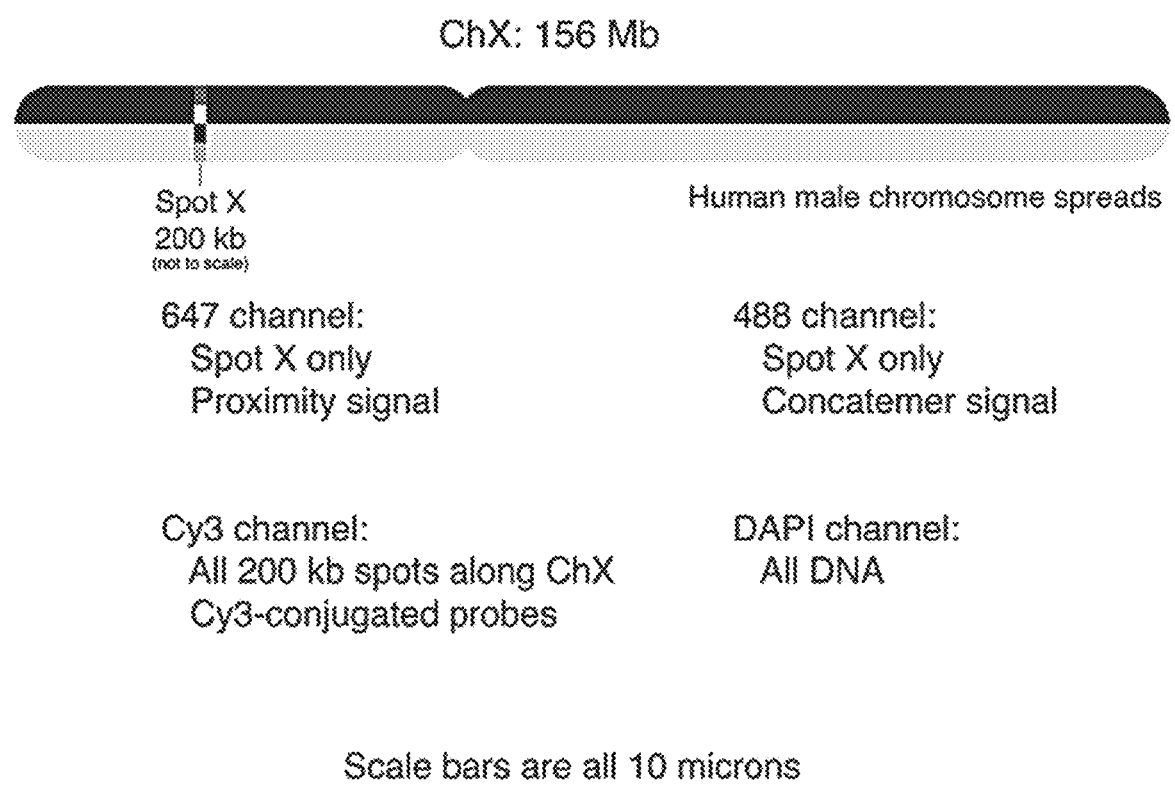
FIGS. 8A-8C provide fluorescence imaging results for proximity-dependent PER with flexible PER concatemer linkers.
Figure 8B:
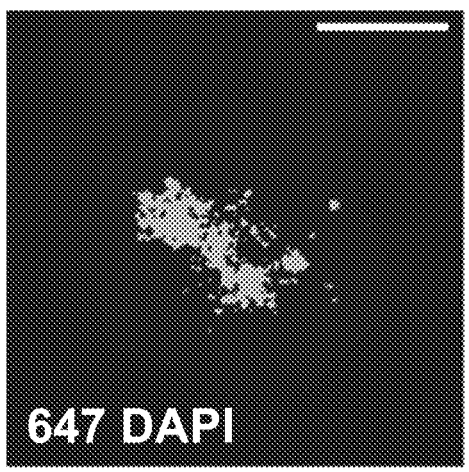
Figure 8B:
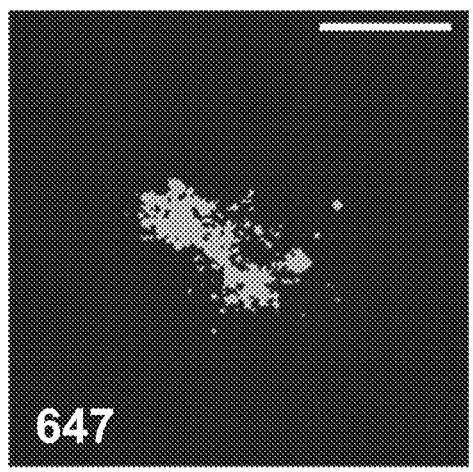
Figure 8B:
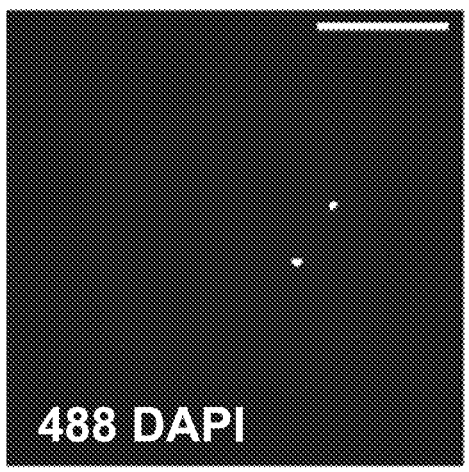
Figure 8B:
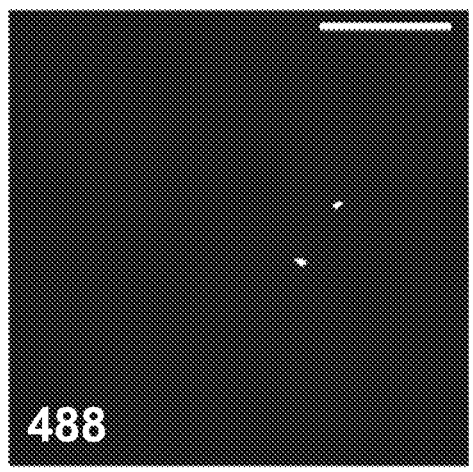
Figure 8B:
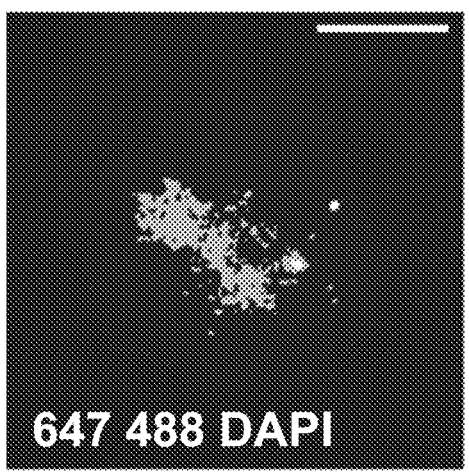
Figure 8B:
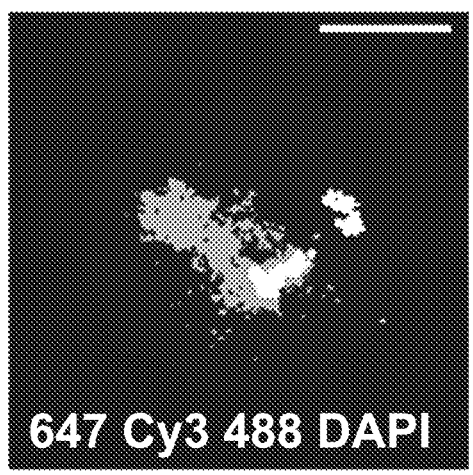
Figure 8C:
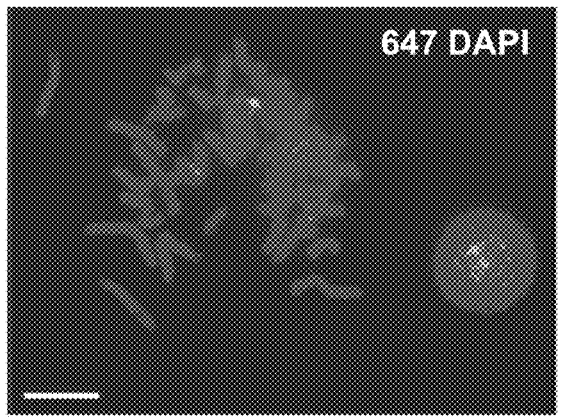
Figure 8C:
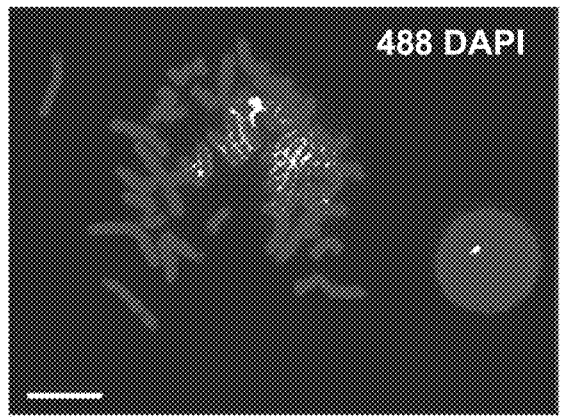
Figure 8C:
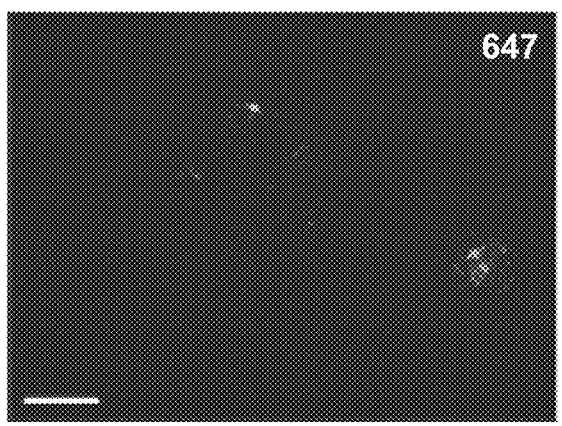
Figure 8C:
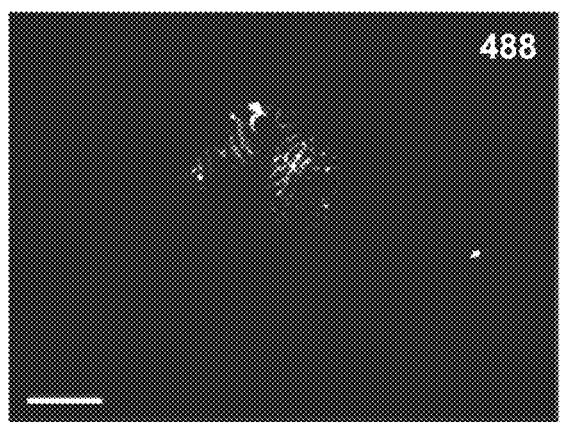
Figure 8C:
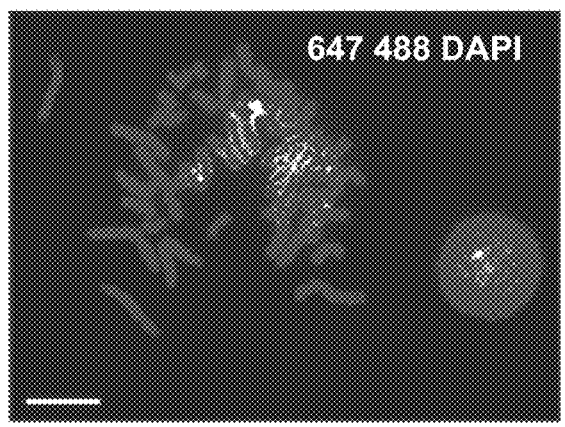
Figure 8C:
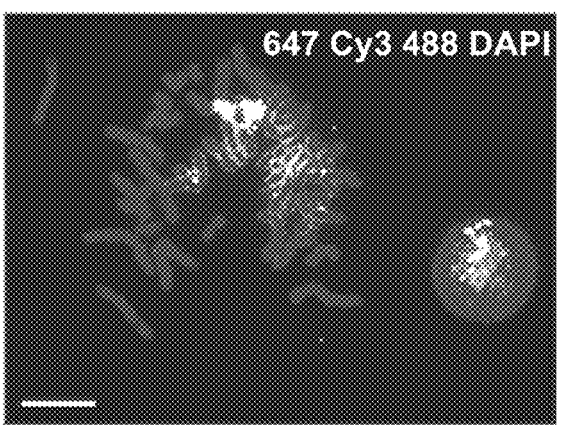

Results for the experiment depicted in FIGS. 7A-7B are shown in FIGS. 8A-8C. Cy3-labeled FISH probes targeting 18 200 kb spots spread along human chromosome X were used (shown in yellow), and the proximity-dependent PER reaction was performed only against probes targeting one of these spots (Spot X) (FIG. 8A). Different channel combinations for representative chromosome spreads and an interphase cell are shown in FIG. 8B-8C. As expected, green (488 channel, primary in vitro PER concatemer signal) and magenta (647 channel, proximity-dependent in situ PER concatemer signal) co-localized in one region. Furthermore, this region was contained within the larger yellow signal (Cy3 channel, entire chromosome X signal), further validating that the PER signal was visualized on the correct chromosome.

Example 8: Proximity Dependent PER Using Branched Strategy

Figure 9A:
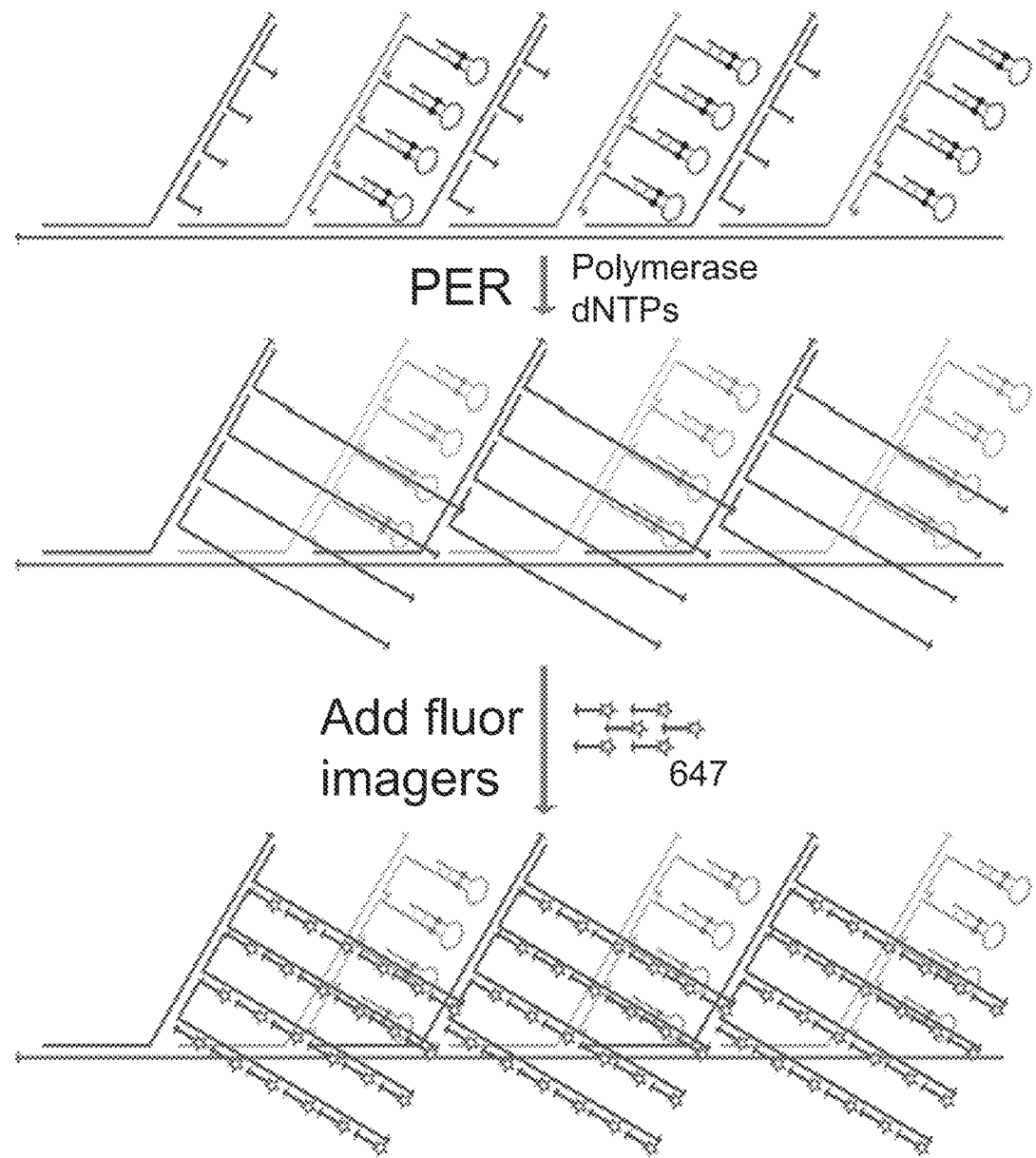
FIGS. 9A-9B provide a branched strategy for the use of proximity-dependent PER.
Figure 9B:
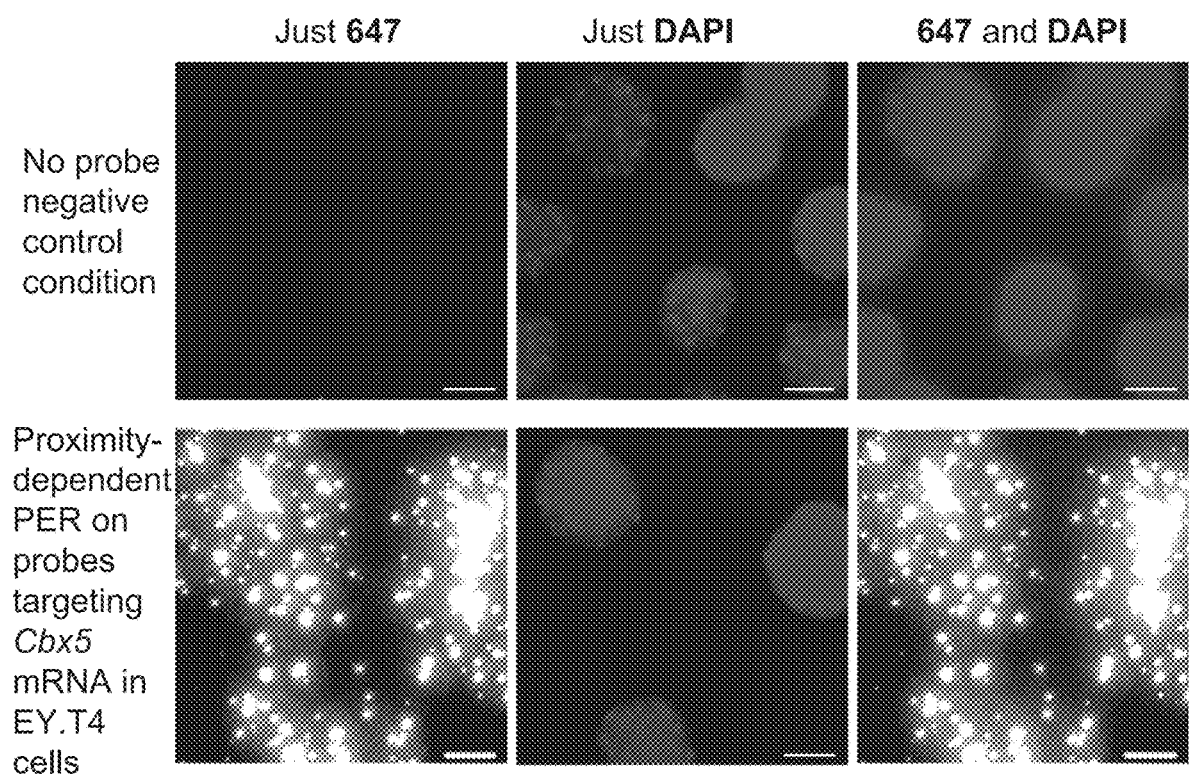

Another variant of proximity dependent PER using a branching strategy that can localize many concatemer-forming strand or catalytic hairpins to each probe sequence was experimentally validated (FIGS. 9A-9B). Similar to the previously described in vitro synthesis strategy described in FIGS. 7A-7B above, concatemer-forming strands were extended into long concatemers using in vitro PER reactions (FIG. 9A). Two different concatemer sequences were synthesized on alternating concatemer-forming strands tiled along the target RNA sequence. One of these sequences served as a scaffold for sequences containing a third primer on the 3' end to bind. The other sequence had many binding sites for complementary catalytic hairpin strands. In situ proximity dependent PER was performed to extend the third primer domain sequence, and fluor-labeled imager strands were hybridized to these synthesized strands. The Cbx5 mRNA transcript was chosen as a target, and the proximity dependent signal was read out in the with an Alexa 647 dye on the imager strands (FIG. 9B). As expected, proximity dependent signal showing RNA puncta distributed throughout the cell cytoplasm was only visualized in the experimental condition (647) and was not visualized in the negative control condition (comprising concatemer-forming strands only).

Example 9: Proximity-Dependent PER for Coincidence Detection

Figure 10A:
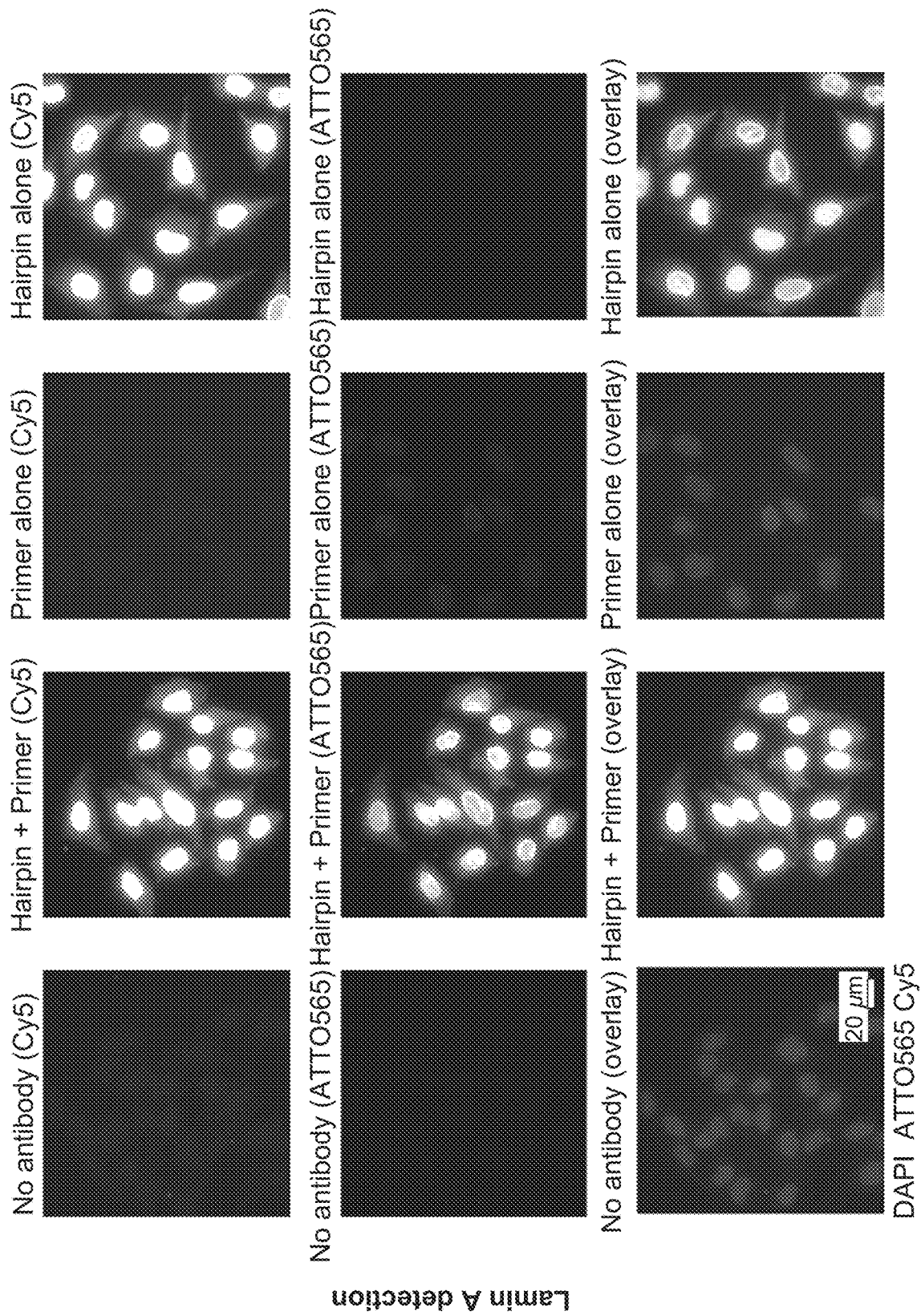
FIGS. 10A-10B provide fluorescence imaging results for proximity-dependent PER for coincidence detection of the same target, as demonstrated using imaging of cellular proteins in HeLa cell culture.
Figure 10B:
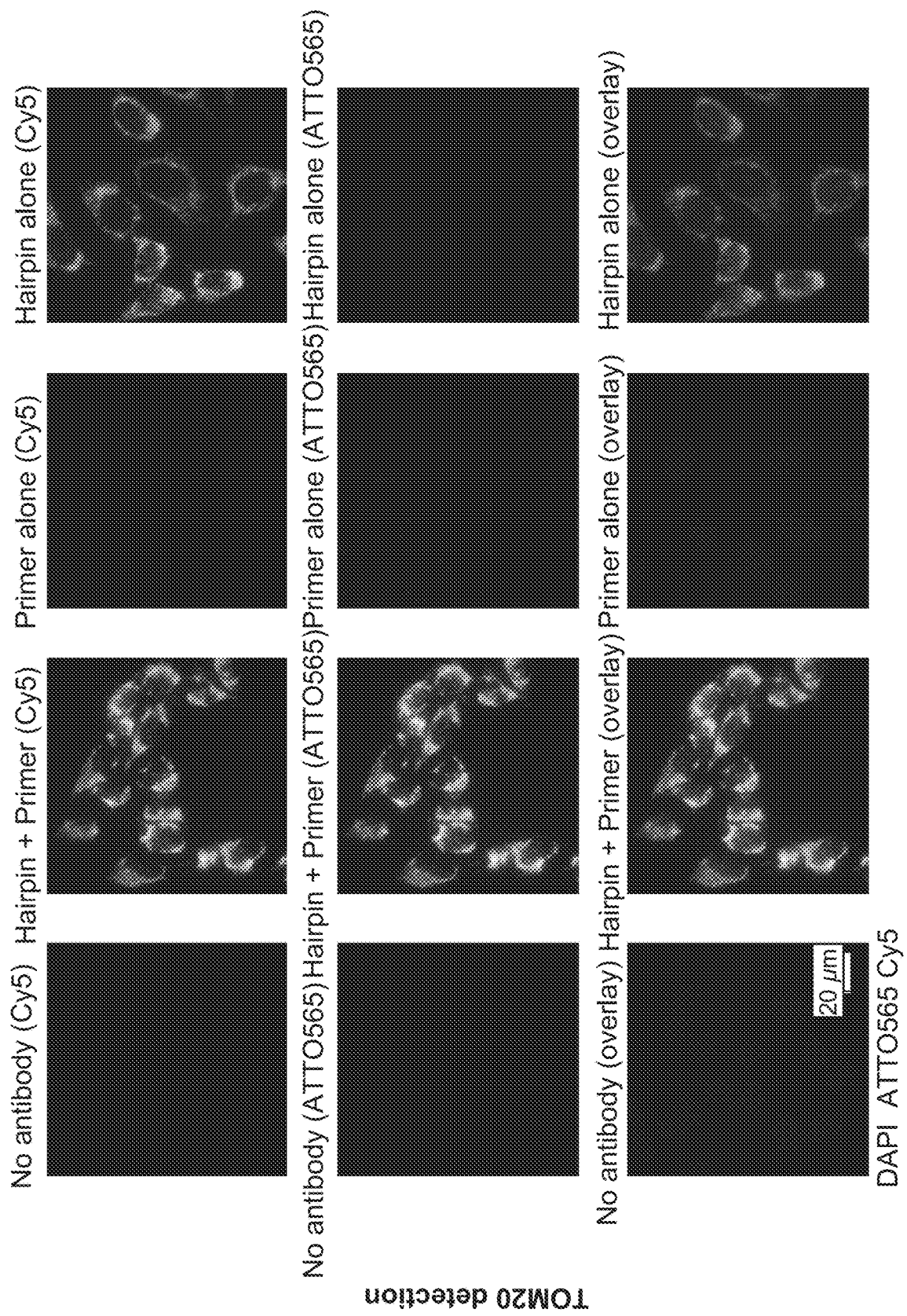

Coincidence-detection based signal amplification, as depicted in FIG. 10A-B was validated for protein visualization in cells by using a DNA-conjugated antibody that carries two docking sites: i) for capturing the concatemer-forming strand and, ii) for capturing the catalytic strand/hairpin. In the demonstration nuclear membrane localized Lamin A (FIG. 10A) or mitochondria localized TOM20 (FIG. 10B) was targeted. The antibodies were conjugated to a 25 mer 'bridge' strand (docking site for the catalytic hairpin capture strand via a flexible linker strand) followed by a 42 mer bridge strand (docking site for the concatemer-forming strand capture strand via a flexible linker). An in situ hybridization was performed by combining the capture strands for the concatemer-forming strand and catalytic strand, and the Cy5-labeled concatemer-forming strand. The proximity-dependent PER reaction was then performed in situ as depicted previously, by introducing polymerase and dNTPs in buffer. Atto565-Fluor imagers targeting the extended concatemers were then hybridized before imaging. Cy5 channel (green, fluorophore on primer) and ATTO565 channel (magenta), representing proximity-dependent in situ PER concatemer signals were visible together in only the samples where proximity extensions were performed in presence of both catalytic strand and concatemer-forming strand, and the antibodies with the binding sites. When the antibodies, or the capture strands were omitted for negative control experiments, no concatemerization was detected. The fluorescence signal for the primer was visualized for the conditions that the primer capture sequences were present. DAPI signal was shown to demonstrate the presence of cells that are specifically labeled only when both the strands are captured. The same reaction conditions were applied for all samples, except the omission of control strands.

This variant of proximity-dependent PER, facilities coincidence detection to decrease the nonspecific background that may be created by nonspecific probe or SNA strand binding and increase the signal-to-noise for imaging.

Example 10. Co-Zipper Strategy

Low signal and high background are important limitations that hamper the sensitivity and accuracy of detection systems. Signal amplification methods that create multiple positions for output (such as concatemers with repeated fluorophore binding sites) can provide improvement of the signal, but often also result in higher background and or low accuracy due to unspecificity of the probes. By relying on the discrimination between cooperative binding of two domains versus a single domain, fluorophore-labeled imager strands that bind two coincident concatemers can be used to aggregate many fluorophores to the area with extremely high specificity. The low background is achieved by relying on the proximity of the concatemers, as the probability that the two concatemers have both mis-localized to the same (sub-diffraction limit) location is extremely low. The combination of this high specificity with the linear amplification achieved through the repeated binding of imagers to concatemers enables the application of Co-Zipper for highly specific and highly sensitive biomarker detection (diagnostics) and imaging.

Herein, a proximity based detection of molecules involving an AND-gate logic wherein two components need to be in close-proximity for fluorescence signal to be generated is presented (Co-Zipper strategy). Ideally, this AND-gate would be applied at every step of detection to get maximum specificity. This may be achieved for concatemer signal amplification, by co-detection of two concatemer strands by a fluorophore-conjugated proximity imager strand that stably hybridizes only when bound to both concatemers (made of repeat sequences a and b respectively) (FIG. 11A). To enable the proximity needed to bind both concatemers, an imager strand containing short (8-10 nt) a* and b* domains was designed to bind each concatemer weakly, while binding the pair of concatemers with stable binding. In this way, the cooperative binding of each fluorophore-labeled strand required proximity of the two concatemers, allowing coincidence detection and an amplified signal. Formation of this zipper-like co-detection structure constitutes the basis of Co-Zipper strategy. Co-Zipper may also use to target a splint bridge strand conjugated to an antibody that targets a protein of interest. Split bridge accommodated two concatemers in close proximity, which were detected simultaneously for decreased background (FIG. 11B). To very specifically detect targets of interest such as individual proteins by using two antibodies, each of which carried a bridge that bound a different concatemer, targeting a different site or modification on the protein Co-Zipper was also used (FIG. 11C). To assess the proximity of two proteins using Co-Zipper, antibodies that target proteins within the same biomolecular complex may be used. All versions of Co-Zipper may be performed in solution, on immobilized targets for in vitro diagnostics, and in situ on strands fixed to a sample for low-background high-signal fluorescent imaging.

For fluorescence imaging Co-Zipper can serve for three main purposes: (1) Suppression of unspecific probe background: In cases where secondary probes are followed by primary probes for detection, an error propagation occurs due to unspecific background coming from both. Suppression of the background could be achieved by enabling detection only when both secondary probes are bound simultaneously. Both probes need to be present in close proximity to generate the signal (FIG. 11B). (2) Detection of desired target with reduced background and increased specificity: This can be achieved by tagging the same target molecule by two primary probes simultaneously. Both probes need to be present in close proximity to generate the signal (FIG. 11C). (3) Detection of interaction partners that co-localize in solution or in their native environment: This is achieved by using different probes that target different biomolecules, that need be simultaneously present in close proximity to generate the signal (FIG. 22D).

Example 11. In Situ Application of Co-Zipper

An in situ application of Co-Zipper was demonstrated using FISH probes targeting two repeat sequences in major satellite repeats of mouse embryonic fibroblasts. The two repeat sequences were appended with PER primers on their 3' end and were pre-extended into two orthogonal concatemers using PER in vitro. The resultant concatemers were then used for an in situ hybridization experiment using imager strands that yield strong signal only when bound to both concatemers, as the imager strand was designed to bind each individual concatemer with transient/weak affinity, as shown in the negative controls (FIG. 12).

Example 12. In Situ Application of Co-Zipper

Two nuclear lamina proteins Lamin A and B were bound by primary antibodies followed by cognate secondary antibodies conjugated to two orthogonal bridge nucleic acid sequences. Two orthogonal primers appended with sequences complementary to the bridge sequences were pre-extended into concatemers using PER in vitro. After immunostaining the concatemers were simultaneously applied onto the samples and hybridized onto the bridges. This was followed by addition of a imager strand to reveal the positions in which both proteins were co-localized (i.e. nuclear lamina). No signal was observed when one of the antibodies were omitted. Additional controls used imagers that bind stably to individual concatemers and showed significant staining in the cytoplasm in comparison to the very specific nuclear signal obtained by the imager strand that bound both concatemers (FIG. 13).

Example 13. Applications of Co-Zipper

Double stranded DNA-assemblies may be employed. Such structures can, for example, be prepared by hybridization chain reaction (HCR) [19] with addition of a toehold domain on one of the hairpins (FIG. 14A). An initiator strand of DNA (1+x) was added to a metastable mixture of two hairpin species triggered a chain reaction of hybridization events wherein hairpins form a long double-stranded concatemer. Normally, conjugation of fluorophores onto hairpins provides linear amplification. For the Co-Zipper adaptation, an extra toehold domain (of sequence a) was appended to one of the hairpins instead of the fluorophores. In this case, single stranded toehold domains were allowed to protrude from each of the structures, to maintain stable binding of proximity imager strands only when they are in close proximity to one another. Co-detection of double-stranded assemblies formed by hybridization chain reaction (HCR) was enabled by proximity imager (a*+b*). Single stranded toehold domains (a and b) protruding out of the double-stranded HCR product maintained stable binding of proximity imager strands only when both were in close proximity to one another (FIG. 14B).

REFERENCES

[1] Jares-Erijman, E. A. & Jovin, T. M. FRET imaging. Nat Biotechnol 21, 1387-1395, doi:10.1038/nbt896 (2003).
[2] Weibrecht, I. et al. In situ detection of individual mRNA molecules and protein complexes or post-translational modifications using padlock probes combined with the in situ proximity ligation assay. Nat Protoc 8, 355-372, doi:10.1038/nprot.2013.006 (2013).
[3] Hattori, N., Niwa, T., Kimura, K., Helin, K. & Ushijima, T. Visualization of multivalent histone modification in a single cell reveals highly concerted epigenetic changes on differentiation of embryonic stem cells. *Nucleic Acids Res* 41, 7231-7239, doi:10.1093/nar/gkt528 (2013).
[4] Kishi, Jocelyn Y., et al. "Programmable autonomous synthesis of single-stranded DNA." *Nature Chemistry* (2017).
[5] Yurke, Bernard, and Allen P. Mills. "Using DNA to power nanostructures." *Genetic Programming and Evolvable Machines* 4.2 (2003): 111-122.
[6] Seelig, Georg, et at "Enzyme-free nucleic acid logic circuits." *science* 314.5805 (2006): 1585-1588.
[7] Tyagi, Sanjay, and Fred Russell Kramer. "Molecular beacons: probes that fluoresce upon hybridization." *Nature biotechnology* 14.3 (1996): 303-308.
[8] Zhang, David Yu, and Erik Winfree. "Control of DNA strand displacing kinetics using toehold exchange." *Journal of the American Chemical Society* 131.47 (2009): 17303-17314.
[9] Jares-Erijman, E. A. & Jovin, T. M. FRET imaging. *Nat Biotechnol* 21, 1387-1395, doi:10.1038/nbt896(2003).
[10] Weibrecht, I. et al. In situ detection of individual mRNA molecules and protein complexes or post-translational modifications using padlock probes combined with the in situ proximity ligation assay. Nat Protoc 8, 355-372, doi:10.1038/nprot.2013.006 (2013).
[11] Hattori, N., Niwa, T., Kimura, K., Helin, K. & Ushijima, T. Visualization of multivalent histone modification in a single cell reveals highly concerted epigenetic changes on differentiation of embryonic stem cells. *Nucleic Acids Res* 41, 7231-7239, doi:10.1093/nar/gkt528 (2013).
[12] Carlton, J. G., and P. J. Cullen. "Coincidence Detection in Phosphoinositide Signaling." Trends Cell Biol 15.10 (2005): 540-7.
[13] Kishi, Jocelyn Y., et al. "Programmable autonomous synthesis of single-stranded DNA." *Nature Chemistry* (2017).
[14] Lizardi, P. M. et al. Mutation detection and single-molecule counting using isothermal rolling-circle amplification. *Nat. Genet.* 19, 225-232 (1998).
[15] Fire A, Xu S. Rolling replication of short DNA circles. *Proc. Natl. Acad. Sci.* 92, 4641-4645 (1995).
[16] Ali, M. Monsur, et al. "Rolling Circle Amplification: A Versatile Tool for Chemical Biology, Materials Science and Medicine." (2014).
[17] Yurke, Bernard, and Allen P. Mills. "Using DNA to power nanostructures." *Genetic Programming and Evolvable Machines* 4.2 (2003): 111-122.
[18] Seelig, Georg, et al. "Enzyme-free nucleic acid logic circuits." *Science* 314.5805 (2006): 1585-1588,

[19] Dirks, R. M. & Pierce, N. A. Triggered amplification by hybridization chain reaction. *Proc. Natl. Acad. Sci. USA* 101, 15275-15278 (2004).

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The terms "about" and "substantially" preceding a numerical value mean±10% of the recited numerical value.

Where a range of values is provided, each value between the upper and lower ends of the range are specifically contemplated and described herein.

What is claimed is:

1. A method of screening for a target molecule, the method comprising:
   (a) contacting a first composition suspected of comprising a target molecule with a second composition, wherein the second composition comprises (i) a first target-binding molecule that binds specifically to a first epitope, (ii) a catalytic strand comprising a hairpin with a stem and a loop, wherein the catalytic strand binds to the first target-binding molecule, and wherein the catalytic strand comprises a molecule or modification that terminates polymerization, (iii) a second target-binding molecule that binds specifically to a second epitope, (iv) a concatemer-forming strand comprising a primer domain, wherein the primer domain is complementary to the stem, and the concatemer-forming strand binds to the second target-binding molecule, (v) a labeled imager strand that is complementary to the primer domain, (vi) a strand-displacing polymerase, and (vii) dNTPs; and
   (b) detecting presence or absence of the labeled imager strand, wherein presence of the labeled imager strand indicates presence of the target molecule.

2. The method of claim 1 further comprising an excess of catalytic strands.

3. The method of claim 1, wherein the first target-binding molecule and/or the second target-binding molecule is an antibody.

4. The method of claim 1, wherein the catalytic strand binds to the first target-binding molecule through an intermediate linker and/or the concatemer-forming strand binds to the second target-binding molecule through an intermediate linker.

5. The method of claim 1, wherein the first target-binding molecule is linked to a first linker strand comprising a first domain to which the catalytic strand binds and/or wherein the second target-binding molecule is linked to a second linker strand comprising a second domain to which the concatemer-forming strand binds.

6. The method of claim 1, wherein the target molecule is present in a fixed tissue.

7. The method of claim 1, wherein the labeled imager strand comprises a detectable label selected from fluorophores, quantum dots, polymer dots, metal ions, biotin, horseradish peroxidase, magnetic particles, and tyramide.

8. The method of claim 1, wherein the first epitope is a first epitope of the target molecule and the second epitope is a second epitope of the target molecule.

9. The method of claim 1, wherein the first epitope is an epitope of a first protein and the second epitope is an epitope of a second protein, and wherein the target molecule is the first protein or the second protein.

10. A method of detecting a target molecule, the method comprising:
    (a) contacting the target molecule with a composition comprising (i) a first target-binding molecule that binds specifically to a first epitope, (ii) a catalytic strand comprising a hairpin with a stem and a loop, wherein the catalytic strand binds to the first target-binding molecule, and wherein the catalytic strand comprises a molecule or modification that terminates polymerization, (iii) a second target-binding molecule that binds specifically to a second epitope, (iv) a concatemer-forming strand comprising a primer domain, wherein the primer domain is complementary to the stem, and the concatemer-forming strand binds to the second target-binding molecule, (v) a labeled imager strand that is complementary to the primer domain, (vi) a strand-displacing polymerase, and (vii) dNTPs; and
    (b) detecting the labeled imager strand, thereby detecting the target molecule.

11. The method of claim 10 further comprising an excess of catalytic strands.

12. The method of claim 10, wherein the first target-binding molecule and/or the second target-binding molecule is an antibody.

13. The method of claim 10, wherein the catalytic strand binds to the first target-binding molecule through an intermediate linker and/or the concatemer-forming strand binds to the second target-binding molecule through an intermediate linker.

14. The method of claim 10, wherein the first target-binding molecule is linked to a first linker strand comprising a first domain to which the catalytic strand binds and/or wherein the second target-binding molecule is linked to a second linker strand comprising a second domain to which the concatemer-forming strand binds.

15. The method of claim 10, wherein the target molecule is present in a fixed tissue.

16. The method of claim 10, wherein the labeled imager strand comprises a detectable label selected from fluorophores, quantum dots, polymer dots, metal ions, biotin, horseradish peroxidase, magnetic particles, and tyramide.

17. The method of claim 10, wherein the first epitope is a first epitope of the target molecule and the second epitope is a second epitope of the target molecule.

18. The method of claim 10, wherein the first epitope is an epitope of a first protein and the second epitope is an epitope of a second protein, and wherein the target molecule is the first protein or the second protein.

19. A method of detecting one or more protein target(s), the method comprising:

(a) combining a composition comprising one or more protein targets, a strand-displacing polymerase, and dNTPs with:
- (i) a first antibody-DNA conjugate that binds specifically to a first epitope and a second antibody-DNA conjugate that binds specifically to a second epitope;
- (ii) a catalytic nucleic acid strand comprising a hairpin that includes a stem, a loop, and a molecule or modification that terminates polymerization, wherein the catalytic strand binds to the DNA of the first antibody-DNA conjugate;
- (iii) a concatemer-forming nucleic acid strand comprising a primer domain that is complementary to the stem of the hairpin of the catalytic nucleic acid strand, wherein the concatemer-forming nucleic acid strand binds to the DNA of the second antibody-DNA conjugate; and
- (iv) an imager nucleic acid strand comprising a detectable label, wherein the imager nucleic acid strand is complementary the primer domain of the concatemer-forming nucleic acid strand, wherein the first epitope and the second epitope are on a single protein target, or wherein the first epitope is on a first protein target and the second epitope is on a second protein target; and (b) detecting the imager nucleic acid strand, thereby detecting the one or more protein target(s).

20. The method of claim 19, wherein the detectable label is selected from fluorophores, quantum dots, polymer dots, metal ions, biotin, horseradish peroxidase, magnetic particles, and tyramide.

* * * * *

UNITED STATES PATENT AND TRADEMARK OFFICE
CERTIFICATE OF CORRECTION

| | |
|---|---|
| PATENT NO. | : 11,981,956 B2 |
| APPLICATION NO. | : 16/964527 |
| DATED | : May 14, 2024 |
| INVENTOR(S) | : Sinem K. Saka et al. |

Page 1 of 1

It is certified that error appears in the above-identified patent and that said Letters Patent is hereby corrected as shown below:

In the Specification

At Column 1, Lines 15-21, please change the sentence:
"This invention was made with government support under N00014-16-1-2410 awarded by Department of Defense, under EB018659 and HL145600 awarded by National Institutes of Health, and under 1317291 awarded by National Science Foundation. The government has certain rights in the invention."

To:
--This invention was made with government support under EB018659 and HL145600 awarded by National Institutes of Health (NIH) and under N00014-16-1-2410 awarded by U.S. Office of Naval Research (NAVY/ONR) and under 1317291 awarded by National Science Foundation (NSF). The government has certain rights in the invention.--

Signed and Sealed this
Thirtieth Day of September, 2025

John A. Squires
*Director of the United States Patent and Trademark Office*